(12) United States Patent
Gupta et al.

(10) Patent No.: US 6,265,576 B1
(45) Date of Patent: Jul. 24, 2001

(54) TRISARYL-1,3,5-TRIAZINE ULTRAVIOLET LIGHT ABSORBERS

(75) Inventors: Ram Baboo Gupta, Stamford; Dennis John Jakiela, Orange; Thomas P. Sassi, Stamford; Gottfried Haacke, New Canaan, all of CT (US)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/197,747

(22) Filed: Nov. 20, 1998

Related U.S. Application Data

(60) Provisional application No. 60/066,357, filed on Nov. 21, 1997.

(51) Int. Cl.$^7$ .................................................. C07D 251/24
(52) U.S. Cl. ............................................................ 544/216
(58) Field of Search ............................................... 544/216

(56) References Cited

U.S. PATENT DOCUMENTS

| | | | |
|---|---|---|---|
| 3,249,608 | * 5/1966 | Biland et al. | 260/248 |
| 3,843,371 | * 10/1974 | Piller et al. | 96/84 |
| 5,106,891 | 4/1992 | Valet | 524/100 |
| 5,189,084 | 2/1993 | Birbaum et al. | 524/100 |
| 5,322,868 | 6/1994 | Valet et al. | 524/100 |
| 5,354,794 | 10/1994 | Stevenson et al. | 524/100 |
| 5,597,854 | 1/1997 | Birbaum et al. | 524/100 |

FOREIGN PATENT DOCUMENTS

| | | |
|---|---|---|
| 434 608 A1 | 6/1991 | (EP) . |
| 0 434 608 | * 6/1991 | (EP) . |
| 693 483 A1 | 1/1996 | (EP) . |
| 0 693 483 | * 1/1996 | (EP) . |
| 2 363 133 | * 3/1978 | (FR) . |

OTHER PUBLICATIONS

Ullmann's Encyclopedia of Industrial Chemistry, 5$^{th}$ Edtion, vol. A18, p. 405, 1991.

* cited by examiner

*Primary Examiner*—Richard L. Raymond
*Assistant Examiner*—Venkataraman Balasubramanian
(74) *Attorney, Agent, or Firm*—Tyler A. Stevenson

(57) ABSTRACT

This invention relates generally to amido or carbamate substituted trisaryl-1,3,5-triazines and the use thereof to protect against degradation by environmental forces, inclusive of ultraviolet light, actinic radiation, oxidation, moisture, atmospheric pollutants and combinations thereof. The new class of trisaryl-1,3,5-triazines comprises an aryl ring attached to the triazine ring (and preferably an aryl ring containing a hydroxyl group, either free or blocked to form a latent stabilizer, ortho- to the point of attachment to the triazine ring) substituted with a group comprising a bondable amido/carbamate containing group para- to the point of attachment to the triazine ring. These materials may, under the appropriate circumstances, be bonded to formulations comprising coatings, polymers, resins, organic compounds and the like via reaction of the bondable functionality with the materials of the formulation. A method for stabilizing a material by incorporating such amido or carbamate substituted trisaryl-1,3,5-triazines is also disclosed.

26 Claims, No Drawings

TRISARYL-1,3,5-TRIAZINE ULTRAVIOLET LIGHT ABSORBERS

This application claims the benefit under 35 USC 119(e) of U.S. Provisional Application Ser. No. 60/066,357, filed Nov. 21, 1997.

BACKGROUND OF THE INVENTION

1. Field of the Invention

This invention relates generally to novel amido or carbamate substituted trisaryl-1,3,5-triazines and the use thereof to protect against degradation by environmental forces, inclusive of ultraviolet light, actinic radiation, oxidation, moisture, atmospheric pollutants and combinations thereof.

2. Description of Related Art

Exposure to sunlight and other sources of ultraviolet radiation is known to cause degradation of a variety of materials, especially polymeric materials. For example, polymeric materials such as plastics often discolor and/or become brittle as a result of prolonged exposure to ultraviolet light. Accordingly, a large body of art has been developed directed towards materials such as ultraviolet light absorbers and stabilizers which are capable of inhibiting such degradation.

A class of materials known to be ultraviolet light absorbers are trisaryl-1,3,5-triazines, in which at least one of the aryl rings has a hydroxyl group ortho to the point of attachment to the triazine ring. In general this class of materials is well known in the art. Disclosures of a number of such trisaryl-1,3,5-triazines, as well as processes for preparing and uses thereof, can be found in the following publications, all of which are incorporated by reference herein for all purposes as if fully set forth: U.S. Pat. No. 3,118,887, U.S. 3,242,175, U.S. 3,244,708, U.S. 3,249,608, U.S. 3,268,474, U.S. 3,423,360, U.S. 3,444,164, U.S. 3,843,371, U.S. 4,619,956, U.S. 4,740,542, U.S. 4,775,707, U.S. 4,826,978, U.S. 4,831,068, U.S. 4,962,142, U.S. 5,030,731, U.S. 5,059,647, U.S. 5,071,981, U.S. 5,084,570, U.S. 4,831,068, U.S. 4,962,142, U.S. 5,030,731, U.S. 5,059,647, U.S. 5,071,981, U.S. 5,084,570, U.S. 5,106,891, U.S. 5,185,445, U.S. 5,189,084, U.S. 5,198,498, U.S. 5,288,778, U.S. 5,298,067, U.S. 5,300,414, U.S. 5,322,868, U.S. 5,354,794, U.S. 5,364,749, U.S. 5,369,140, U.S. 5,410,048, U.S. 5,412,008, U.S. 5,420,204, U.S. 5,461,151, U.S. 5,476,937, U.S. 5,478,935, U.S. 5,489,503, U.S. 5,543,518, U.S. 5,538,840, U.S. 5,545,836, U.S. 5,563,224, U.S. 5,575,958, U.S. 5,591,850, U.S. 5,597,854, GB1033387, CH480091, CH484695, EP-A-0434608, EP-A-0532006, EP-A-0649841. EP-A-0693483, EP-A-0704560, WO95/05645, WO95/22959 and WO96/28431.

Typically, the aforementioned aryl ring with the hydroxyl group ortho to the point of attachment to the triazine ring is based on resorcinol and, consequently, this aryl ring also contains a second substituent (either a hydroxyl group or a derivative thereof) para- to the point of attachment to the triazine ring. This second substituent can be "non-reactive," as in the case of an alkyloxy group, or "reactive" as in the case of a hydroxyalkyloxy (active hydrogen reactive site) or (meth)acryloyl (ethylenic unsaturation reactive site) group. For the purposes of the present invention, the former are referred to as "non-bondable" trisaryl-1,3,5-triazines and the latter are referred to as "bondable" trisaryl-1,3,5-triazines.

Many polymer additives (such as ultraviolet light stabilizers) may suffer from a disadvantage that they volatilize or migrate out of the polymer substrate to be protected, or that they are adsorbed (chemically or physically) by one or more systems components (such as pigments), thereby diminishing their effectiveness.

Bondable stabilizers have a potential advantage in this respect in that, depending on the bondable functionality and the particular polymer system to be stabilized, they can be chemically incorporated into a polymer structure via reaction of the bondable functionality either during polymer formation (such as in the case of polymerizing monomers or a crosslinking polymer system) or subsequently with a preformed polymer having appropriate reactive functionality. Accordingly, due to such bonding, migration of these UV absorbers between layers of multi-layer coatings and into polymer substrates, or between coatings and their plastic substrates is greatly reduced.

Several of the previously incorporated references disclose bondable trisaryl-1,3,5-triazines. For example, previously incorporated U.S. Pat. No. 3423360, U.S. 4962142 and U.S. 5189084 disclose various bondable trisaryl-1,3,5-triazines and the incorporation of these compounds into polymers by chemical bonding. However, the inventors are unaware of any prior art which discloses the novel amido or carbamate containing trisaryl-1,3,5-triazines of the present invention.

SUMMARY OF THE INVENTION

The present invention provides a new class of bondable trisaryl-1,3,5-triazines in which an aryl ring attached to the triazine ring (and preferably an aryl ring containing a hydroxyl group or "latent" hydroxyl group ortho- to the point of attachment to the triazine ring) is substituted with a group comprising a bondable amido/carbamate containing group para- to the point of attachment to the triazine ring. More specifically, the new trisaryl-1,3,5-triazines of the present invention have the following general formulas (I), (IA), (II) and (III):

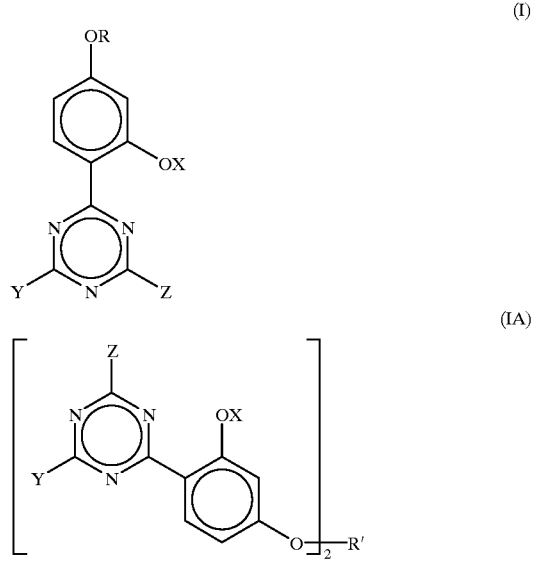

(II)

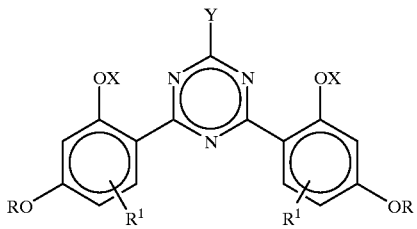

(III)

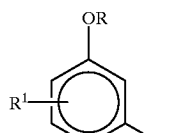

wherein
each X is independently selected from hydrogen and a blocking group; each of Y and Z is independently selected from an aryl ring of the general formula (IV)

(IV)

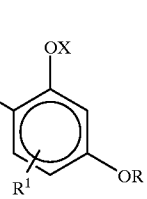

each R is independently selected from a hydrogen, a hydrocarbyl group and a functional hydrocarbyl group;
R' is selected from a divalent hydrocarbyl group and a functional divalent hydrocarbyl group;
each $R^1$, $R^2$, $R^4$, $R^{4'}$ and $R^{4''}$ is independently selected from hydrogen, hydrocarbyl, functional hydrocarbyl, —O(hydrocarbyl), —O(functional hydrocarbyl), —SR, halogen, —$SO_2R$, —$SO_3R$, —COOR, —COR, —OCOR, —NRR and cyano; and
each $R^3$ is independently selected from —R, —OR, —SR, halogen, —$SO_2R$, —$SO_3R$, —COOR, —COR, —NRR and cyano;
characterized in that at least one R group of a 4-position —OR group is selected from a group of the general formulas (V) ("amido group") and (VI) ("carbamate group")

(V)

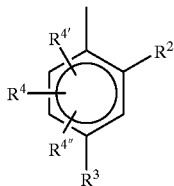

(VI)

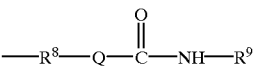

wherein
Q is selected from $NR^{10}$ and O;
$R^5$ is selected from a direct bond and a hydrocarbylene group;
$R^8$ is a hydrocarbylene group;
each $R^6$ and $R^7$ is independently selected from a hydrocarbyl group and a functional hydrocarbyl group, wherein at least one of $R^6$ and $R^7$ is a functional hydrocarbyl group; or
$R^6$ and $R^7$ taken together form a group selected from a functional hydrocarbylene group, an unsaturated hydrocarbylene group and an activated unsaturated hydrocarbylene group;
each $R^9$ is selected from hydrogen, a hydrocarbyl group and a functional hydrocarbyl group; and
$R^{10}$ is selected from hydrogen and a hydrocarbyl group.

The amido or carbamate containing tris-aryl-1,3,5-triazines of the present invention have the added benefit of being capable of being chemically bound to appropriate polymer systems via functionality attached to the amido or carbamate group (e.g., by a hydroxyl, ethylenic unsaturated and/or activated unsaturated group in one or more of $R^6$, $R^7$ or $R^9$) or, for a carbamate (formula (VI)) containing triazine, by direct bonding via the nitrogen atom of the carbamate group, especially if $R^9$ is hydrogen.

These trisaryl-1,3,5-triazines may in general be prepared via a number of procedures described in the previously incorporated references, but preferably by reacting a trisaryl-1,3,5-triazine precursor, having at least one aryl ring with a hydroxyl group para to the point of attachment to the triazine ring (and preferably hydroxyl groups both ortho and para to the point of attachment to the triazine ring), with an appropriate compound or compounds to functionalize the para position hydroxyl with a group of the above formula (V) or (VI). Further preferred process details are disclosed below.

The novel amido or carbamate containing trisaryl-1,3,5-triazines of the present invention are particularly useful as ultraviolet light absorber agents for stabilizing a wide variety of materials including, for example, organic compounds, oils, fats, waxes, cosmetics, dyes and biocides, and particularly various organic polymers (both crosslinked and non-crosslinked) used in applications such as photographic materials, plastics, rubbers, paints and other coatings, and adhesives, such as disclosed in a number of the previously incorporated references. The present invention, consequently, also relates to (1) a method of stabilizing a material which is subject to degradation by actinic radiation (e.g., an organic material such as an organic polymer in the form of a film, fiber or shaped article) by incorporating into said material an amount of an actinic radiation stabilizer composition effective to stabilize the material against the effects of actinic radiation, wherein the actinic radiation stabilizer composition comprises the inventive amido or carbamate containing trisaryl-1,3,5-triazine; and (2) the material so stabilized.

The novel amido or carbamate containing trisaryl-1,3,5-triazines of the present invention are also effective as ultraviolet light screening agents in applications such as sunscreens and other cosmetic preparations, capstock layers for extruded polymers, dyed fibers and laminated UV-screening window films, among others. The present invention, consequently, also relates (1) to a method of protecting a substrate against degradation by actinic radiation by applying to the substrate an actinic radiation screening layer (e.g., a coating film or capstock layer) containing an actinic radiation screening composition in an amount effective to reduce the amount of actinic radiation impinging on the substrate, wherein the actinic radiation screening composition comprises the inventive amido or carbamate containing trisaryl-1,3,5-triazines; and (2) the substrate so protected e.g., the actinic screening layer plus the substrate.

The novel trisaryl-1,3,5-triazines of the present invention may also employed to form light stabilizing compositions. Such light stabilizing compositions may include a variety of other components known in the art including other ultraviolet absorbers and stabilizers, antioxidants and the like.

These and other features and advantages of the present invention will be more readily understood by those of ordinary skill in the art from a reading of the following detailed description.

DETAILED DESCRIPTION OF THE PREFERRED EMBODIMENTS

The Amido or Carbamate Containing Trisaryl-1,3,5-Triazines

As indicated above, the trisaryl-1,3,5-triazines in accordance with the present invention are compounds of the general formulas (I), (II) and (III).

As used herein, the term "amido containing trisaryl-1,3,5-triazine" broadly refers to any compound of formulas (I), (II) or (III) wherein at least one R group of a 4-position OR group is an amido or amide group of the formula (V). As used herein, the term "carbamate containing trisaryl-1,3,5-triazine" broadly refers to any compound of formulas (I), (II) or (III) wherein at least one R group of a 4-position OR group is a carbamate group of the formula (VI).

The term "hydrocarbyl" in the context of the present invention, and in the above formulas, broadly refers to a monovalent hydrocarbon group in which the valency is derived by abstraction of a hydrogen from a carbon atom. Hydrocarbyl includes, for example, aliphatics (straight and branched chain), cycloaliphatics, aromatics and mixed character groups (e.g., aralkyl and alkaryl). Hydrocarbyl also includes such groups with internal unsaturation and activated unsaturation. More specifically, hydrocarbyl includes (but is not limited to) such groups as alkyl, cycloalkyl, aryl, aralkyl, alkaryl, alkenyl, cycloalkenyl and alkynyl, preferably having up to 24 carbon atoms. A hydrocarbyl may optionally contain a carbonyl group or groups (which is/are included in the carbon count) and/or a heteroatom or heteroatoms (such as at least one oxygen, sulfur, nitrogen or silicon), in the chain or ring.

The term "functional hydrocarbyl" in the context of the present invention, and in the above formulas, broadly refers to a hydrocarbyl possessing pendant and/or terminal "reactive" and/or "latent reactive" functionality and/or leaving groups. Reactive functionality refers to functionality which is reactive with common monomer/polymer functionality under normal conditions well understood by those persons of ordinary skill in the relevant art. As examples of reactive functionality may be mentioned active hydrogen containing groups such as hydroxyl, amino, carboxyl, thio, amido, carbamoyl and activated methylene; isocyanato; cyano; epoxy; ethylenically unsaturated groups such as allyl and methallyl; and activated unsaturated groups such acryloyl and methacryloyl, and maleate and maleimido (including the Diels-Alder adducts thereof with dienes such as butadiene).

Latent reactive functionality within the meaning of the present invention and, as would clearly be understood by those persons of ordinary skill in the relevant art, refers to reactive functionality which is blocked or masked to prevent premature reaction. As examples of latent reactive functionality may be mentioned ketimines and aldimines (amines blocked, respectively, with ketones and aldehydes); amine-carboxylate salts; and blocked isocyanates such as alcohol (carbamates), oxime and caprolactam blocked variations. A "leaving" group within the meaning of the present invention and, as would clearly be understood by those persons of ordinary skill in the relevant art, is a substituent attached to the hydrocarbyl chain or ring which during reaction is displaced to create a valency on a carbon or hetero atom in the hydrocarbyl chain or ring. As examples of leaving groups may be mentioned halogen atoms such as chlorine, bromine and iodine; quaternary ammonium salts ($NT_4^+$); sulfonium salts ($ST_3^+$); and sulfonates ($-OSO_3T$); where T is, e.g., methyl or para-tolyl. Preferred functionality includes hydroxyl, $-COOR^{11}$, $-CR^{12}=CH_2$, $-CO-CR^{12}=CH_2$, $OCO-CR^{12}=CH_2$, $-OCO-NH-R^9$, Cl,

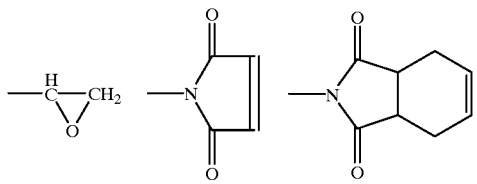

an isocyanate group, a blocked isocyanate group and $-NHR^{11}$ wherein $R^{11}$ is selected from hydrogen and a hydrocarbyl (preferably of up to 24 carbon atoms); and $R^{12}$ is selected from hydrogen and an alkyl of 1 to 4 carbon atoms (preferably hydrogen and methyl).

The term "hydrocarbylene" in the context of the present invention is a divalent hydrocarbon group in which both valencies derive by abstraction of hydrogens from carbon atoms. Included within the definition of hydrocarbylene are the same groups as indicated above for hydrocarbyl and functional hydrocarbyl with, of course, the extra valency (for example, alkylene, alkenylene, arylene, alkylaryl, etc.).

The term "functional hydrocarbylene" in the context of the present invention refers to a species of hydrocarbylene possessing pendant reactive functionality, latent reactive functionality and/or leaving groups. The term "nonfunctional hydrocarbylene" in the context of the present invention refers generally to a hydrocarbylene other than a functional hydrocarbylene.

The trisaryl-1,3,5-triazines in accordance with the present invention also relate to latent stabilizing compounds against actinic radiation of the general formulas (I), (II) and (III), wherein at least one of the hydroxyl groups on an aryl ring ortho to the point of attachment to the triazine ring is blocked, that is, wherein at least one X is other than hydrogen. Such latent stabilizing compounds liberate the effective stabilizers by cleavage of the O—X bond, e.g., by heating or by exposure to UV radiation. Latent stabilizing compounds are desirable because they have many favorable properties, i.e., good substrate compatibility, good color properties, a high conversion of the O—X group to an OH group, and a long shelf life. The use of latent stabilizing compounds is further described in U.S. Pat. No. 4775707, U.S. 5030731, U.S. 5563224 and U.S. 5597854, which are incorporated herein for all purposes as if fully set forth.

Latent stabilizing compounds comprising the amido or carbamate containing trisaryl-1,3,5-triazines in accordance with the present invention can be prepared from compounds of the general formulas (I), (II) and (III) wherein at least one X is hydrogen by subjecting said compounds to a further reaction to form latent stabilizing compounds, as described in the immediately preceding incorporated references.

As preferred examples of blocking groups X may be mentioned one or more of the following groups: allyl, —$COR^a$, —$SO_2R^b$, —$SiR^cR^dR^e$, or —$CONHR^h$, wherein each $R^a$ is independently selected from $C_1$–$C_8$ alkyl, halogen-substituted $C_1$–$C_8$ alkyl, $C_5$–$C_{12}$ cycloalkyl, $C_2$–$C_8$ alkenyl, —$CH_2$—CO—$CH_3$, $C_1$–$C_{12}$ alkoxy, and phenyl or phenoxy which is unsubstituted or substituted by $C_1$–$C_{12}$ alkyl, $C_1$–$C_4$ alkoxy, halogen and/or benzyl;

each $R^b$ is independently selected from $C_1$–$C_{12}$ alkyl, $C_6$–$C_{10}$ aryl and $C_7$–$C_{18}$ alkylaryl;

each $R^c$, $R^d$ and $R^e$ is independently selected from $C_1$–$C_{18}$ alkyl, cyclohexyl, phenyl and $C_1$–$C_{18}$ alkoxy;

each $R^f$ and $R^g$ is independently selected from $C_1$–$C_{12}$ alkoxy, $C_1$–$C_{12}$ alkyl, $C_5$–$C_{12}$ cycloalkyl, and phenyl or phenoxy which is unsubstituted or substituted by $C_1$–$C_{12}$ alkyl, $C_1$–$C_4$ alkoxy, halogen and/or benzyl; and each $R^h$ is independently selected from $C_1$–$C_8$ alkyl, $C_5$–$C_{12}$ cycloalkyl, $C_2$–$C_8$ alkenyl, —$CH_2$—CO—$CH_3$, and phenyl which is unsubstituted or substituted by $C_1$–$C_{12}$ alkyl, $C_2$–$C_8$ alkenyl, $C_1$–$C_4$ alkoxy, halogen and/or benzyl.

The reaction to give the latent stabilizing compounds of the present invention of the general formulas (I), (II) and (III) in which X is allyl, —$COR^a$, —$SO_2R^b$, —$SiR^cR^dR^e$, —$PR^fR^g$ or —$POR^fR^g$ can be carried out, for example, by reaction of the compounds of the general formulas (I), (II) and (III) wherein at least one X is hydrogen with the corresponding halides such as allyl chloride, Cl—$COR^a$, Cl—$SO_2R^b$, Cl—$SiR^cR^dR^e$, or Cl—$POR^fR^g$. The reaction to give the latent stabilizing compounds of the present invention of the general formulas (I), (II) and (III) in which X is —$CONHR^h$ can be carried out, for example, by reaction of the compounds of the general formulas (I), (II) and (III) wherein at least one X is hydrogen with the corresponding isocyanates. Furthermore, acylated compounds can be obtained by reaction with anhydrides, ketenes or esters, such as lower alkyl esters, as is well known to one skilled in the art. The above-described reagents may be used in approximately equimolar amounts or in excess, for example, from 2 to 20 mol with respect to the hydroxyl groups desired to be made latent in the starting compound of the general formula (I), (II) or (III).

Catalysts customarily used for acylation, sulfonylation, phosphorylation, silylation or urethanation reactions may be used in forming the latent stabilizing amido or carbamate containing trisaryl-1,3,5-triazines of the present invention. For example, acylation and sulfonylation reaction catalysts such as tertiary or quaternary amines, such as triethylamine, dimethylaminopyridine or tetrabutylammonium salts, may be used for forming these latent stabilizing compounds.

The reaction may be carried out in the presence of a solvent, such as relatively inert organics, e.g., hydrocarbons such as toluene and xylene, chlorinated hydrocarbons such as carbon tetrachloride or chloroform, or ethers such as tetrahydrofuran or dibutyl ether, or without a solvent. Alternatively, the reagent(s) may be employed as the solvent. The reaction temperature is usually between room temperature and about 150° C., for example, up to the boiling point of the solvent when a solvent is used.

In preferred embodiments, each X is hydrogen.

In preferred embodiments, those R groups which are not either a group of the formula (V) or (VI) are independently selected from hydrogen, a hydrocarbyl group of 1 to 24 carbon atoms; and a functional hydrocarbyl group of 1 to 24 carbon atoms. More preferably each such R group is independently selected from hydrogen, an alkyl of 1 to 24 carbon atoms (which may optionally be substituted by one or more hydroxyl, carboxyl, carboalkoxy (ester) amide, epoxy and/or amino groups and/or contain one or more carbonyl groups, oxygen atoms and/or nitrogen atoms in the chain); an alkenyl of 2 to 24 carbon atoms (which may optionally be substituted by hydroxyl, carboxyl, epoxy and/or amino group(s) and/or contain carbonyl, oxygen and/or nitrogen in the chain), a cycloalkyl of 5 to 24 carbon atoms (which may optionally be substituted by hydroxyl, carboxyl and/or amino group(s) and/or contain carbonyl, oxygen and/or nitrogen in the ring), and an aralkyl of 7 to 24 carbon atoms (which may optionally be substituted by hydroxyl, carboxyl and/or amino group(s) and/or contain carbonyl, oxygen and/or nitrogen in the ring).

More preferably, each R group is independently selected from hydrogen, an alkyl of 1 to 24 carbon atoms optionally containing an oxygen atom in the chain, a hydroxyalkyl of 1 to 24 carbon atoms group optionally containing an oxygen atom in the chain, a group of the formula (V) and a group of the formula (VI), with the proviso that at least one such R group is a group of the formula (V) or (VI).

In preferred embodiments, each $R^1$ is independently selected from hydrogen, halogen, an acyl of 2 to 12 carbon atoms, an acyloxy of 2 to 12 carbon atoms, a hydrocarbyl having from 1 to 24 carbon atoms and a functional hydrocarbyl having from 1 to 24 carbon atoms; more preferably from hydrogen, halogen, an alkyl of 1 to 24 carbon atoms, a functional alkyl of 1 to 24 carbon atoms, an alkenyl of 2 to 24 carbon atoms, a cycloalkyl of 5 to 12 carbon atoms; and especially hydrogen.

In preferred embodiments, each $R^2$ is independently selected from hydrogen, halogen, a hydrocarbyl group of 1 to 24 carbon atoms, a hydrocarbyloxy group of 1 to 24 carbon atoms, an acyl group of 2 to 24 carbon atoms and an acyloxy group of 2 to 24 carbon atoms. More preferably, each $R^2$ is independently selected from hydrogen, halogen, an alkyl of 1 to 24 carbon atoms optionally containing an oxygen atom in the chain; an alkyloxy of 1 to 24 carbon atoms optionally containing an oxygen atom in the chain; an alkenyl of 2 to 24 carbon atoms optionally containing an oxygen atom in the chain; an alkenyloxy of 2 to 24 carbon atoms optionally containing an oxygen atom in the chain; and an acyloxy group of 2 to 12 carbon atoms. Still more preferably, each $R^2$ is independently selected from hydrogen, an alkyl of 1 to 8 carbon atoms, an alkyloxy of 1 to 8 carbon atoms optionally containing an oxygen atom in the chain, a hydroxyalkyl of 1 to 8 carbon atoms group optionally containing an oxygen atom in the chain, a hydroxyalkyloxy of 1 to 8 carbon atoms group optionally containing an oxygen atom in the chain, and an acyloxy of 2 to 12 carbon atoms. Especially preferred is when each n is independently selected from hydrogen and an alkyl of 1 to 4 carbon atoms and particularly hydrogen and methyl.

In preferred embodiments, each $R^3$ is independently selected from hydrogen, halogen, a hydrocarbyl group of 1 to 24 carbon atoms, a functional hydrocarbyl group of 1 to 24 carbon atoms and —OR. More preferably, each $R^3$ is independently selected from hydrogen, an alkyl of 1 to 24 carbon atoms (which may optionally be substituted by hydroxyl, carboxyl and/or amino group(s) and/or contain carbonyl, oxygen and/or nitrogen in the chain); an alkenyl of 2 to 24 carbon atoms (which may optionally be substituted by hydroxyl, carboxyl and/or amino group(s) and/or contain carbonyl, oxygen and/or nitrogen in the chain); a cycloalkyl of 5 to 12 carbon atoms (which may optionally be substituted by hydroxyl, carboxyl and/or amino group(s) and/or contain carbonyl, oxygen and/or nitrogen in the ring); and —OR. Still more preferably, each $R^3$ is independently selected from hydrogen, an alkyl of 1 to 24 carbon atoms optionally containing an oxygen atom in the chain, a hydroxyalkyl of 1 to 24 carbon atoms group optionally containing an oxygen atom in the chain and —OR. Especially preferred is when each $R^3$ is independently selected from hydrogen, an alkyl of 1 to 4 carbon atoms and —OR; particularly hydrogen, methyl and —OR; and most particularly hydrogen and methyl.

In preferred embodiments, each $R^4$, $R^4$ and $R^4$ is independently selected from hydrogen, a hydrocarbyl group of 1 to 24 carbon atoms, a hydrocarbyloxy group of 1 to 24 carbon atoms, an acyl group of 2 to 24 carbon atoms and an acyloxy group of 2 to 24 carbon atoms. More preferably, each $R^4$, $R^4$ and $R^4$ is independently selected from hydrogen, an alkyl of 1 to 24 carbon atoms optionally containing an oxygen atom in the chain; an alkyloxy of 1 to 24 carbon atoms optionally containing an oxygen atom in the chain; an alkenyl of 2 to 24 carbon atoms optionally containing an oxygen atom in the chain; an alkenyloxy of 2 to 24 carbon atoms optionally containing an oxygen atom in the chain; an acyl group of 2 to 12 carbon atoms; and an acyloxy group of 2 to 12 carbon atoms. Still more preferably, each $R^4$, $R^4$ and $R^4$ is independently selected from hydrogen, an alkyl of 1 to 8 carbon atoms, an alkyloxy of 1 to 8 carbon atoms optionally containing an oxygen atom in the chain, a hydroxyalkyl of 1 to 8 carbon atoms group optionally containing an oxygen atom in the chain, a hydroxyalkyloxy of 1 to 8 carbon atoms group optionally containing an oxygen atom in the chain, an acyl group of 2 to 12 carbon atoms and an acyloxy of 2 to 12 carbon atoms. Especially preferred is when each $R^4$, $R^4$ and $R^4$ is independently selected from hydrogen and an alkyl of 1 to 4 carbon atoms, and particularly hydrogen and methyl.

In preferred embodiments, each of $R^5$ and $R^8$ is independently a hydrocarbylene group of 1 to 24 carbon atoms. More preferably, each of $R^5$ and $R^8$ is independently selected from an alkylene of 1 to 24 carbon atoms (which may optionally contain carbonyl and/or oxygen in the chain); an alkenylene of 2 to 24 carbon atoms (which may optionally contain carbonyl and/or oxygen in the chain) and a cycloalkylene of 5 to 12 carbon atoms (which may optionally contain carbonyl and/or oxygen in the ring). Still more preferably, each of $R^5$ and $R^8$ is independently an alkylene of 1 to 24 carbon atoms optionally containing an oxygen atom in the chain and especially an alkylene of 2 to 18 carbon atoms optionally containing an oxygen in the chain.

In preferred embodiments, each of $R^6$ and $R^7$ is independently selected from a hydrocarbyl group of 1 to 50 carbon atoms and a functional hydrocarbyl group of 1 to 50 carbon atoms, with at least one (and preferably only one) of $R^6$ and $R^7$ being such a functional hydrocarbyl group. As preferred examples of functionality for the functional hydrocarbyl groups may be mentioned hydroxyl, epoxy, —COOR$^{11}$, —CR$^2$=CH$_2$, —CO—CR$^{12}$=CH$_2$, —OCO—CR$^{12}$=CH$_2$, —OCO—NH—R$^9$, —NHR$^{11}$ and a blocked isocyanate group. More preferably, each of $R^6$ and $R^7$ is independently selected from an alkyl group of 1 to 24 carbon atoms (which may optionally contain carbonyl and/or one or more oxygen atoms in the chain); an alkenyl group of 2 to 24 carbon atoms (which may optionally contain carbonyl and/or one or more oxygen atoms in the chain); a cycloalkyl group of 5 to 12 carbon atoms (which may optionally contain carbonyl and/or one or more oxygen atoms in the ring); and an aralkyl group of 7 to 24 carbon atoms, at least one of which groups is substituted with a functional group as described above. Still more preferably, each of $R^6$ and $R^7$ is independently selected from an alkyl group of 1 to 24 carbon atoms (which may optionally contain carbonyl and/or one or more oxygen atoms in the chain), and an aralkyl group of 7 to 24 carbon atoms, and at least one of which is substituted by a hydroxyl, —CR$^{12}$=CH$_2$, —CO—CR$^{12}$=CH$_2$, —OCO—CR$^{12}$=CH$_2$, —NHR$^{11}$ and a blocked isocyanate group.

In another preferred embodiment, $R^6$ and $R^7$ taken together form a group selected from a functional hydrocarbylene group having 3 to 24 carbon atoms, an unsaturated hydrocarbylene group having 3 to 24 carbon atoms and an activated unsaturated hydrocarbylene group having 3 to 24 carbon atoms. More preferable, $R^8$ and $R^7$ taken together form a group selected from an unsaturated hydrocarbylene group having 4 to 14 carbon atoms and an activated unsaturated hydrocarbylene group having 4 to 14 carbon atoms. As specific examples of $R^6$ and $R^7$ taken together, in combination with the nitrogen, may be mentioned maleimide, citraconimide, itaconimide, and the Diels-Alder adducts of maleimide with dienes.

In preferred embodiments, $R^9$ is selected from hydrogen, a hydrocarbyl group of 1 to 50 carbon atoms and a functional hydrocarbyl group of 1 to 50 carbon atoms. More preferably, $R^9$ is selected from hydrogen, an alkyl of 1 to 24 carbon atoms (which may optionally be substituted by a hydroxyl, and/or contain carbonyl, oxygen and/or nitrogen in the chain); an alkenyl of 2 to 24 carbon atoms (which may optionally be substituted by a hydroxyl and/or contain carbonyl, oxygen and/or nitrogen in the chain); a cycloalkyl of 5 to 12 carbon atoms (which may optionally be substituted by a hydroxyl and/or contain carbonyl, oxygen and/or nitrogen in the ring); and an aralkyl of 7 to 24 carbon atoms (which may optionally be substituted with a hydroxyl, —CR$^{12}$=CH$_2$ or —CO—CR$^{12}$=CH$_2$). Still more preferably, $R^9$ is selected from hydrogen, an alkyl of 1 to 24 carbon atoms optionally containing an oxygen atom in the chain, and an aralkyl of 7 to 24 carbon atoms, which may optionally be substituted with a hydroxyl, —CR$^{12}$=CH$_2$ or —CO—CR$^{12}$=CH$_2$. Especially preferred is when $R^9$ is selected from hydrogen, an alkyl of 1 to 12 carbon atoms and an aralkyl of 7 to 24 carbon atoms optionally substituted with —CR$^{12}$=CH$_2$.

In preferred embodiments, $R^{10}$ is hydrogen or an alkyl of 1 to 24 carbon atoms, which may optionally contain oxygen in the chain, and more preferably hydrogen.

In preferred embodiments, $R^{11}$ is selected from hydrogen and hydrocarbyl of 1 to 24 carbon atoms which may optionally be substituted by hydroxyl or alkoxy of 1 to 4 carbon atoms and/or contain one or more oxygen and/or nitrogen atoms in the chain. More preferably, $R^{11}$ is selected from hydrogen and hydrocarbyl of 1 to 24 carbon atoms which may optionally be substituted by hydroxyl or alkoxy of 1 to 4 carbon atoms.

In preferred embodiments, $R^{12}$ is selected from hydrogen and an alkyl of 1 to 4 carbon atoms. More preferably, $R^{12}$ is selected from hydrogen and a methyl group.

In preferred embodiments, $R^{13}$ is selected from hydrogen, a hydrocarbyl group of 1 to 8 carbon atoms, or phenyl. More preferably, $R^{13}$ is hydrogen or methyl.

Further preferred embodiments may include any combination of the parameters mentioned above.

Particularly preferred embodiments of the trisaryl-1,3,5-triazines of the general formula (I) are exemplified by the following structures (VII), (VIII) and (IX):

(VII)

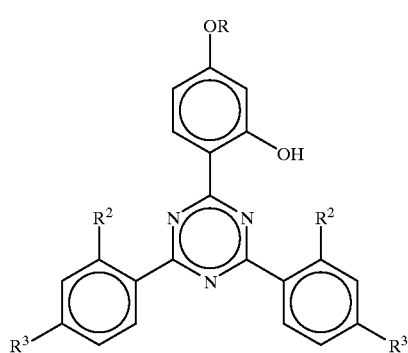

(VIII)

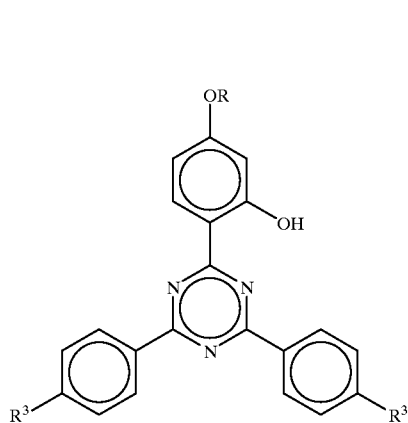

(IX)

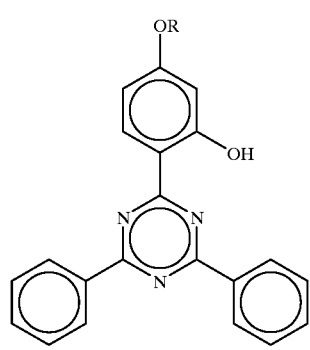

Particularly preferred embodiments of the trisaryl-1,3,5-triazines of the general formula (II) are exemplified by the following structures (X), (XI) and (XII):

(X)

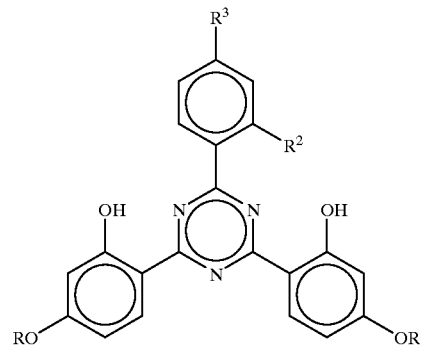

(XI)

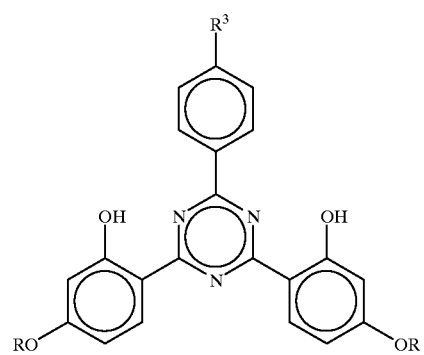

(XII)

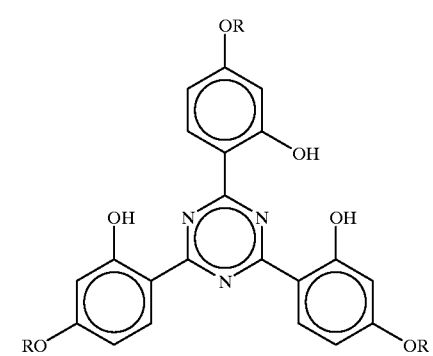

Particularly preferred embodiments of the trisaryl-1,3,5-triazines of the general formula (III) are exemplified by the following structures (XIII) and (XIV):

(XIII)

-continued (XIV)

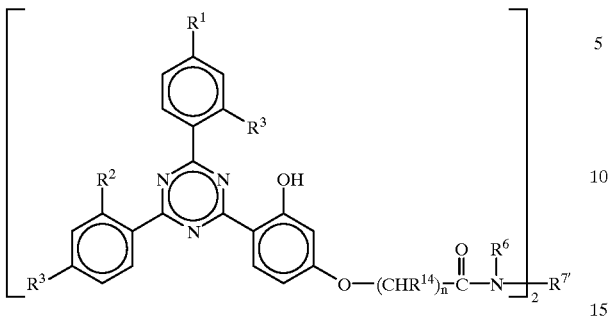

Preferred embodiments of groups of the general formula (V) are those wherein $R^5$ is —$(CHR^{14})_n$—;

$R^6$ and $R^7$ are each independently selected from the group consisting of hydrogen, linear or branched alkyl of 1 to 24 carbon atoms, —$(CH_2)_nOH$, —$(CH_2)CH(OH)CH_2OR^{15}$, —$(CH_2)CH(OH)CH_2R^{15}$ and

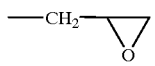

$R^{14}$ and $R^{15}$ are each independently selected from hydrogen or linear or branched alkyl of 1 to 24 carbon atoms.

Other preferred embodiments of groups of the general formula (V) are those wherein $R^5$ is —$(CHR^{14})_n$—;

$R^6$ is selected from the group consisting of hydrogen, linear or branched alkyl of 1 to 24 carbon atoms, —$(CH_2)_nOH$, —$(CH_2)CH(OH)CH_2OR^{15}$, —$(CH_2)CH(OH)CH_2R^{15}$ and

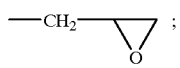

and $R^7$ is selected from the group consisting of a polyoxyalkylene radical of the formula —$CH_2CH(OH)CH_2O(CH_2(CH_2)_mO)_p$—D in which D is hydrogen,

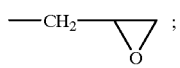

—$CH_2CH(OH)CH_2OH$ or $R^{16}$;

a polyoxyalkylene radical of the formula

—$CO(CH_2)_mO(CH_2(CH_2)O)_p$—$D_2$ in which $D_2$ is —$(CH2)_mCOR^{17}$ or $R^{16}$;

a polyoxyalkylene radical of the formula

—$TOCO(CH_2)_mO(CH_2(CH_2)O)_p$—$D_3$ in which $D_3$ is —$(CH_2)_mCOR^{17}$ or $R^{16}$;

a polyoxyalkylene radical of the formula

—$(CH_2)_qCH(R^{18})COB_1(C_rH_{2r}O)_p$—$C_rH_{2r}D_4$ in which $D_4$ is hydrogen or $R^{16}$;

a polyoxyalkylene radical of the formula

—$COCH_2CH_2NH(C_rH_{2r}O)_p$—$C_rH_{2r}D_5$ in which $D_5$ is —$NH_2$, —$NH(CH_2)_2COOR^{19}$ or or $R^{16}$;

a polyoxyalkylene radical of the formula

—$TOCOCH_2CH_2NH(C_rH_{2r}O)_p$—$C_rH_{2r}D_5$ in which $D_5$ is —$NH_2$, —$NH(CH_2)_2COOR^{19}$ or or $R^{16}$;

a polyoxyalkylene radical of the formula $(C_rH_{2r}O)_p$—$CH_2D_6$ in which $D_6$ is —$NHCOR^{20}$, —OH or hydrogen; or a polyoxyalkylene radical of the formula —$CH(R^{21})CH_2(OCH(R^{21})CH_2)_p$—$D_7$ in which $D_7$ is $OR^{16}$, —$NHCOR^{20}$ or —$OCH_2CH_2OR^{20}$.

Other preferred embodiments are dimeric trisaryl-1,3,5-triazines of formula (XIV) wherein $R^6$ is selected from the group consisting of hydrogen, linear or branched alkyl of 1 to 24 carbon atoms, —$(CH_2)_nOH$, —$(CH_2)CH(OH)CH_2OR^{15}$, —$(CH_2)CH(OH)CH_2R^{15}$ and

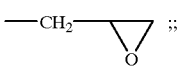

and $R^{7'}$ is a selected from the group consisting of alkylene of 2 to 24 carbon atoms, alkenylene of 2 to 12 carbon atoms, xylylene and alkylene of 3 to 24 atoms which is interrupted by one or more oxygen atoms or substituted by —OH;

or a diradical of formula (XV)

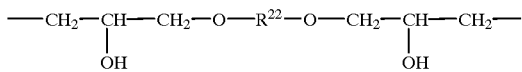

wherein $R^{22}$ is selected from alkylene of 2 to 10 carbon atoms and alkylene of 4 to 50 carbon atoms which is interrupted by one or more oxygen atoms or substituted by —OH;

or is a polyoxyalkylene bridge of the formula

—$CH_2CH(OH)CH_2O(CH_2(CH_2)_mO)_pCH_2CH(OH)CH_2$—;

or a polyoxyalkylene bridge of the formula

—$CO(CH_2)_mO(CH_2(CH_2)_mO)_p(CH_2)_mCO$—;

or is a polyoxyalkylene bridge of the formula

—$TOCO(CH_2)_mO(CH_2(CH_2)_mO)_p(CH_2)_mCOOT$—;

or a polyoxyalkylene bridge of the formula $(CH_2)_qCHR^{23}COB_1(C_rH_{2r}O)_p$—$C_rH_{2r}B_1COCHR^{23}(CH_2)_q$—;

or a polyoxyalkylene bridge of the formula

—COCH($R^{24}$)($CH_2$)NH($C_rH_{2r}$O)p-$C_rH_{2r}$NH$CH_2$CH($R^{24}$)CO—;

or a polyoxyalkylene bridge of the formula

—TOCO($CH_2$)$_2$NH($C_rH_{2r}$O)p-$C_rH_{2r}$NH($CH_2$)$_2$COOT—;

or a polyoxyalkylene bridge of the formula

—($C_rH_{2r}$O)p-$C_rH_{2r}$—;

or a polyoxyalkylene bridge of the formula

—CH($CH_3$)$CH_2$(OCH($CH_3$)$CH_2$)$_a$(O$CH_2CH_2$)$_b$(O$CH_2$CH($CH_3$))$_c$—;

in which a+c=2.5 and b=8.5 to 40.5, or a+c=2 to 33 and b=0.

Wherein $R^{16}$ is alkyl of 1 to 18 carbon atoms;

$R^{17}$ is halogen or $R^{19}$;

$R^{18}$ is hydrogen or alkyl of 1 to 18 carbon atoms;

$R^{19}$ is hydrogen, alkyl of 1 to 18 carbon atoms, alkenyl of 3 to 18 carbon atoms, aryl of 6 to 18 carbon atoms or aralkyl of 7 to 18 carbon atoms;

$R^{20}$ is hydrogen, alkyl of 1 to 12 carbon atoms or aryl of 6 to 12 carbon atoms;

$R^{21}$ is hydrogen or alkyl of 1 to 4 carbon atoms;

$R^{23}$ is hydrogen or alkyl of 1 to 16 carbon atoms;

$R^{24}$ is hydrogen, alkyl of 1 to 4 carbon atoms or CN;

m is a number from 1 to 4;

p is a number from 2 to 60;

q is zero or a number from 1 to 16;

r is 2 to 6;

$B_1$ is a bridging group selected from —O—, —NH— or —$NR^{18}$—;

and

T is unsubstituted or substituted alkylene of 2 to 20 carbon atoms.

Particularly preferred embodiments of groups of the general formula (V) include the following:

wherein n is 1–24 (preferably 1–18, and especially 1–8), n1 is 0–23 (preferably 0 to 17), n2 is 1–24 (preferably 1–10) and n3 is 1–24 (preferably 1 to 8).

Particularly preferred embodiments of groups of the general formula (VI) include the following:

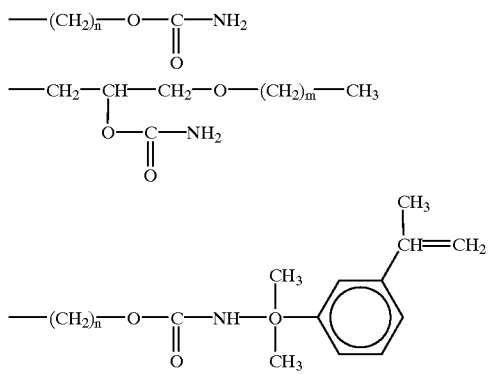

wherein n and n1 are as defined above.

Methods of Preparation

The amido or carbamate containing trisaryl-1,3,5-triazines of the present invention can be prepared by a multistep process in which a 4-hydroxyl precursor is appropriately functionalized, by analogy to the procedures described in a number of the previously incorporated references such as U.S. Pat. No. 3,244,708 and EP-A-0434608.

In a preferred method for preparing the amido functional triazine compounds, a precursor compound corresponding to the formulas (I), (II) or (III), except where at least one (and preferably all) R groups are hydrogen, is reacted in a first step with a haloacetate (e.g., ethyl chloroacetate) to prepare an acetate functional intermediate, which is subsequently reacted with an appropriate secondary amine to prepared the desired amido functional end product.

The reaction of the precursor compound with the haloacetate may be conducted under appropriate acylating conditions known to those of ordinary skill in the art. Preferably, the reaction is carried out in the presence of an inert solvent, such as acetonitrile, acetone, methyl ethyl ketone, methyl isobutyl ketone, dimethylformamide, dioxane, tetrahydrofuran, and aromatic hydrocarbons such as toluene and xylene. The reaction is also preferably carried out in the presence of a catalyst such as an alkali metal iodide like sodium or potassium iodide. A base is also preferably present, such as an alkali metal hydroxide (sodium or potassium hydroxide), alkali metal carbonate or bicarbonate, or tertiary amine (triethylamine). Reaction temperatures may vary widely depending on the starting components; however, temperatures of 100° C. or less are preferred to avoid undesired reaction of the 2-hydroxyl group.

The reaction of the resulting acetate functional intermediate with the secondary amine is preferably carried out under appropriate transesterification/amidation conditions known to those of ordinary skill in the art. Preferably, the reaction is carried out in the presence of a solvent as set forth above, and further in the presence of a transesterification/amidation catalyst. Examples of suitable transesterification/amidation catalysts include the titanates such as tetra-i-propyltitanate (TYZOR® TPT) (titanium (IV) isoproxide) tetrabutyltitanate (TYZOR® TBT) (titanium (IV) butoxide), alkali and alkaline earth salts of β-ketoesters and β-diketones such as calcium and magnesium salts of acetoacetic acid, alkoxides and oxides of alkali and alkaline earth metals such as sodium, potassium, calcium and magnesium, tertiary amines such as 4-dimethylaminopyridine), and strong protonic acids such as $H_2SO_4$, HCl and p-toluenesulfonic acid, which may optionally be supported on inert supports, and transition metal salts such as zinc, nickel, copper or cobalt acetate. The reaction is preferably carried out under reflux conditions, with the removal of volatile alcohol by-products.

In another preferred process for preparing the amido functional compounds in accordance with the present invention, the precursor compound mentioned above (wherein the R groups are H) can be reacted in a first step with a hydroxyalkyl halide (under conditions well-known to those of ordinary skill in the art) to prepare a hydroxyalkyl functional intermediate, which is subsequently reacted with the haloacetate and secondary amine as described above.

Another preferred process is a variation on the above-described processes, in which the precursor compound mentioned above is reacted with a pre-react of the above mentioned functionalizing reactants (varying the order of reaction) for example, preparing a pre-react of an haloacetate and secondary amine, then reacting this pre-react further with the precursor compound.

The carbamate functional compounds in accordance with the present invention are also preferably prepared by reacting the aforementioned hydroxyalkyl functional intermediate with an isocyanate functional compound such as 1-(2-isocyanatoisopropyl)-3-isopropenylbenzene ("m-TMI"), or a blocked isocyanate functional compound such as methyl carbamate (transcarbamylation). This reaction is preferably carried out in an inert solvent such as xylene, and further in the presence of a well-known urethane base or organometallic catalyst.

The resulting amido and carbamate functional compounds may be further functionalized if and as desired. For example, in the preparation of the amide functional triazine compound, the use of an hydroxyalkyl amine as the secondary amine results in a hydroxyalkyl functional amide. The hydroxyl group may be further reacted with, for example, an unsaturated acid such as (meth)acrylic acid, a halo compound such as allyl chloride, an epoxy functional compound such as ethylene or propylene oxide, and/or an isocyanate functional compound such a m-TMI, to impart other or additional functionality to the molecule.

Specific preferred preparative procedures are detailed in the examples annexed hereto.

Uses of the Trisaryl-1,3,5-Triazines

As indicated earlier, the novel amido and carbamate containing trisaryl-1,3,5-triazines of the present invention are particularly useful as ultraviolet light absorber agents for stabilizing a wide variety of materials including, for example, various polymers (both crosslinked and thermoplastic), photographic materials and dye solutions for textile materials, as well as in ultraviolet light screening agents (such as sunscreens). The novel amido or carbamate containing trisaryl-1,3,5-triazines of the present invention can be incorporated into such material in any one of a variety of conventional manners, including, for example, physical mixing or blending, optionally, with chemical bonding to the material (typically to a polymer), as a component in a light stabilizing composition such as a coating or solution, or as a component in a UV screening composition such as a sunscreen composition.

In one embodiment of the present invention, the amido or carbamate containing trisaryl-1,3,5-triazines of the present invention can be employed to stabilize materials which are subject to degradation by ultraviolet radiation by incorporating the presently claimed compounds into such materials, especially organic polymers, either chemically or physically.

Examples of polymers which can be stabilized include, but are not limited to:

1. Homo- and copolymers of monoolefins and diolefins including but not limited to ethylene, propylene, isobutylene, butene, methylpentene, hexene, heptene, octene, isoprene, butadiene, hexadiene, dicyclopentadiene, ethylidene and cycloolefins such as cyclopentene and norbornene; for example, polyethylenes (which optionally can be crosslinked) such as high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE) and branched low density polyethylene (BLDPE).
2. Copolymers of one or more monoolefins and/or diolefins with carbon monoxide and/or with other vinyl monomers, including limited acrylic and methacrylic acid, acrylates and methacrylates, acrylamides, acrylonitriles, styrenes, vinyl acetate (such as ethylene/vinyl acetate copolymers), vinyl halides, vinylidene halides, maleic anhydride and allyl monomers such as allyl alcohol, allyl amine ally glycidyl ether and derivatives thereof.
3. Hydrocarbon resins (such as $C_5$–$C_9$) including hydrogenated modifications thereof and mixtures of polyalkylenes and starch.
4. Homo- and copolymers of styrenes such as styrene, p-methylstyrene and amethyistyrene.
5. Copolymers of one or more styrenes with other vinyl monomers such as olefins and diolefins (e.g., ethylene, isoprene and/or butadiene), acrylic and methacrylic acid, acrylates and methacrylates, acrylamides, acrylonitriles, vinyl acetate (such as ethylene/vinyl acetate copolymers), vinyl halides, vinylidene halides, maleic anhydride and allyl compounds such as allyl alcohol, allyl amine allyl glycidyl ether and derivatives thereof.
6. Graft copolymers of styrenes on polybutadienes, polybutadiene/styrene copolymers and polybutadiene/acrylonitrile copolymers; styrene (or a-methylstyrene) and acrylonitrile (or methacrylonitrile) on polybutadiene; styrene and maleic anhydride on polybutadiene; styrene, acrylonitrile and maleic anhydride or maleimide on polybutadiene; styrene and acrylonitrile on ethylene/propylene/diene copolymers; styrene and acrylonitrile on polyalkyl acrylates or methacrylates; and styrene and acrylonitrile on acrylate/butadiene copolymers.
7. Halogen-containing polymers such as polychloroprene; chlorinated rubbers; chlorinated and brominated isobutylene/isoprene copolymers; chlorinated or sulfochlorinated polyethylene; copolymers of ethylene and chlorinated ethylene; epichlorohydrin polymers and copolymers; and polymers and copolymers of halogen-containing vinyl compounds such as vinyl chloride, vinylidene chloride, vinyl fluoride and/or vinylidene fluoride and other vinyl monomers.
8. Homo- and copolymers derived from α,β-unsaturated acids and derivatives thereof such as acrylic acid, methacrylic acid, acrylates, methacrylates, acrylamides and acrylonitriles.
9. Copolymers of the monomers mentioned in (8) with other unsaturated monomers such as olefins and diolefins (e.g., butadiene), styrenes, vinyl halides, maleic anhydride and allyl monomer such as allyl alcohol, allyl amine, allyl glycidyl ether and derivatives thereof
10. Homo- and copolymers derived from unsaturated alcohols and amines or the acyl derivatives or acetals thereof, such as vinyl alcohol, vinyl acetate, vinyl stearate, vinyl benzoate, vinyl maleate, vinyl butyral, allyl alcohol, allyl amine, allyl glycidyl ether, allyl phthalate and allyl melamine; as well as copolymers of such monomers with other ethylenically unsaturated monomers mentioned above.
11. Homo- and copolymers of cyclic ethers such as alkylene glycols and alkylene oxides, as well as copolymers with bisglycidyl ethers.
12. Polyacetals such as polyoxymethylene and those polyoxymethylenes which contain ethylene oxide as a comonomer; and polyoxymethylenes modified with thermoplastic polyurethanes, acrylates and/or MBS.
13. Polyphenylene oxides and sulfides.
14. Polyurethanes derived from hydroxy-functional components such as polyhydric alcohols, polyethers, polyesters, polyacrylics and/or polybutadienes on the one hand, and aliphatic and/or aromatic isocyanates on the other, as well as precursors thereof.
15. Polyamides and copolyamides derived from diamines, dicarboxylic acids and/or aminocarboxylic acids or the corresponding lactams, such as polyamide 4, polyamide 6, polyamide 6/6, polyamide 6/10, polyamide 6/9, polyamide 6/12, polyamide 4/6, polyamide 12/12, polyamide 11 and polyamide 12; aromatic polyamides starting from m-xylene diamine and adipic acid; polyamides prepared from hexamethylene diamine and isophthalic and/or terephthalic acid and with or without an elastomer as a modifier, for example, poly-2,4,4-trimethylhexamethylene terephthalamide or poly-m-phenylene isophthalamide; block copolymers of the aforementioned polyamides with polyolefins, olefin copolymer, ionomers, chemically bonded or grafted elastomers, or polyethers such as polyethylene glycol, polypropylene glycol or polytetramethylene glycol; and polyamides condensed during processing (RIM polyamide systems).
16. Polyureas, polyimides, polyamide-imides, polyetherimides, polyesterimides, polyhydantoins and polybenzimidazoles.
17. Polyesters derived from dicarboxylic acids, diols and/or hydroxycarboxylic acids or the corresponding lactones, such as polyethylene terephthalate, polybutylene terephthalate, poly-1,4-dimethylcyclohexane terephthalate and polyhydroxybenzoates, as well as block copolyether esters derived from hydroxylterminated ethers; and also polyesters modified with polycarbonate or MBS.
18. Polycarbonates and polyester carbonates.
19. Polysulfones, polyether sulfones and polyether ketones.
20. Crosslinked polymers derived from aldehydes condensation resins such as phenol/formaldehyde resins, urea/formaldehyde resins and melamine/formaldehyde resins.
21. Drying and non-drying alkyd resins.
22. Unsaturated polyester resins derived from copolyesters of saturated and unsaturated dicarboxylic acids with polyhydric alcohols and vinyl compounds as crosslinking agents and also halogen-containing modifications thereof.
23. Crosslinkable acrylic resins derived from substituted acrylates such as epoxy acrylates, hydroxy acrylates, isocyanato acrylates, urethane acrylates or polyester acrylates.
24. Alkyd resins, polyester resins and acrylate resins crosslinked with melanine resins, urea resins, isocyanates, isocyanurates, carbamates or epoxy resins.
25. Crosslinked epoxy resins derived from aliphatic, cycloaliphatic, heterocyclic and/or aromatic glycidyl compounds such as bisphenol A and bisphenol F, which are crosslinked with customary hardeners such as anhydrides or amines.
26. Natural polymers such as cellulose, rubber, gelatin and chemically modified homologous derivatives thereof, including cellulose acetates, cellulose propionates and cellulose butyrates, or the cellulose ethers such as methyl cellulose, as well as rosins and their derivatives.
27. Polysiloxanes.
28. Michael addition polymers of amines or blocked amines (e.g., ketimines) with activated unsaturated and/or methylene compounds such as acrylates and methacrylates, maleates and acetoacetates.
29. Mixtures or blends of any of the above, such as PP/EPDM, polyamide/EPDM or ABS, PVC/EVA, PVC/ABS, PVC/MBS, PC/ABS, PBTP/ABS, PC/ASA, PC/PBT, PVC/CPE, PVC/acrylate, POM/thermoplastic PUR, PC/thermoplastic polyurethane, POM/acrylate, POM/MBS, PPO/HIPS, PPO/PA6.6 and copolymers, PA/HDPE, PP/HDPE, PP/LDPE, LDPE/HDPE, LDPE/EVA, LDPE/EAA, PA/PP, PA/PPO, PBT/PC/ABS, PBT/PET/PC and the like.
30. Polyketimines in combination with unsaturated acrylic polyacetoacetate resins or with unsaturated acrylic resins including urethane acrylates, polyether acrylates, vinyl or acryl copolymers with pendant unsaturated groups and acrylated melamines.
31. Radiation curable compositions containing ethylenically unsaturated monomers or oligomers and a polyunsaturated aliphatic oligomer.
32. Epoxymelamine resins such as light-stable epoxy resins cross-linked by an epoxy functional coetherified high solids melamine resin.

Other materials which can be stabilized include, for example:
33. Naturally occurring and synthetic organic materials which may be mixtures of compounds, including mineral oils, animal and vegetable fats, oils and waxes, or oils, fats or waxes based on synthetic esters (e.g., phthalates, adipates, phosphates or trimellitates) and also mixtures of synthetic esters with mineral oils in any ratio.
34. Aqueous emulsions of natural or synthetic rubber such as natural latex or lattices of carboxylated styrene/butadiene copolymers.
35. Organic dyes such as azo dyes (diazo, triazo and polyazo), anthraquinones, benzodifu ranones, polycyclic aromatic carbonyl dyes, indigoid dyes, polymethines, styryl dyes, di- and triaryl carbonium dyes, phthalocyanines, quinophthalones, sulfur dyes, nitro and nitroso dyes, stilbene dyes, formazan dyes, quinacridones, carbazoles and perylene tetracarboxylic diimides.
36. Cosmetic products, such as skin lotions, collagen creams, sunscreen, facial make-up, etc., comprising synthetic materials such as antioxidants, preservatives, lipids, solvents, surfactants, colorants, antiperspirants, skin conditioners, moisturizers etc.; as well as natural products such as collagen, proteins, mink oil, olive oil, coconut oil, carnauba wax, beeswax, lanolin, cocoa butter, xanthan gum, aloe, etc.
37. Cellulose-based paper formulations for use, e.g., in newsprint, cardboard, posters, packaging, labels, stationery, book and magazine paper, bond typing paper, multipurpose and office paper, computer paper, xerographic paper, laser and ink-jet printer paper, offset paper, currency paper, etc.
38. Photographic film paper.
39. Ink.

As mentioned above, one particular advantage of the amido or carbamate containing trisaryl-1,3,5-triazines of the present invention is that they can be chemically bound to substrates, such as polymers, thereby greatly reducing the migration of such UV absorbers, e.g., out of the substrate or away from the substrate surface. The bonding mechanism of the triazines of the present invention involves the formation of a bond (chemical and/or covalent) between a functionality attached to the amido or carbamate group, e.g., by a pendant vinyl or hydroxyl group, and the "host" substrate, such as a polymer.

Incorporation of the trisaryl-1,3,5-triazines of the invention can be brought about by copolymerization, copolyaddition, copolycondensation, by reaction with a polymer which carries suitable functional groups, or by grafting, in a manner as disclosed in previously incorporated U.S. Pat. No. 3,423,360 and U.S. 5,189,084.

Bonding of the trisaryl-1,3,5-triazines of the invention can occur by polymerization or copolymerization, In the case of the novel triazines of the present invention comprising pendant vinyl groups, polymerization or copolymerization with at least one vinyl monomer, e.g., (meth)acrylic acid, esters of (meth)acrylic acid such as methyl acrylate, amides of (meth)acrylic acid, hydroxyethylacrylate, olefins, vinyl chloride, styrene, butadiene, isoprene and acrylonitrile can be carried out to form homopolymers or copolymers in which the vinyl group is incorporated into the backbone of the polymer. Polymerization or copolymerization can be initiated by initiators, such as free radical, anionic and cationic types, or by actinic radiation, such as UV, electron beam, x-rays and gamma irradiation from a $Co^{60}$ source, as is well known to those in the polymerization art. Polymerization or copolymerization can be carried out in solution, in an emulsion, in a dispersion, in the melt, or in the solid state as is well known to those in the polymerization art.

In addition, bonding of the presently claimed amido or carbamate containing trisaryl-1,3,5-triazine compounds of the present invention of the formulas (I), (II), or (III) can be brought about by copolyaddition or copolycondensation. Such incorporation can be made by addition during the synthesis of an addition polymer or copolymer or by condensation during the synthesis of a condensation polymer or copolymer by methods known to those skilled in the art. For example, compounds of the formulas (I), (II), or (III) containing the appropriate functional groups can be incorporated into polyesters, polyamides, polyurethanes, epoxy resins, melamine resins, alkyd resins, phenolic resins, polyurethanes, polycarbonates, polysiloxanes, polyacetals and polyanhydrides, to name but a few.

In addition, compounds of the formulas (I), (II), or (III) can be bonded to a monomeric component which is then incorporated into a polymer or copolymer, e.g., by the free radical initiated addition or copolycondensation methods described above. Analagous methods are disclosed in, for example, U.S. Pat. No. 5,459,222 (incorporated by reference herein for all purposes as if fully set forth) for the bonding of benzotriazole and benzophenone stabilizers to diol precursors which are then incorporated by condensation polymerization into polyurethanes and polyesters to impart UV stabilizing properties to said polymers.

Alternately, the trisaryl-1,3,5-triazines of the invention may also be bonded to polymers by reaction with an oligomer and/or polymer which carries suitable functional groups. For example, at least one triazine compound comprising a vinyl pendant group can be added, optionally with at least one other vinyl monomer or compound comprising a vinyl group, to unsaturated polyester resins, unsaturated polybutadiene oligomers or unsaturated rubbers and then cured by actinic radiation or by a free radical catalyst. Or, at least one triazine compound comprising a terminal functional group, such as hydroxyl or amido, may be reacted with a polymer and/or oligomer such as polyesters, polyurethanes and polydiols with reactive end-groups, partially hydrolyzed polyvinylacetate, epoxy resins, polysiloxanes and polymers comprising maleic anhydride, either in the main chain or as a side-chain, by methods analagous to those well known to those of ordinary skill in the art.

Grafting is yet another way of bonding of the presently claimed amido or carbamate containing trisaryl-1,3,5-triazine compounds of the formulas (I), (II), or (III) to polymers and/or oligomers. Grafting may be carried out in solution, in the melt, or in the solid state with the initiators or actinic radiation types discussed above for polymerization when, for example, the novel triazines of the present invention comprising pendant vinyl groups are used. Such amido or carbamate containing trisaryl-1,3,5-triazines may be grafted to saturated polymers, e.g., polyolefins and their copolymers such as polyethylene, polypropylene and poly (ethylene-vinyl acetate), or to polymers comprising unsaturated moieties, e.g., polybutadiene, polyisoprene, ethylenepropylene-(diene monomer) terpolymers and polystyrene and its copolymers.

The amido or carbamate containing trisaryl-1,3,5-triazines of the present invention may be used in widely varying amounts in such applications depending upon such things as the material to be stabilized and the particular application. However, when employed as a stabilizing additive for materials such as organic polymers, the trisaryl-1, 3,5-triazines of the present invention are typically employed in amounts from about 0.01 to about 20% by weight, preferably from about 0.1 to about 10% by weight, and most preferably from about 0.1 to about 5% by weight, based on the weight of the material to be stabilized. In screening applications such as sunscreening compositions, the triazines are utilized in the same relative amounts but based on the total weight of the screening agent.

The novel stabilizers of the present invention may also be employed in a non-bondable capacity, for example, in the stabilization of thermoplastic polymers as set forth in the many of the previously incorporated references. Examples of preferred thermoplastic polymers are polyolefins and polymers comprising heteroatoms in the main chain. Preferred polymers are also thermoplastic polymers comprising nitrogen, oxygen and/or sulphur, especially nitrogen or oxygen, in the main chain. Also of interest are compositions in which the polymer is a polyolefin, for example polyethylene or polypropylene.

Incorporation into the thermoplastic polymers can be carried out by addition of the novel amido or carbamate containing triazine compound and any further additives by the methods conventional in the art. The incorporation can expediently be made before or during shaping, for example by mixing the pulverulent components or by adding the stabilizer to the melt or solution of the polymer, or by applying the dissolved or dispersed compounds to the polymer, with or without subsequent evaporation of the solvent. Elastomers can also be stabilized as lattices.

The novel mixtures can also be added to the polymers to be stabilized in the form of a masterbatch which comprises these compounds, for example, in a concentration of from about 2.5 to about 25%, preferably from about 5 to about 20% by weight of the polymer.

The novel mixtures can expediently be incorporated into the polymeric material by any number of methods, including those conventionally employed in the art, including by, for example: a) as an emulsion or dispersion (for example to lattices or emulsion polymers); (b) as a dry mix during mixing of additional components or polymer mixtures; (c) by direct addition to the processing equipment (for example extruders, internal mixers, etc.); or (d) as a solution or melt.

The stabilized polymer compositions obtained in this way can be converted into shaped articles, for example fibers, films, tapes, sheets, sandwich boards, containers, pipes and other profiles, by any number of conventional methods, for example hot pressing, spinning, extrusion, roto-molding or injection molding. Therefore, the present invention additionally relates to the use of the polymer composition according to the invention for the production of a shaped article.

Depending upon their ultimate end use, the amido or carbamate containing trisaryl-1,3,5-triazines of the present invention may be combined with a variety of additives conventionally employed in the UV stabilizing art. Examples of such additives include but are not limited to:

a. Antioxidants (i) Alkylated monophenols such as 2,6-di-tert-butyl-4-methylphenol; 2-tert-butyl-4,6-dimethylphenol; 2,6-di-tert-butyl-4-ethylphenol; 2,6-di-tert-butyl-4-n-butylphenol; 2,6-di-tert-butyl-4-isobutylphenol; 2,6-dicyclopentyl-4-methylphenol; 2-(a-methylcyclohexyl)-4,6-dimethylphenol; 2,6-dioctadecyl-4-methylphenol; 2,4,6-tricyclohexylphenol; 2,6-di-tert-butyl-4-methoxymethylphenol; nonylphenols which are liner or branched in the side chains such as 2,6-di-nonyl-4-methylphenol; 2,4-dimethyl-6-(1-methylundec-1-yl) phenol; 2,4-dimethyl-6-(1-methylheptadec-1-yl)phenol; 2,4-dimethyl-6-(1-methyltridec-1-yl)phenol; and mixtures thereof.

(ii) Alkylthiomethylphenols such as 2,4-dioctylthiomethyl-6-tert-butylphenol; 2,4-dioctylthiomethyl-6-methylphenol; 2,4-dioctylthiomethyl-6-ethylphenol; and 2,6-di-dodecylthiomethyl-4-nonylphenol.

(iii) Hydroquinones and alkylated hydroquinones such as 2,6-di-tert-butyl-4-methoxyphenol; 2,5-di-tert-butylhydroquinone; 2,5-di-tert-amylhydroquinone; 2,6-diphenyl-4-octadecyloxyphenol; 2,6-di-tert-butylhydroquinone; 2,5-di-tert-butyl-4-hydroxyanisole; 3,5-di-tert-butyl-4-hydroxyanisole; 3,5-di-tert-butyl-4-hydroxyphenyl stearate; and bis(3,5-di-tert-butyl-4-hydroxyphenyl)adipate.

(iv) Tocopherols such as α-tocopherol, β-tocopherol, y-tocopherol, δ-tocopherol and mixtures thereof (vitamin E).

(v) Hydroxylated thiodipbenyl ethers such as 2,2-thiobis(6-tert-butyl-4-methylphenol); 2,2'-thiobis(4-octylphenol); 4,4'-thiobis(6-tert-butyl-3-methylphenol); 4,4'-thiobis(6-tert-butyl-2-methylphenol); 4,4-thiobis(3,6-di-sec-amylphenol); and 4,4'-bis(2,6-dimethyl-4-hydroxyphenyl)disulfide.

(vi) Alkylidenebisphenols such as 2,2'-methylenebis(6-tert-butyl-4-methylphenol); 2,2'-methylenebis(6-tert-butyl-4-ethylphenol); 2,2'-methylenebis[4-methyl-6-(α-methylcyclohexyl)phenol]; 2,2-methylenebis(4-methyl-6-cyclohexylphenol); 2,2'-methylenebis(6-nonyl-4-methylphenol); 2,2-methylenebis(4,6-di-tert-butylphenol); 2,2'-ethylidenebis(4,6-di-tert-butylphenol); 2,2'-ethylidenebis(6-tert-butyl-4-isobutylphenol); 2,2'-methylenebis[6-(α-methylbenzyl)-4-nonylphenol]; 2,2'-methylenebis[6-(α,α-dimethylbenzyl)-4-nonylphenol]; 4,4'-methylenebis(2,6-di-tert-butylphenol); 4,4'-methylenebis(6-tert-butyl-2-methylphenol); 1,1-bis(5-tert-butyl-4-hydroxy-2-methylphenyl)butane; 2,6-bis(3-tert-butyl-5-methyl-2-hydroxylbenzyl)-4-methylphenol; 1,1,3-tris(5-tert-butyl-4-hydroxy-2-methylphenyl)butane;

1,1-bis(5-tert-butyl-4-hydroxy-2-methylphenyl)-3-n-dodecylmercaptobutane; ethylene glycol bis[3,3-bis(3'-tert-butyl-4'-hydroxyphenyl)butyrate], bis(3-tert-butyl-4-hydroxy-5-methylphenyl)dicyclopentadiene; bis[2-(3'-tert-butyl-2'-hydroxy-5'-methylbenzyl)-6-tert-butyl-4-methylphenyl]terephthalate; 1,1-bis(3,5-dimethyl-2-hydroxyphenyl)butane; 2,2-bis(3,5-di-tert-butyl-4-hydroxyphenyl)propane; 2,2-bis(5-tert-butyl-4-hydroxy-2-methylphenyl)-4-n-dodecylmercaptobutane; and 1,1,5,5-tetra(5-tert-butyl-4-hydroxy-2-methylphenyl)pentane.

(vii) O-, N- and S-benzyl compounds such as 3,5,3',5'-tetra-tert-butyl-4,4'-dihydroxydibenzyl ether; octadecyl-4-hydroxy-3,5-dimethylbenzylmercaptoacetate; tridecyl-4-hydroxy-3,5-di-tert-butylbenzylmercaptoacetate; tris(3,5-di-tert-butyl-4-hydroxybenzyl)amine; bis(4-tert-butyl-3-hydroxy-2,6-dimethylbenzyl)dithioterephthalate; bis(3,5-di-tert-butyl-4-hydroxybenzyl)sulfide; and isooctyl-3,5-di-tert-butyl-4-hydroxybenzylmercaptoacetate.

(viii) Hydroxybenzylate malonates such as dioctadecyl-2,2-bis(3,5-di-tert-butyl-2-hydroxybenzyl)malonate; dioctadecyl-2-(3-tert-butyl-4-hydroxy-5-methylbenzyl) malonate; didodecylmercaptoethyl-2,2-bis(3,5-di-tert-butyl-4-hydroxybenzyl)malonate; and bis[4-(1,1,3,3-tetramethylbutyl)phenyl]-2,2-bis(3,5-di-tert-butyl-4-hydroxybenzyl)malonate.

(ix) Aromatic hydroxybenzyl compounds such as 1,3,5-tris(3,5-di-tert-butyl-4-hydroxybenzyl)-2,4,6-trimethylbenzene; 1,4-bis(3,5-di-tert-butyl-4-hydroxybenzyl)-2,3,5,6-tetramethylbenzene; and 2,4,6-tris(3,5-di-tert-butyl-4-hydroxybenzyl)phenol.

(x) Triazine compounds such as 2,4-bis(octylmercapto-6-(3,5-di-tert-butyl-4-hydroxyanilino)-1,3,5-triazine; 2-octylmercapto-4,6-bis(3,5-di-tert-butyl-4-hydroxyanilino)-1,3,5-triazine; 2-octylmercapto-4,6-bis(3,5-di-tert-butyl-4-hydroxyphenoxy)-1,3,5-triazine; 2,4,6-tris(3,5-di-tert-butyl-4-hydroxyphenoxy)- 1,3,5-triazine; 1,3,5-tris(3,5-di-tert-butyl-4-hydroxybenzyl)isocyanurate; 1,3,5-tris(4-tert-butyl-3-hydroxy-2,6-dimethylbenzyl)isocyanurate; 2,4,6-tris(3,5-di-tert-butyl-4-hydroxyphenylethyl)-1,3,5-triazine; 1,3,5-tris(3,5-di-tert-butyl-4-hydroxyphenylpropionyl)-hexahydro-1,3,5-triazine; and 1,3,5-tris(3,5-dicyclohexyl-4-hydroxybenzyl)isocyanurate.

(xi) Benzylphosphonates such as dimethyl-2,5-di-tert-butyl-4-hydroxybenzylphosphonate; diethyl-3,5-di-tert-butyl-4-hydroxybenzylphosphonate; dioctadecyl-3,5-di-tert-butyl-4-hydroxybenzylphosphonate; dioctadecyl-5-tert-butyl-4-hydroxy-3-methylbenzylphosphonate; and the calcium salt of the monoethyl ester of 3,5-di-tert-butyl-4-hydroxybenzylphosphonic acid.

(xii) Acylaminophenols such as 4-hydroxylauranilide; 4-hydroxystearanilide; and octyl N(3,5-di-tert-butyl-4-hydroxyphenyl)carbamate.

(xiii) Esters of β-(3,5-di-tert-butyl-4-hydroxyphenyl) propionic acid with mono- or polyhydric alcohols such as methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl) oxamide, 3-thiaundecanol, 3-thiapentadecanol, trimethylhexanediol, trimethylolpropane and 4-hydroxymethyl-1-phospha-2,6,7-trioxabicyclo[2.2.2] octane.

(xiv) Esters of β-(5-tert-butyl-4-hydroxy-3-methylphenyl) propionic acid with mono- or polyhydric alcohols such as methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl) oxamide, 3-thiaundecanol, 3-thiapentadecanol, trimethylhexanediol, trimethylolpropane and 4-hydroxymethyl-1-phospha-2 ,6,7-trioxabicyclo[2.2.2] octane.

(xv) Esters of β-(3,5-dicyclohexyl-4-hydroxyphenyl) propionic acid with mono- or polyhydric alcohols such as methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)-oxamide, 3-thiaundecanol, 3-thiapentadecanol, trimethylhexanediol, trimethylolpropane and 4-hydroxymethyl-1-phospha-2,6,7-trioxabicyclo[2.2.2] octane.

(xvi) Esters of 3,5-di-tert-butyl-4-hydroxyphenyl acetic acid with mono- or polyhydric alcohols such as methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis-(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2] octane.

(xvii) Amides of β-(3,5-di-tert-butyl-4-hydroxyphenyl) propionic acid such as N,N'-bis(3,5-di-tert-butyl-4-hydroxyphenylpropionyl)hexamethylenediamine; N,N'-bis(3,5-di-tert-butyl-4-hydroxyphenylpropionyl) trimethylenediamine; and N,N'-bis(3,5-di-tert-butyl-4-hydroxyphenylpropionyl)hydrazine.

(xviii) Ascorbic acid (Vitamin C).

(xix) Aminic antioxidants such as N,N'-diisopropyl-p-phenylenediamine; N,N'-di-secbutyl-p-phenylenediamine; N,N'-bis(1,4-dimethylpentyl)-p-phenylenediamine; N,N'bis(1-ethyl-3-methylpentyl)-p-phenylenediamine; N,N'-bis(1-methylheptyl)-p-phenylenediamine; N,N'-dicyclohexyl-p-phenylenediamine; N,N'-diphenyl-p-phenylenediamine; N,N'-bis(2-naphthyl)-p-phenylenediamine; N-isopropyl-N'phenyl-p-phenylenediamine; N-(1,3-dimethylbutyl)-N'-phenyl-p-phenylenediamine; N-(1-methylheptyl)-N'-phenyl-p-phenylenediamine; N-cyclohexyl-N'-phenyl-pphenylenediamine; 4-(p-toluenesulfonamoyl) diphenylamine; N,N'-dimethyl-N,N'-disec-butyl-p-phenylenediamine; diphenylamine; N-allyldiphenylamine; 4-isopropoxydiphenylamine; N-phenyl-1-naphthylamine; N-(4-tert-octylphenyl)-1-naphthylamine; N-phenyl-2-naphthylamine; octylated diphenylamine such as p,p'-di-tert-octyldiphenylamine; 4-n-butylaminophenol; 4-butyrylaminophenol; 4-nonanoylaminophenol; 4-dodecanoylaminophenol; 4-octadecanoylaminophenol; bis(4-methoxyphenyl) amine; 2,6-di-tert-butyl-4-dimethylaminomethylphenol; 2,4'-diaminophenylmethane; 4,4'-diaminodiphenylmethane; N,N,N',N'-tetramethyl-4,4'-diaminodiphenylmethane; 1,2-bis[(2-methylphenyl) amino]ethane; 1,2-bis(phenylamino)propane; (o-tolyl) biguanide; bis[4-(1',3'-dimethylbutyl)phenyl]amine; tert-octylated N-phenyl-1-naphthylamine; a mixture of mono- and dialkylated tert-butyl/tert-octyldiphenylamines, a mixture of mono- and dialkylated nonyldiphenylamines; a mixture of mono- and dialkylated dodecyldiphenylamines; a mixture of mono- and dialkylated isopropyl/isohexyldiphenylamines, a mixture of mono- and dialkylated tertbutyldiphenylamines; 2,3-dihydro-3,3-dimethyl-4H-1,4-benzothiazine; phenothiazine; a mixture of mono- and dialkylated tert-butyl/tert-octyl phenothiazines; a mixture of mono- and dialkylated tert-octylphenothiazines; Nallylphenothiazine; N,N,N',N'-tetraphenyl-1,4-diaminobut-2-ene; N,N-bis(2,2,6,6-tetramethylpiperid-4-yl)hexamethylenediamine; bis(2,2,6,6-tetramethylpiperid-4-yl)sebacate; 2,2,6,6-tetramethylpiperidin-4-one; and 2,2,6,6-tetramethylpiperidin-4-UV-absorbers and light stabilizers (i) 2-(2'-Hydroxyphenyl)benzotriazoles such as 2-(2'-hydroxy-5'-methylphenyl)-benzotriazole; 2-(3',5'-di-tert-butyl-2'-hydroxyphenyl)benzotriazole; 2-(5'-tert-butyl-2'-hydroxyphenyl)benzotriazole; 2-(2'-hydroxy-5'-(1,1,3,3-tetramethylbutyl)phenyl)benzotriazole; 2-(3',5'-di-tert-butyl-2'-hydroxyphenyl)-5-chlorobenzotriazole; 2-(3'-tert-butyl-2'-hydroxy-5'-methylphenyl)-5-chlorobenzotriazole; 2-(3'-sec-butyl-5'-tert-butyl-2'-hydroxyphenyl)-benzotriazole; 2-(2'-hydroxy-4'-octoxyphenyl)benzotriazole; 2-(3',5'-di-tert-amyl-2'-hydroxphenyl)benzotriazole; 2-(3',5'-bis(α,α'-dimethylbenzyl)-2'-hydroxyphenyl)-benzotriazole; 2-(3'-tert-butyl-2'-hydroxy-5'-(2-octyloxycarbonylethyl)phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2-hydroxy-5'-(2-methoxycarbonylethyl)phenyl)-5-chloro-benzotriazole, 2-(3'-tert-butyl-2'-hydroxy-5'-(2-methoxycarbonylethyl)phenyl)benzotriazole, 2-(3'-tert-butyl-2'-hydroxy-5'-(2-octyloxycarbonylethyl)phenyl)benzotriazole, 2-(3'-tert-butyl-5'-(2-(2-ethylhexyloxycarbonylethyl)phenyl-2'-hydroxyphenyl)benzotriazole, 2-(3'-dodecyl-2'-hydroxy-5'-methylphenyl)benzotriazole; 2-(3'-tert-butyl-2'-hydroxy-5'-(2-isooctyloxycarbonylethyl)phenylbenzotriazole; 2,2-methylenebis[4-(1,1,3,3-tetramethylbutyl)-6-benzotriazol-2-ylphenol]; a mixture of the transesterification product of 2-[3'-tert-butyl-5'-(2-methoxycarbonylethyl)-2'-hydroxyphenyl]benzotriazole with polyethylene glycol 300; [R—CH$_2$CH$_2$—CO(CH$_2$CH$_2$)$_2$— where R=3'-tert-butyl-4'-hydroxy-5'-2H-benzotriazol-2-ylphenyl; 2-[2'-hydroxy-3'-(1,1,3,3-tetramethylbutyl)-5'-(α,α'-dimethylbenzyl)phenyl]benzotriazole and 2-[2'-hydroxy-3'-(α,α'-dimethylbenzyl)-5'-(1,1,3,3-tetramethylbutyl)phenyl]benzotriazole.

(ii) 2-Hydroxybenzophenones, for example the 4-hydroxy, 4-methoxy, 4-octoxy, 4-decyloxy, 4-dodecyloxy, 4-benzyloxy, 4,2',4'-trihydroxy and 2'-hydroxy-4,4'-dimethoxy derivative.

(iii) Esters of substituted and unsubstituted benzoic acids such as 4-tert-butyl-phenyl salicylate; phenyl salicylate; octylphenyl salicylate; dibenzoyl resorcinol; bis(4-tert-butylbenzoyl) resorcinol; benzoyl resorcinol; 2,4-di-tert-butylphenyl 3,5-di-tert-butyl-4-hydroxybenzoate; hexadecyl 3,5-di-tert-butyl-4-hydroxybenzoate; octadecyl 3,5-di-tert-butyl-4-hydroxybenzoate; and 2-methyl-4,6-di-tert-butylphenyl 3,5-di-tert-butyl-4-hydroxybenzoate.

(iv) Acrylates and benzylide malonates such as ethyl α-cyano-β,β-dephenylcrylate; isooctyl α-cyano-β,β-diphenylacrylate; methyl α-carbomethoxycinnamate; methyl α-cyano-β-methyl-p-methoxycinnamate; butyl α-cyano-β-methyl-p-methoxycinnamate; methyl α-carbomethoxy-p-methoxycinnamate; and N-(β-carbomethoxy-β-cyanovinyl)-2-methylindoline and propanedioic acid,[(4-methoxyphenyl)methylene]-, dimethyl ester.

(v) Nickel compounds such as nickel complexes of 2,2'-thio-bis-[4-(1,1,3,3-tetramethylbutyl)phenol], including the 1:1 or 1:2 complex, with or without additional ligands such as n-butylamine, triethanolamine or N-cyclohexyldiethanolamine; nickel dibutyldithiocarbamate; nickel salts of monoalkyl esters including the methyl or ethyl ester of 4-hydroxy-3,5-di-tert-butylbenzylphosphonic acid; nickel complexes of ketoximes including 2-hydroxy-4-methylphenyl undecyl ketoxime; and nickel complexes of 1-phenyl-4-lauroyl-5-hydroxypyrazole, with or without additional ligands.

(vi) Sterically hindered amines as well as the N derivatives thereof (e.g., N-alkyl, N- hydroxy, N-alkoxy and N-acyl), such as monomeric HALS, including 4-benzoyl-2,2,6,6-tetramethylpiperidine; 4-stearyloxy-2,2,6,6-tetramethylpiperidine; a mixture of 4-hexadecyloxy- and 4-stearyloxy-2,2,6,6-tetramethylpiperidine; 1-octyloxy-2,2,6,6-tetramethylpiperidin-4-yl methacrylate; 2-(2-hydroxyethylamino)-4,6-bis(4-n-butylamino-1,2,2,6,6-pentamethylpiperidyl)-1,3,5-triazine; bis(2,2,6,6-tetramethylpiperidin-4-yl)sebacate; bis(2,2,6,6-tetramethylpiperidin-4-yl)succinate; bis(1,2,2,6,6-pentamethylpiperidin-4-yl)sebacate; bis(1,2,2,6,6-pentamethylpiperidin-4-yl)succinate; bis(1-octyloxy-2,2,6,6-tetramethylpiperidin-4-yl)sebacate; bis(1-octyloxy-2,2,6,6-tetramethylpiperidin-4-yl)succinate; 3-n-dodecyl-7,7,9,9-tetramethyl-1,3,8-triazaspiro[4.5]decan-2,4-dione; 3-n-octyl-7,7,9,9-tetramethyl-1,3,8-triazaspiro[4.5]decan-2,4-dione; bis(1,2,2,6,6-pentamethylpiperidin-4-yl) 2-n-butyl-2-3,5-di-tert-butyl-4-hydroxybenzyl)malonate; 3-dodecyl-1-(2,2,6,6-tetramethylpiperidin-4-yl)pyrrolidin-2,5-dione; 3-dodecyl-1-(1,2,2,6,6-pentamethylpiperidin-4-yl)pyrrolidin-2,5-dione; 3-dodecyl-1-(1-ethanoyl-2,2,6,6-tetramethylpiperidin-4-yl)pyrrolidin-2,5-dione; 2-undecyl-7,7,9,9-tetramethyl-1-oxa-3,8-diaza-4-oxospiro[4.5]decane; 7-oxa-3,20-diazadispiro[5.1.11.2]heneicosane-20-propanoic acid, 2,2,4,4-tetramethyl-2 1-oxo-, dodecyl ester; 2,2,4,4-tetramethyl-7-oxa-3,20-diaza-21-oxo-dispiro[5.1.11.2] heneicosane; b-alanine, N-(2,2,6,6-tetramethyl-4-piperidinyl)-, mixture of dodecyl and tetradecyl esters; N,N'-bis(2,2,6,6-tetramethyl-4-piperidinyl)-1,3-benzenedicarboxamide; tris(2,2,6,6-tetramethylpiperidin-4-yl)nitrilotriacetate; tetrakis(2,2,6,6-tetramethylpiperidin-4-yl)-1,2,3,4-butanetetracarboxylate; N,N'-bis-formyl-N,N'-bis(2,2,6,6-tetramethyl-4-piperidyl)hexamethylenediamine; Oligomeric/polymeric HALS such as the condensate of 1-(2-hydroxyethyl)-2,2,6,6-tetramethyl-4-hydroxypiperidine and dimethyl succinate; the condensate of 1-(2-hydroxyethyl)-2,2,6,6-tetramethyl-4-hydroxypiperidine and succinic acid; the condensate of 1-(2-hydroxyethyl)-2,2,6,6-tetramethyl-4-hydroxypiperidine and 2,2-diethylmalonic acid; the condensate of N,N'-bis(2,2,6,6-tetramethylpiperidin-4-yl)hexamethylenediamine and 4-tert-octylamino-2,6-dichloro-1,3,5-triazine; the condensate of N,N'-bis(2,2,6,6-tetramethylpiperidin-4-yl)hexamethylenediamine and 4-morpholino-2,6-dichloro-1,3,5-triazine; the condensate of N,N'-bis(2,2,6,6-tetramethylpiperidin-4-yl)hexamethylenediamine and 4-cyclohexylamino-2,6-dichloro-1,3,5-triazine; the condensate of N,N'-bis(2,2,6,6-tetramethylpiperidin-4-yl)hexamethylenediamine, 2,4-dichloro-the condensate of 2-chloro-4,6-bis(4-n-butylamino-2,2,6,6-tetramethylpiperidyl)-1,3,5-triazine and 1,2-bis(3-aminopropylamino)ethane; the condensate of 2-chloro-4,6- bis(4-n-butylamino-1,2,2,6,6-pentamethylpiperidyl)-1,3,5-triazine and 1,2-bis-(3-aminopropylamino)ethane; poly[methylpropyl-3-oxy-4-(2,2,6,6-tetramethyl-4-piperidyl)]siloxane; the reaction product of 7,7,9,9-tetramethyl-2-cycloundecyl-1-oxa-3,8-diaza-4-oxospiro[4.5]decane and epichlorohydrin; reaction product of maleic acid anhydride-a-olefin-copolymer with 2,2,6,6-tetramethyl-4-aminopiperidine or 1,2,2,6,6-pentamethyl-4-aminopiperidine; and other HALS including photobondable HALS such as propanedioic acid, {(4-methoxyphenyl)methylene}-, bis(1,2,2,6,6-pentamethyl-4-piperidinyl) ester; propanedioic acid, [(4-methoxyphenyl)methylene]-, bis(1-acetyl-2,2,6,6-pentamethyl-4-piperidinyl) ester, and similar materials disclosed in GB-A-2269819; oxo-piperanzinyl-triazines or so-called PIP-T HALS, e.g., 1,1'-(1,2-ethanediyl)bis(3,3,5,5-tetramethylpiperazinone); 1,1',1''-[1,3,5-triazine-2,4,6-triyltris[(cyclohexylimino)-2,1-ethanediyl]]tris[3,3,5,5-tetramethylpiperazinone]; 1,1',1''-[1,3,5-triazine-2,4,6-triyltris[(cyclohexylimino)-2,1-ethanediyl]]tris[3,3,4,5,5-pentamethylpiperazinone] and similar materials disclosed in U.S. Pat. No. 5,071,981.

See also generally J. Pospíšil and P. P. Klemchuk, *Oxidation Inhibition in Organic Materials,* Vol., II (1990), pp. 58–60, U.S. Pat. No. 4,619,956, U.S. 5,106,891, EP-A-0309400, EP-A-0309401, EP-A-0309402 and EP-A-0434608.

bis(2,2,6,6-tetramethylpiperidin-4-yl)sebacate; bis(2,2,6,6-tetramethylpiperidin-4-yl) succinate; bis(1,2,2,6,6-pentamethylpiperidin-4-yl)sebacate; bis(1-octyloxy-2,2,6,6-tetramethylpiperidin-4-yl)sebacate; bis(1,2,2,6,6-pentamethylpiperidin-4-yl) n-butyl 3,5-di-tert-butyl-4-hydroxybenzylmalonate; the condensate of 1-(2-hydroxyethyl)-2,2,6,6-tetramethyl-4-hydroxypiperidine and succinic acid; the condensate of N,N'-bis(2,2,6,6-tetramethylpiperidin-4-yl) hexamethylenediamine and 4-tert-octylamino-2,6-dichloro-1,3,5-triazine; tris(2,2,6,6-tetramethylpiperidin-4-yl) nitrilotriacetate; tetrakis(2,2,6,6-tetramethylpiperidin-4-yl)-1,2,3,4-butanetetracarboxylate; 1,1'-(1,2-ethanediyl)bis(3,3,5,5-tetramethylpiperazinone); 4-benzoyl-2,2,6,6-tetramethylpiperidine; 4-stearyloxy-2,2,6,6-tetramethylpiperidine; bis(1,2,2,6,6-pentamethylpiperidyl)-2-n-butyl-2-(2-hydroxy-3,5-di-tert-butylbenzyl) malonate; 3-n-octyl-7,7,9,9-tetramethyl-1,3,8-triazaspiro[4.5]decan-2,4-dione; bis(1-octyloxy-2,2,6,6-tetramethylpiperidyl)sebacate; bis(1-octyloxy-2,2,6,6-tetramethylpiperidyl)succinate; the condensate of N,N'-bis(2,2,6,6-tetramethylpiperidin-4-yl)hexamethylenediamine and 4-morpholino-2,6-dichloro-1,3,5-triazine; the condensate of 2-chloro-4,6-bis(4-n-butylamino-2,2,6,6-tetramethylpiperidyl)-1,3,5-triazine and 1,2-bis(3-aminopropylamino)ethane; the condensate of 2-chloro-4,6-bis(4-n-butylamino-1,2,2,6,6-pentamethylpiperidyl)-1,3,5-triazine and 1,2-bis-(3-aminopropylamino)ethane; 8-acetyl-3-dodecyl-7,7,9,9-tetramethyl-1,3,8-triazaspiro[4.5]decane-2,4-dione; 3-dodecyl-1-(2,2,6,6-tetramethylpiperidin-4-yl) pyrrolidin-2,5-dione; 3-dodecyl-1-(1-ethanoyl-2,2,6,6-tetramethylpiperidin-4-yl)pyrrolidin-2,5-dione; 3-decyl-1-(1,2,2,6,6-pentamethylpiperidin-4-yl) pyrrolidine-2,5-dione; a mixture of 4-hexadecyloxy- and 4-stearyloxy-2,2,6,6-tetramethylpiperidine; the condensate of N,N'-bis(2,2,6,6-tetramethylpiperidin-4-yl)hexamethylenediamine and 4-cyclohexylamino-2,6-dichloro-1,3,5-triazine; the condensate of 1,2-bis(3-aminopropylamino)ethane, 2,4,6-trichloro-1,3,5-triazine and 4-butylamino-2,2,6,6-tetramethylpiperidine (CAS Reg. No. [136504-96-61]; 2-undecyl-7,7,9,9-tetramethyl-1-oxa-3,8-diaza-4-oxospiro[4.5]decane; oxo-piperanzinyl-triazines or so-called PIP-T HALS, e.g., GOODRITE® 3034, 3150 and 3159 and similar materials disclosed in U.S. Pat. No. 5,071,981; photobondable HALS such as SANDUVOR® PR-31 and PR-32 (Clariant Corp.) and similar materials disclosed in GB-A-2269819; and the reaction product of 7,7,9,9-tetramethyl-2-cycloundecyl-1-oxa-3,8-diaza-4-oxospiro[4.5]decane and epichlorohydrin. See also generally U5461 9956, U.S. Pat. No. 5,106,891, GB-A-2269819, EPA-0309400, EP-A-0309401, EP-A-0309402 and EP-A-0434608, which (to the extent not already done so) are incorporated herein by reference as if fully set forth. (vii) Oxamides such as 4,4'-dioctyloxyoxanilide; 2,2'-diethoxyoxanilide; 2,2'-dioctyloxy-5,5'-di-tert-butoxanilide; 2,2'-didodecyloxy-5,5'-di-tert-butyloxanilide; 2-ethoxy-2'-ethyloxanilide; N,N'-bis(3-dimethylaminopropyl) oxamide; 2-ethoxy-5-tert-butyl-2'-ethyloxanilide and its mixture with 2-ethoxy-2'-ethyl-5,4'-di-tert-butoxanilide; and mixtures of o- and p-methoxy disubstituted oxanilides and mixtures of o- and pethoxy disubstituted oxanilides.

(viii) 2-(2-Hydroxyphenyl)-1,3,5-triazines disclosed in the previously incorporated references, such as 2,4,6-tris(2-hydroxy-4-octyloxyphenyl)-1,3,5-triazine; 2-(2-hydroxy-4-n-octyloxyphenyl)-4,6-bis(2,4-dimethylphenyl)-1,3,5-triazine; 2-(2-hydroxy-4-(mixed iso-octyloxyphenyl)-4,6-bis(2,4-dimethylphenyl)-1,3,5-triazine; 2-(2,4-dihydroxyphenyl)-4,6-bis(2,4-dimethylphenyl)-1,3,5-triazine; 2,4-bis(2-hydroxy-4-propyloxyphenyl)-6-(2,4-dimethylphenyl)-1,3,5-triazine; 2-(2-hydroxy-4-octyloxyphenyl)-4,6-bis(4-methylphenyl)-1,3,5-triazine; 2-(2-hydroxy-4-dodecyloxyphenyl)-4,6-bis(2,4-dimethylphenyl)-1,3,5-triazine; 2-(2-hydroxy-4-tridecyloxyphenyl)-4,6-bis(2,4-dimethylphenyl)-1,3,5-triazine; 2-[2-hydroxy-4-(2-hydroxy-3-butyloxypropyloxy)phenyl]-4,6-bis(2,4-dimethylphenyl)-1,3,5-triazine; 2-[2-hydroxy-4-(2-hydroxy-3-octyloxypropyloxy)phenyl]-4,6-bis(2,4-dimethylphenyl)-1,3,5-triazine; 2-[4-dodecyloxy/tridecyloxy-2-hydroxypropoxy)-2-hydroxyphenyl]-4,6-bis(2,4-dimethylphenyl)-1,3,5-triazine; 2-[2-hydroxy-4-(2-hydroxy-3-dodecyloxypropoxy)phenyl]-4,6-bis(2,4-dimethylphenyl)-1,3,5-triazine; 2-(2-hydroxy-4-hexyloxy)phenyl-4,6-diphenyl-1,3,5-triazine; 2-(2-hydroxy-4-methoxyphenyl)-4,6-diphenyl-1,3,5-triazine; 2,4,6-tris[2-hydroxy-4-(3-butoxy-2-hydroxypropoxy)phenyl]-1,3,5-triazine; and 2-(2-hydroxyphenyl)-4-(4-methoxyphenyl)-6-phenyl-1,3,5-triazine.

(c) Metal deactivators such as N,N'-diphenyloxamide; N-salicylal-N'-salicyloyl hydrazine; N,N'-bis(salicyloyl) hydrazine; N,N'-bis(3,5-di-tert-butyl-4-hydroxyphenylpropionyl)hydrazine; 3-salicyloylamino-1,2,4-triazole; bis(benzylidene)oxalyl dihydrazide; oxanilide; isophthaloyl dihydrazide; sebacoyl bisphenylhydrazide; N,N'diacetyladipoyl dihydrazide; N,N'-bis(salicyloyl)oxalyl dihydrazide; and N,N'bis(salicyloyl) thiopropionyl dihydrazide.

(d) Phosphites and phosphonites, such as triphenyl phosphite; diphenyl alkyl phosphites; phenyl dialkyl phosphites; tris(nonylphenyl) phosphite; trilauryl phosphite; trioctadecyl phosphite; distearyl pentaerythritol diphosphite; tris(2,4-di-tert-butylphenyl)phosphite; diisodecyl pentaerythritol diphosphite; bis(2,4,-di-tert-butylphenyl) pentaerythritol diphosphite; bis(2,6-di-tert-butyl-4- methylphenyl)pentaerythritol diphosphite; bis(isodecyloxy)pentaerythritol diphosphite; bis(2,4-di-tert-butyl-6-methylphenyl)pentaerythritol diphosphite; bis(2,4,6-tris(tert-butyl)phenyl)pentaerythritol diphosphite; tristearyl sorbitol triphosphite; tetrakis(2,4-di-tert-butylphenyl)-4,4'-biphenylene diphosphonite; 6-isooctyloxy-2,4,8,10-tetra-tert-butyl-12H-dibenzo[d,g]-1,3,2-dioxaphosphocin; 6-fluoro-2,4,8,10-tetra-tert-butyl-12-methyl-dibenzo[d,g]-1,3,2-dioxaphosphocin; bis(2,4-di-tert-butyl-6-methylphenyl)methylphosphite; and bis(2,4-di-tert-butyl-6-methylphenyl)ethylphosphite.

(e) Hydroxylamines such as N,N-dibenzylhydroxylamine; N,N-diethylhydroxylamine; N,N-dioctylhydroxylamine; N,N-dilaurylhydroxylamine; N,N-ditetradecylhydroxylamine; N,N-dihexadecylhydroxylamine; N,N-dioctadecylhydroxylamine; N-hexadecyl-N-octadecylhydroxylamine; N-heptadecyl-N-octadecylhydroxylamine; and N,N-dialkylhydroxylamine derived from hydrogenated tallow fatty amines.

(f) Nitrones such as N-benzyl-alpha-phenyl nitrone; N-ethyl-alpha-methyl nitrone; N-octyl-alpha-heptyl nitrone; N-lauryl-alpha-undecyl nitrone; N-tetradecyl-alpha-tridecyl nitrone; N-hexadecyl-alpha-pentadecyl nitrone; N-octadecyl-alpha-heptadecyl nitrone; N-hexadecylalpha-heptadecyl nitrone; N-octadecyl-alpha-pentadecyl nitrone; N-heptadecyl-alphaheptadecyl nitrone; N-octadecyl-alpha-hexadecyl nitrone; and nitrones derived from N,N-dialkylhydroxylamines prepared from hydrogenated tallow fatty amines.

(g) Thiosynergists such as dilauryl thiodipropionate and distearyl thiodipropionate.

(h) Peroxide scavengers such as esters of β-thiodipropionic acid, for example the lauryl, stearyl, myristyl or tridecyl esters; mercaptobenzimidazole or the zinc salt of 2-mercaptobenzimidazole; zinc dibutyldithiocarbamate; dioctadecyl disulfide; and pentaerythritol tetrakis(β-dodecylmercapto)propionate.

(i) Polyamide stabilizers such as copper salts in combination with iodides and/or phosphorus compounds and salts of divalent manganese.

(j) Basic co-stabilizers such as melamine; polyvinylpyrrolidone; dicyandiamide; triallyl cyanurate; urea derivatives; hydrazine derivatives; amines; polyamides; polyurethanes; alkali metal salts and alkaline earth metal salts of higher fatty acids, for example calcium stearate, zinc stearate, magnesium behenate, magnesium stearate, sodium ricinoleate and potassium palmitate; antimony pyrocatecholate; and tin pyrocatecholate.

(k) Nucleating agents including inorganic substances such as talc and metal oxides (e.g. titanium oxide or magnesium oxide) and phosphates, carbonates and sulfates of, preferably, alkaline earth metals; organic compounds such as mono- or polycarboxylic acids and salts thereof, for example 4-tert-butylbenzoic acid, adipic acid, diphenylacetic acid, sodium succinate and sodium benzoate; and polymeric compounds such as ionic copolymers ("ionomers").

(l) Fillers and reinforcing agents such as calcium carbonate; silicates; glass fibers; asbestos; talc; kaolin; mica; barium sulfate; metal oxides and hydroxides; carbon black; graphite; wood flour and flours or fibers from other natural products; and synthetic fibers.

(m) Other additives such as plasticizers, lubricants, emulsifiers, pigments, rheological additives, catalysts, levelling assistants, optical brighteners, flameproofing agents, antistatic agents and blowing agents.

(n) Benzofuranones and indolinones such as those disclosed in U.S. Pat. No. 4,325,863, U.S. 4,338,244, U.S. 5,175,312, U.S. 5,216,052, U.S. 5,252,643, DE-A-431661 1, DE-A-4316622, DE-A-4316876, EP-A-0589839 and EP-A-0591102; 3-[4-(2-acetoxy-ethoxy)phenyl]-5,7-di-tert-butyl-benzofuran-2-one; 5,7-di-tert-butyl-3-[4-(2-stearoyloxyethoxy)-phenyllbenzofuran-2-one; 3,3'-bis[5,7-di-tert-butyl-3-(4-[2-hydroxyethoxyphenyl)benzofuran-2-one]; 5,7-di-tert-butyl-3-)4-eethoxyphenyl)benzofuran-2-one; 3-(4-acetoxy-3,5-dimethylphenyl)-5,7-di-tert-butyl-benzofuran-2-one; 3-(3,5-dimethyl-4-pivaloyloxyphenyl)-5,7-di-tert-butyl-benzofuran-2-one; and 5,7-di-tert-butyl-3-(3,4-dimethylphenyl)-3H-benzofuran-2-one.

The novel amido or carbamate containing trisaryl-1,3,5-triazines of the present invention can also be employed in multilayer systems. In such systems, a polymer composition having from about 0.1 to about 20% by weight and preferably a relatively high content of novel stabilizer, for example, about 5–15% by weight, is applied in a thin film (e.g., about 5–500 μm thick and, preferably, about 10–100 μm thick) to a shaped article made from a polymer containing little or no ultraviolet stabilizers. Such composition may be applied at the same time as the shaping of the base structure, for example by coextrusion in a manner analagous to that described in U.S. Pat. No. 4,948,666 (incorporated by reference herein for all purposes as if fully set forth). Alternatively, application can also be made to the ready-formed base structure, for example by lamination with a film or by coating with a solution. The outer layer or layers of the finished article have the function of a UV filter, which protects the interior of the article from UV light. The outer layer preferably contains about 0.1 to about 20%, preferably about 1 to about 15%, and most preferably about 2 to about 10% by weight of the outer layer composition, of at least one of the presently claimed amido or carbamate containing trisaryl-1,3,5-triazine compounds of the present invention of the formulas (I), (II), or (III).

The polymers stabilized in this way are notable for high weathering resistance, especially for high resistance to UV light. This enables them to retain their mechanical properties, and their color surface properties such as gloss and distinctness of image, for a long time even when used outside. Moreover, due to the bondable nature of the presently claimed triazine compounds, migration of these UV absorbers between the layers of the multi-layer coatings can, under the appropriate circumstances, be minimized.

In another embodiment of the present invention, the novel mixtures comprising compounds of the formulas (I), (II), or (III) can be used as stabilizers for coatings, for example for paints such as disclosed in numerous of the previously incorporated references (see, e.g., U.S. Pat. Nos. 4,619,956, 4,740,542, 4,826,978, 4,962,142, 5,106,891, 5,198,498, 5,298,067, 5,322,868, 5,354,794, 5,369,140, 5,420,204, 5,461,151, 5,476,937, EP-0434608 and EP-A-0444323). Of particular interest are coatings and paints for the automobile industry. The invention therefore also relates to those compositions which are film-forming binders for coatings.

Such novel coating compositions comprise about 0.01 to about 20%, preferably about 0.01 to about 10%, and more preferably about 0.02 to about 5% by weight of the binder of the coating composition of the presently claimed amido or carbamate containing trisaryl-1,3,5-triazines of the present invention.

Multilayer systems are possible here as well (such as electrocoat/basecoatlclearcoat systems), where the concentration of the novel stabilizer in one or more of the layers, and typically the outer layer such as the clearcoat, can be relatively high, for example from about 0.01 to about 20%, preferably about 0.01 to about 10%, and more preferably about 0.02 to about 5% by weight of binder.

The use of the novel stabilizer in coatings is accompanied by the additional advantage that it prevents delamination, i.e. the flaking-off of the coating from the substrate. This advantage is particularly important in the case of metallic substrates, including multilayer systems on metallic substrates, and particularly epoxy e-coated metallic substrates.

The binder can in principle be any binder which is customary in industry, for example those described in Ullmann's Encyclopedia of Industrial Chemistry, 5th Edition, Vol. A18, pp. 368–426, VCH, Weinheim 1991 which is incorporated herein by reference. In general, it is a film-forming binder based on a thermoplastic or curable resin, predominantly on a curable resin. Examples of thermoplastic binders incude acrylics, polyesters, polyurethanes and PVC plastisols. Examples of curable binders include functional alkyd, acrylic, polyester, phenolic, melamine, epoxy and polyurethane resins and mixtures thereof.

Such curable binders can be an ambient curable or a thermosetting binder. Further, in some systems it may be advantageous to add a curing catalyst to such systems. Suitable catalysts which accelerate curing of the binder are described, for example, in Ullmann's Encyclopedia of Industrial Chemistry, Vol. A18, p. 469, VCH Verlagsgesellschaft, Weinheim 1991 which is incorporated herein by reference. Preferred binders include those which comprise a functional acrylate resin and a crosslinking agent.

A wide variety of binders may be employed in such coating systems. Examples of suitable coating compositions containing specific binders include but are not limited to:
1. paints based on ambient curable or thermosetting alkyd, acrylate, polyester, epoxy or melamine resins or mixtures of such resins, if desired with addition of a curing catalyst;
2. two-component polyurethane paints based on hydroxyl-containing acrylate, polyester or polyether resins and aliphatic or aromatic isocyanates, isocyanurates or polyisocyanates;
3. one-component polyurethane paints based on blocked isocyanates, isocyanurates or polyisocyanates which are deblocked during baking;
4. two-component paints based on (poly)ketimines and aliphatic or aromatic isocyanates, isocyanurates or polyisocyanates;
5. two-component paints based on (poly)ketimines and an unsaturated acrylate resin or a polyacetoacetate resin or a methacrylamidoglycolate methyl ester;
6. two-component paints based on carboxyl- or amino-containing polyacrylates and polyepoxides;
7. two-component paints based on acrylate resins containing anhydride groups and on a polyhydroxy or polyamino component;
8. two-component paints based on (poly)oxazolines and acrylate resins containing anhydride groups, or unsaturated acrylate resins, or aliphatic or aromatic isocyanates, isocyanurates or polyisocyanates;
9. two-component paints based on unsaturated polyacrylates and polymalonates;
10. thermoplastic polyacrylate paints based on thermoplastic acrylate resins or externally crosslinking acrylate resins in combination with etherified melamine resins;
11. paint systems based on siloxane-modified or fluorine-modified acrylate resins.

In addition to the binder and novel amido or carbamate containing trisaryl-1,3,5-triazines of the present invention, the coating composition according to the invention preferably further comprise one or more additional ultraviolet light absorbers, including but not limited to those specifically listed above in section b. The additional UV absorbers may be, for example, another tris-aryl-1,3,5-triazine, a 2-hydroxyphenyl-2H-benzotriazole, a 2-hydroxybenzophenone, an ester of an unsubstituted benzoic acid, an acrylate, an oxamide (oxanilide), or any combination of the above. Preferably, the additional UV absorber is a 2-hydroxyphenyl-2H-benzotriazole and the weight ratio of benzotriazole to amido or carbamate triazine is 4:1 to 1:4. More preferably, the weight ratio of benzotriazole to amido or carbamate triazine is 2:1 to 1:2.

To achieve maximum light stability, it is of particular interest to add sterically hindered amines, examples of which are set out in the above-mentioned section b(vi). The invention therefore also relates to a coating composition which, in addition to the binder, the novel amido or carbamate containing trisaryl-1,3,5-triazines and, optionally, additional UV absorbers, comprises a light stabilizer of the sterically hindered amine type. The sterically hindered amine is employed in an amount of about 0.01 to 5% by weight based on the weight of the solid binder, preferably about 0.02 to 2% by weight.

One specific example of such a sterically hindered amine is a 2,2,6,6-tetramethyl piperazinone containing at least one group of the formula:

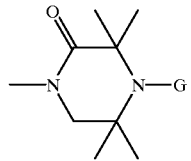

in which G is, for example, hydrogen, hydroxyl, alkyl (such as methyl), alkoxy (such as methoxy) or acyl.

More preferably the stabilizer is a 2,2,6,6-tetraalkylpiperidine derivative containing at least one group of the formula:

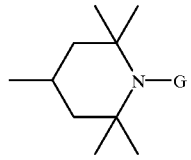

in which G is, for example, hydrogen, hydroxyl, alkyl (such as methyl), alkoxy (such as methoxy) or acyl.

Examples of tetraalkylpiperidine derivatives which can be used in combination with the present trisaryl-1,3,5-triazine compounds are given in U.S. Pat. No. 4,314,933, U.S. 4,344,876, U.S. 4,426,471, U.S. 4,426,472, U.S. 4,619,956, U.S. 5,004,770, U.S. 5,006,577, U.S. 5,064,883, U.S. 5,112,890, U.S. 5,124,378, U.S. 5,106,891, U.S. 5,204,473, U.S. 5,461,151 and EP-A-0434608 which (to the extent not already done so) are incorporated by reference herein for all purposes as if fully set forth. It is particularly expedient to employ the following tetraalkylpiperidine derivatives, as well as their N-alkyl, N-acyl, N-hydroxyl and N-alkoxy analogs (where not already included in the following list): bis(2,2,6,6-tetramethylpiperid-4-yl) succinate; bis(2,2,6,6-tetramethylpiperid-4-yl) sebacate; bis(1,2,2,6,6- pentamethylpiperid-4-yl) sebacate; bis(1-octyloxy-2,2,6,6-tetramethylpiperid-4-yl) sebacate; di(1,2,2,6,6-pentamethylpiperid-4-yl) 2-n-butyl-2-(3,5-di-tert-butyl-4-hydroxybenzyl)malonate; 1-octyloxy-2,2,6,6-tetramethylpiperidin-4-yl methacrylate; 2-(2-hydroxyethylamino)-4,6-bis(4-n-butylamino-1,2,2,6,6-pentamethylpiperidyl)-1,3,5-triazine; tetra(2,2,6,6-tetramethylpiperid-4-yl) butane-1,2,3,4-tetracarboxylate; tetra(1,2,2,6,6-pentamethylpiperid-4-yl) butane-1,2,3,4-tetracarboxylate; 2,2,4,4-tetramethyl-7-oxa-3,20-diaza-21-oxo-dispiro[5.1.11.2]heneicosane; 3-dodecyl-1-(2,2,6,6-tetramethylpiperidin-4-yl)pyrrolidin-2,5-dione; 3-dodecyl-1-(1-acetyl-2,2,6,6-tetramethylpiperidin-4-yl)pyrrolidin-2,5-dione, propanedioic acid, [(4-methoxyphenyl)methylene]-, bis(1,2,2,6,6-pentamethyl-4-piperidinyl) ester; propanedioic acid, [(4-methoxyphenyl)methylene]-, bis(1-acetyl-2,2,6,6-pentamethyl-4-piperidinyl) ester.

Commercially available examples of these and other tetraalkylpipieridine derviatives include SANDJVOR® 3050, 3051, 3052, 3055, 3056, 3058, PR-31 and PR-32 (Clariant Corp.); TINUVIN® 079L, 123, 144, 292, 440L and 622LD (Ciba Specialty Chemicals); CHIMASSORB® 119 and 944 (Ciba Specialty Chemicals); and CYASORB® UV-3346, UV 3529, UV-3853, UV-500 and UV-516 (Cytec Industries, Inc.) 6-(4-n-butylamino-2,2,6,6-tetramethylpiperidyl)-1,3,5-triazine, and di-n-butylamine.

Apart from the binder, the amido or carbamate containing trisaryl-1,3,5-triazine, and, if used, the additional ultraviolet light absorber or stabilizer, the coating composition can also comprise further components, examples being solvents, pigments, dyes, plasticizers, stabilizers, thixotropic agents, drying catalysts and/or leveling agents. Examples of possible components are those described in many of the previously incorporated references as well as Ullmann's Encyclopedia of Industrial Chemistry, 5th Edition, Vol. A18, pp. 429–471, VCH, Weinheim 1991; and Calbo, Leonard J., ed., Handbook of Coatings Additives, New York:Marcel Dekker (1987).

Possible drying catalysts or curing catalysts are, for example, organometallic compounds, amines, amino-containing resins and/or phosphines.

Examples of organometallic compounds are metal carboxylates, especially those of the metals Pb, Mn, Co, Zn, Zr or Cu, or metal chelates, especially those of the metal Al, Ti or Zr, or organometallic compounds such as organotin compounds, for example. Examples of metal carboxylates are the stearates of Pb, Mn or Zn, the octoates of Co, Zn or Cu, the naphthenates of Mn and Co or the corresponding linoleates, resinates or tallates. Examples of metal chelates are the aluminum, titanium or zirconium chelates of acetylacetone, ethyl acetylacetate, salicylaldehyde, salicylaldoxime, ohydroxyacetophenone or ethyl trifluoroacetylacetate and the alkoxides of these metals. Examples of organotin compounds are dibutyltin oxide, dibutyltin dilaurate or dibutyltin dioctoate.

Examples of amine drying or curing catalysts are, in particular, tertiary amines, for example tributylamine, triethanolamine, N-methyldiethanolamine, N-dimethylethanolamine, N-ethylmorpholine, N-methylmorpholine or diazabicyclooctane (triethylenediamine) and salts thereof. Further examples are quaternary ammonium salts, for example trimethylbenzylammonium chloride. Amino-containing resins are simultaneously binder and curing catalyst. Examples thereof are amino-containing acrylate copolymers.

The curing catalyst used can also be a phosphine, for example triphenylphosphine.

Another type of curing catalyst is a peroxide which can be used, for example, to cure a gel coating for a fiberglass article.

The novel coating compositions can also be radiation-curable coating compositions. In this case, the binder essentially comprises monomeric or oligomeric compounds containing ethylenically unsaturated bonds, which after application are cured by actinic radiation, i.e. converted into a crosslinked, high molecular weight form. Where the system is UV-curing, it generally contains a photoinitiator as well. Corresponding systems are described in the above-mentioned publication Ullmann's Encyclopedia of Industrial Chemistry, 5th Edition, Vol. A18, pages 451–453. In radiation-curable coating compositions, the novel stabilizers can also be employed without the addition of sterically hindered amines.

The novel coating compositions according to the invention can be applied to any desired substrates, for example to metal, wood, plastic, fibergalss or ceramic materials. The coating compositions can be pigmented mono-coats or multi-layer (primer/basecoat/clearcoat) systems typical of automotive finishes. In the latter case, the novel coating composition can be used for either the base coat, or clear coat, or for both layers. If the topcoat of an automotive finish comprises two layers, of which the lower layer is pigmented and the upper layer is not pigmented, the novel coating composition can be used for either the upper or the lower layer or for both layers, but preferably for the upper topcoat layer.

The novel coating compositions can be applied to the substrates by the customary methods, for example by brushing, spraying, pouring, dipping or electrophoresis; see also Ullmann's Encyclopedia of Industrial Chemistry, 5th Edition, Vol. A18, pp. 491–500.

Depending on the binder system, the coatings can be cured at room temperature or by heating. Thermosettig coatings are preferably cured at 50–150° C. and, in the case of powder coatings, even at higher temperatures.

The coatings obtained in accordance with the invention have excellent resistance to the damaging effects of light, oxygen and heat; particular mention should be made of the good light stability and weathering resistance of the coatings thus obtained, for example paints.

The invention therefore also relates to a coating, in particular a paint, which has been stabilized against the damaging effects of light, oxygen and heat by a content of the compound of the formula (I), (II) or (III) according to the invention. The paint can be a pigmented mono-coat which comprises a film-forming binder and an organic pigment or dye, an inorganic pigment, a metallic pigment, or a mixture thereof. The paint may also be a composition which comprises a primer in adhesion to a metal or plastic substrate; a pigmented basecoat that is in adhesion to the primer and which comprises a film-forming binder and an organic pigment or dye, an inorganic pigment, a metallic pigment, or a mixture thereof; and a clear coat that is in adhesion to the base coat and which comprises a film-forming binder and optionally a transparent pigment. One especially preferred use is a paint which is a clear topcoat for automobile original equipment manufacture (OEM) and/or refinish applications.

The invention furthermore relates to a process for stabilizing a coating based on polymers against damage by light, oxygen and/or heat, which comprises mixing with the coating composition a mixture comprising a compound of an amido or carbamate substituted trisaryl-1,3,5-triazine, and to the use of mixtures comprising an amido or carbamate substituted trisaryl-1,3,5-triazine compound in coating compositions as stabilizers against damage by light, oxygen and/or heat.

The coating compositions can comprise an organic solvent or solvent mixture in which the binder is soluble. The coating composition can otherwise be an aqueous solution or dispersion. The vehicle can also be a mixture of organic solvent and water. The coating composition maybe a high-solids paint or can be solvent-free (e.g. a powder coating material).

The pigments can be inorganic, organic or metallic pigments. The novel coating compositions preferably contain no pigments and are used as a clearcoat.

Likewise preferred is the use of the coating composition as a topcoat for applications in the automobile industry, especially as a pigmented or unpigmented topcoat of the paint finish. Its use for underlying coats, however, is also possible.

The amido or carbamate triazines of this invention may be applied topically by polishing a surface with a composition comprising the amido or carbamate triazines and an inert carrier such as solvent, petroleum jelly, silicone oil in water emulsions, or automotive paint wax, e.g. Carnauba wax. These topical treatment compositions may be used to stabilize coating films, fabrics, leather, vinyl and other plastics and wood.

Preference is also given to the use of the novel amido or carbamate substituted trisaryl-1,3,5-triazine compounds in photographic materials as stabilizer against damage by light, especially by UV light. The invention therefore also relates to a photographic material comprising an amido or carbamate substituted trisaryl-1,3,5-triazine compound.

The compounds according to the invention can be used for photosensitive materials of all kinds. For example, they can be employed for color paper, color reversal paper, direct-positive color material, color negative film, color positive film, color reversal film and other materials. They are preferably used, inter alia, for photosensitive color material which comprises a reversal substrate or which forms positives.

Furthermore, the novel compounds can be combined with other UV absorbers, especially those which are dispersible in aqueous gelatin, for example with hydroxyphenylbenzotriazoles (cf. for example U.S. Pat. No. 4,853,471, U.S. 4,973,702, U.S. 4,921,966 and U.S. 4,973,701), benzophenones, oxanilides, cyanoacrylates, salicylates, or acrylonitriles or thiazolines. In this context it is advantageous to employ these further, oil-dissolved UV absorbers in the photographic material in layers other than those comprising the novel UV absorbers.

In particular, it is possible successfully to stabilize photographic materials similar to those described in U.S. Pat. No. 4,518,686.

The invention therefore additionally relates to a photographic material comprising, on support, a blue-sensitive, a green-sensitive and/or a red-sensitive silver-halide emulsion layer and, if desired, a protective layer, with a layer comprising a UV absorber being arranged above the uppermost silver-halide emulsion layer, wherein the UV absorber is an amido or carbamate substituted trisaryl-1,3,5-triazine compound.

Preference is additionally given to photographic materials which have a layer comprising a compound of the formula (I), (II) or (III) above the uppermost silver-halide emulsion layer and/or between the green- and red-sensitive silver-halide emulsion layers.

Furthermore, it may be advantageous for all or some of the said layers which can comprise a UV absorber to have a UV absorber mixture and/or a further UV absorber which is dispersible in aqueous gelatin, but a compound of the formula (I), (II) or (III) must be present at least in one layer.

The novel material preferably has gelatin interlayers between the silver-halide emulsion layers.

Preference is given to photographic materials in which the silver halide in the bluesensitive, green-sensitive and/or red-sensitive layer is silver chloride bromide comprising at least 90 mol % of silver chloride.

The compounds of the formula (I), (II) or (III) which are used in accordance with the invention can be incorporated, alone or together with the color coupler and, if used, further additives, into the color photographic materials by dissolving the compounds beforehand in high-boiling organic solvents. It is preferred to use solvents which boil at higher than 160° C. Typical examples of such solvents are the esters of phthalic acid, phosphoric acid, citric acid, benzoic acid or of fatty acids and also alkylamides and phenols.

Preferred color couplers for use in the compositions of the invention, examples of such compounds, further additives such as color cast inhibitors, DIR couplers and further light stabilizers, such as UV absorbers, phenols, phosphorus (III) compounds, organometallic complexes, hydroquinones and hydroquinone ethers, and more precise details on the structure of various photographic materials, can be found, for example, in the publications EP-A-0531258 and EP-A-0520938 and in the literature cited therein.

The amido or carbamate substituted trisaryl-1,3,5-triazine compounds of the formula (I), (II) or (III) are suitable for the photochemical stabilization of undyed, dyed or printed fiber materials comprising for example, silk, leather, wool, polyamide or polyurethanes and especially cellulose-containing fiber materials of all kinds. Examples of such fiber materials are the natural cellulose fibers, such as cotton, linen, jute and hemp and also viscose staple fiber and regenerated cellulose. Preferred textile fiber materials are those of cotton. The triazine compounds of the present invention are also suitable for the photochemical stabilization of hydroxyl-containing fibers in blend fabrics, for example blends of cotton with polyester fibers or polyainide fibers. A further preferred area of application relates to the blocking or reduction of the UV radiation which passes through the above-mentioned textile materials (UV cutting) and the heightened sun protection which textile materials finished with a novel compound offer to the human skin.

To this end, one or a number of different compounds of the formula (I), (II) or (III) are applied to the textile fiber material by one of the customary dyeing methods, advantageously in a quantity of 0.01 to 5% by weight, preferably 0.1 to 3% by weight and, in particular, from 0.25 to 2% by weight, based on the weight of the fiber material. The amido or carbamate substituted trisaryl-1,3,5-triazine compounds can be applied to the fiber material in various ways and fixed on the fiber, especially in the form of aqueous dispersions or printing pastes.

The textile fiber materials finished with the novel compounds of the formula (I), (II) or (III) possess improved protection against photochemical breakdown of the fiber and yellowing phenomena and, in the case of dyed fibre material, are of enhanced (hot) light fastness. Particular emphasis should be drawn to the greatly improved photoprotective effect of the treated textile fiber material and, in particular, the good protective effect with respect to short-wave UV-B rays. This is manifested by the fact that the textile fiber material finished with an amido or carbamate substituted trisaryl-1,3,5-triazine compound has, relative to untreated fabric, a greatly increased sun protection factor (SPF).

The sun protection factor is defined as the quotient of the dose of UV radiation which damages protected skin to that which damages unprotected skin. Accordingly, a sun protection factor is also a measure of the extent to which untreated fiber materials and fiber materials treated with a novel compound of the formula (I), (II) or (III) are permeable to UV radiation. The determination of the sun protection factor of textile fiber materials is explained, for example, in WO94/04515 or in J. Soc. Cosmet. Chem. 40, 127–133(1989) and can be carried out analogously thereto.

Yet another use of the UV absorbers according to the invention is in the stabilization of intra-ocular and contact lenses.

The UV absorbers according to the invention are suitable, furthermore, as photoprotective agents in cosmetic preparations. The invention additionally relates, therefore, to a cosmetic preparation comprising at least one amido or carbamate substituted trisaryl-1,3,5-triazine compound and cosmetically acceptable carriers or auxiliaries.

The novel cosmetic composition contains from 0.1 to 15% by weight, preferably from 0.5 to 10% by weight, based on the overall weight of the composition, of an amido or carbamate substituted trisaryl-1,3,5-triazine UV absorber and a cosmetically acceptable auxiliary.

The cosmetic composition can be prepared by physically mixing the novel UV absorber with the auxiliary by means of customary methods, for example by simply stirring together the two materials.

The cosmetic preparation according to the invention can be formulated as a water-in-oil or oil-in-water emulsion, as an oil-in-oil alcohol lotion, as a vesicular dispersion of an ionic or nonionic amphiphilic lipid, as a gel, solid stick or as an aerosol formulation.

As a water-in-oil or oil-in-water emulsion, the cosmetically acceptable auxiliary preferably contains from 5 to 50% of an oily phase, from 5 to 20% of an emulsifier and from A 30 to 90% water. The oil phase mentioned can comprise any oil which is suitable for cosmetic formulations, for example one or more hydrocarbon oils, a wax, a natural oil, a silicone oil, a fatty acid ester or a fatty alcohol. Preferred mono- or polyols are ethanol, isopropanol, propylene glycol, hexylene glycol, glycerol and sorbitol.

For the cosmetic formulations according to the invention it is possible to use any conventionally employed emulsifier, for example one or more ethoxylated esters of naturally occurring derivatives, for example polyethoxylated esters of hydrogenated castor oil; or a silicone oil emulsifier such as silicone polyol; an unmodified or ethoxylated fatty acid soap; an ethoxylated fatty alcohol; an unmodified or ethoxylated sorbitan ester; an ethoxylated fatty acid; or an ethoxylated glyceride.

The cosmetic formulation can also comprise further components, for example emollients, emulsion stabilizers, skin moisteners, tanning accelerators, thickeners such as xanthan, moisture retention agents such as glycerol, preservatives, or fragrances and colorants.

The novel cosmetic formulations are notable for good protection of human skin against the damaging effect of sunlight while at the same time providing for reliable tanning of the skin.

The invention will now be illustrated by the following examples. The examples are not intended to be limiting of the scope of the present invention. In conjunction with the general and detailed descriptions above, the examples provide further understanding of the present invention.

EXAMPLES

Preparation of Compound A (Intermediate)

2-(2-hydroxy-4-ethoxycarbonylmethoxyphenyl)-4,6-bis(2,4-dimethylphenyl)-1,3,5-triazine (Compound "A") was synthesized using the following reaction scheme:

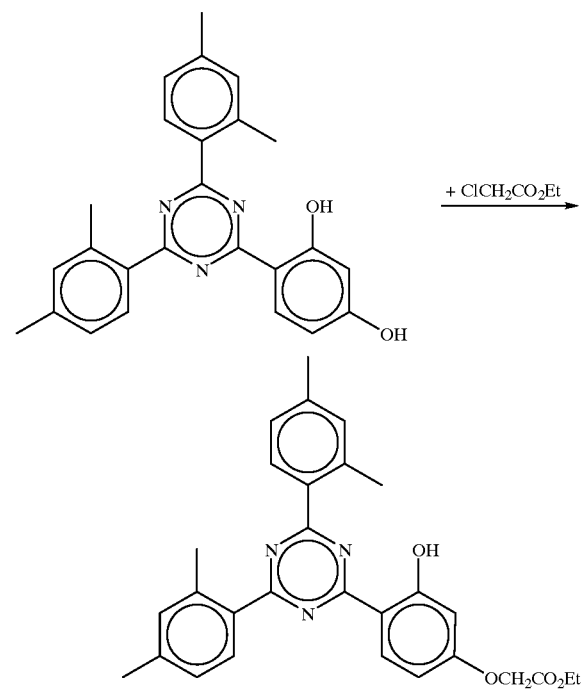

The following were added, from first to last, to a 2 neck round bottom flask equipped with a magnetic stirring bar, a reflux condenser, an argon inlet and a rubber septum:

8.0 g of 2,4-bis(2,4-dimethylphenyl)-6-(2,4-dihydroxyphenyl)-1,3,5-triazine, 6.92 g of anhydrous $K_2CO_3$, 50 ml of acetone, 2.7 g ethyl chloroacetate and 332 mg potassium iodide.

The reaction mixture was stirred for 2 h as its temperature was gradually increased to 40° C. Then the temperature was rapidly increased to 60° C. and the mixture was further stirred for 7 h. Thin layer chromatography (hereafter "tlc") analysis after the 7 h stirring indicated the presence of Compound A and no starting triazine material. The reaction mixture was cooled to room temperature, diluted with 50 ml of methylene chloride, then filtered through Celite. The filter cake was washed with methylene chloride. The combined filtrates were concentrated at reduced pressure to yield 10.4 g of crude Compound A which was crystallized from a methylene chloride-methanol mixed solvent to give 8.7 g of a substantially pure product, as determined by $^1$H NMR, $^{13}$C NMR and mass spectroscopy.

Preparation of Compound B (Comparative)

4-[4,6-Bis(2'4'-dimethylphenyl)-1,3,5-triazin-2-yl]-3-hydroxyphenoxyacetic acid, N-(2-hydroxyethyl)amide (Compound "B"); also known as 2-[2-hydroxy-4-(N-2-hydroxyethyl)-methanamidooxy)phenyl]-4,6-bis(2,4-dimethylphenyl)-1,3,5-triazine) was synthesized using the following reaction scheme:

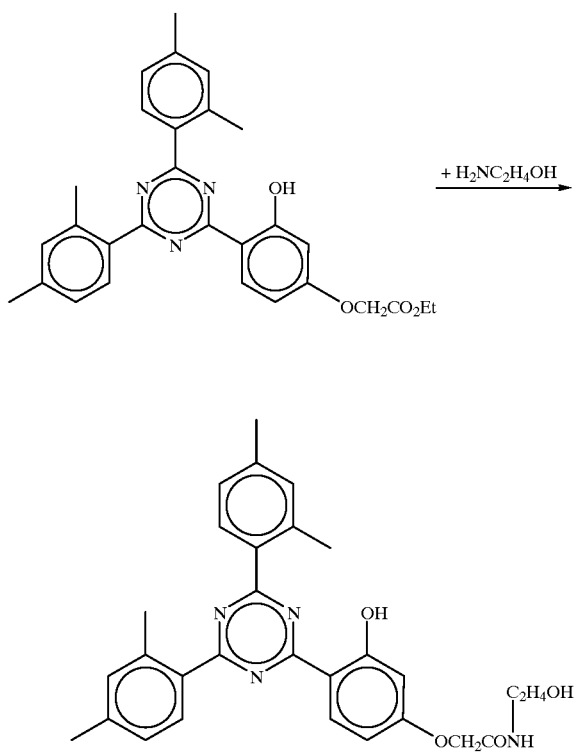

The following were added, from first to last, to a 2 neck round bottom flask equipped with a magnetic stirring bar, a reflux condenser, an argon inlet and a rubber septum:

4.83 g of Compound A,
30 ml of xylene,
3.0 ml of ethanolamine and
122 mg of 4-dimethylaminopyridine ("DMAP") as catalyst.

The reaction mixture was heated to reflux and refluxed for 5 h; at this time, tlc analysis indicated the presence of Compound B product and no starting Copound A material. The reaction mixture was cooled to room temperature and diluted with hexane. The precipitate thus formed was filtered then washed with hexane. The precipitate was further purified by stirring with methanol, filtered, then dried under reduced pressure to give 4.9 g of a substantially pure product determined to be Compound B by $^1$H NMR, $^{13}$C NMR and mass spectroscopy.

Preparation of Compound C

4-[4,6-Bis(2'4'-dimethylphenyl)-1,3,5-triazin-2-yl]-3-hydroxyphenoxyacetic acid, N, N-bis(2-hydroxyethyl) amide (Compound "C"), also known as 2-[2-hydroxy-4-(N, N-bis-hydroxyethyl)-methanamidooxy)phenyl]-4,6-bis(2,4-dimethylphenyl)-1,3,5-triazine) was synthesized using the following reaction scheme:

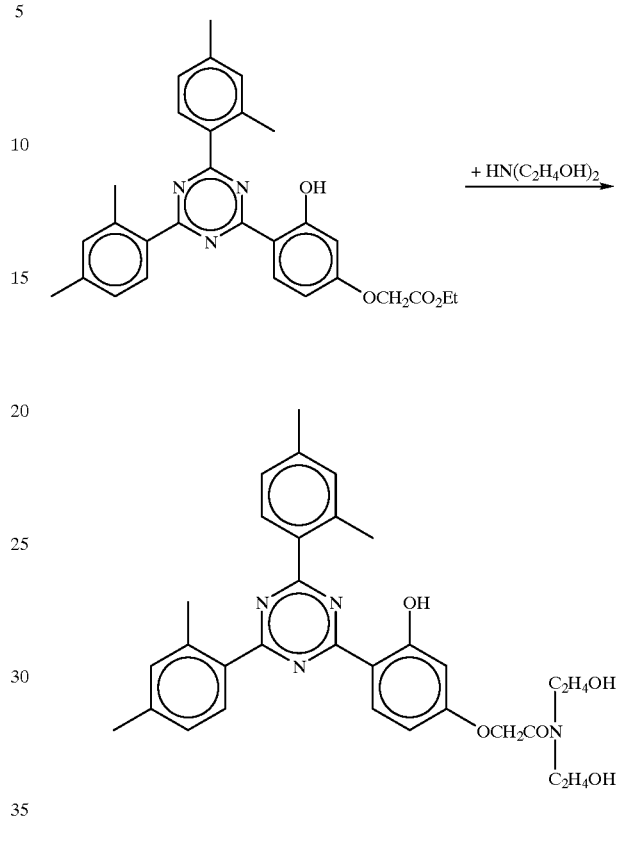

The following were added, from first to last, to a 2 neck round bottom flask equipped with a magnetic stirring bar, a reflux condenser, an argon inlet and a glass stopper:

966 mg of Compound A,
10 ml of xylene,
460 mg of diethanolamine and
25 mg DMAP catalyst.

The reaction mixture was heated to reflux and refluxed for 20 h; at this time, tlc analysis indicated the presence of Compound C product and no starting Compound A material. The reaction mixture was cooled to room temperature and filtered as described above, redissolved in methylene chloride and precipitated by adding hexane. The precipitates thus formed were filtered, washed with hexane and dried under reduced pressure to give 1.0 g of a substantially pure product determined to be Compound C by $^1$H NMR, $^{13}$C NMR and mass spectroscopy.

Preparation of Compound D

4-[4,6-Bis(2'4'-dimethylphenyl)-1,3,5-triazin-2-yl]-3-hydroxyphenoxyacetic acid, N-ethyl-N-(2-hydroxyethyl) amide (Compound "D"), also known as 2-[2-hydroxy-4-(N-ethyl-N-(2-hydroxyethyl)-methanamidooxy)phenyl]-4,6-bis (2,4-dimethylphenyl)-1,3,5-triazine) was synthesized using the following reaction scheme:

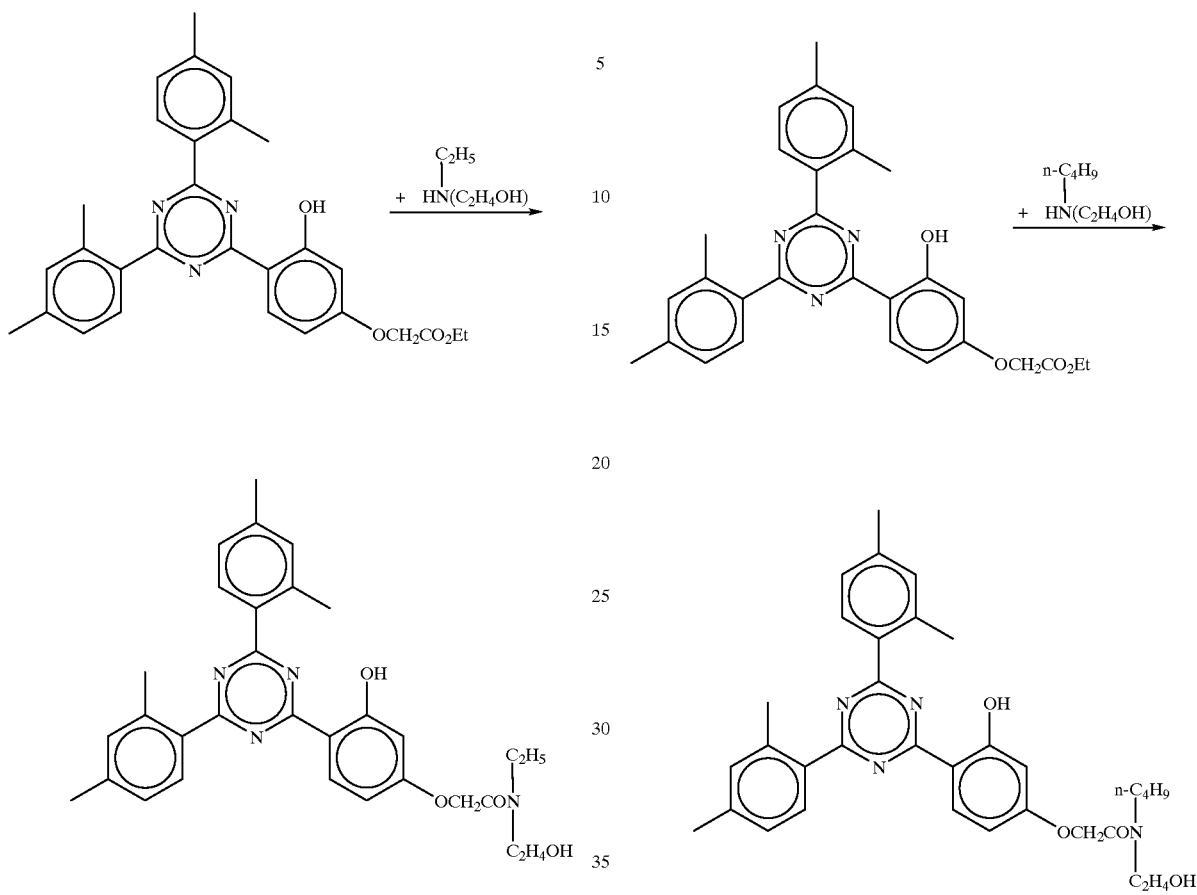

The following were added, from first to last, to a 2 neck round bottom flask equipped with a magnetic stirring bar, a reflux condenser, an argon inlet and a glass stopper:
- 9.66 g of Compound A,
- 60 ml of xylene,
- 4.9 ml of N-ethylethanolamine and
- 244 mg of DMAP catalyst.

The reaction mixture was heated to reflux and refluxed for 8 h; at this time, tlc analysis indicated the presence of the Compound D product and no starting Compound A material. The reaction mixture was cooled to room temperature and filtered as described above, redissolved in methylene chloride and precipitated by adding hexane. The precipitates thus formed were filtered, washed with hexane and dried under reduced pressure to give 10.1 g of a substantially pure product determined to be Compound D by $^1$H NMR, $^{13}$C NMR and mass spectroscopy.

Preparation of Compound E

4-[4,6-Bis(2'4'-dimethylphenyl)-1,3,5-triazin-2-yl]-3-hydroxyphenoxyacetic acid, N-(n-butyl)-N-(2-hydroxyethyl)amide (Compound "E"); also known as 2-[2-hydroxy-4-(N-(n-butyl)-N(2-hydroxyethyl)-methanamidooxy)phenyl]4,6-bis(2,4dimethylphenyl)-1,3,5-triazine) was synthesized using the following reaction scheme:

The following were added, from first to last, to a 2 neck round bottom flask equipped with a magnetic stirring bar, a reflux condenser, an argon inlet and a glass stopper:
- 4.83 g of Compound A,
- 30 ml of xylene,
- 1.75 g of n-butylethanolamine and
- 122 mg of DMAP catalyst.

The reaction mixture was heated to reflux and refluxed for 6 h; at this time, tlc analysis indicated the presence of the Compound E product and no starting Compound A material. The reaction mixture was cooled to room temperature and diluted with hexane. The precipitates thus formed were filtered, stirred with 100 ml of methanol, filtered and dried under reduced pressure to give 5.3 g of a substantially pure product determined to be Compound E by $^1$H NMR, $^{13}$C NMR and mass spectroscopy.

Preparation of Compound F

The adduct of Compound E with 1-(2-isocyanopropyl)-3-propenylbenzene ("m-TMI") was prepared using the following reaction scheme:

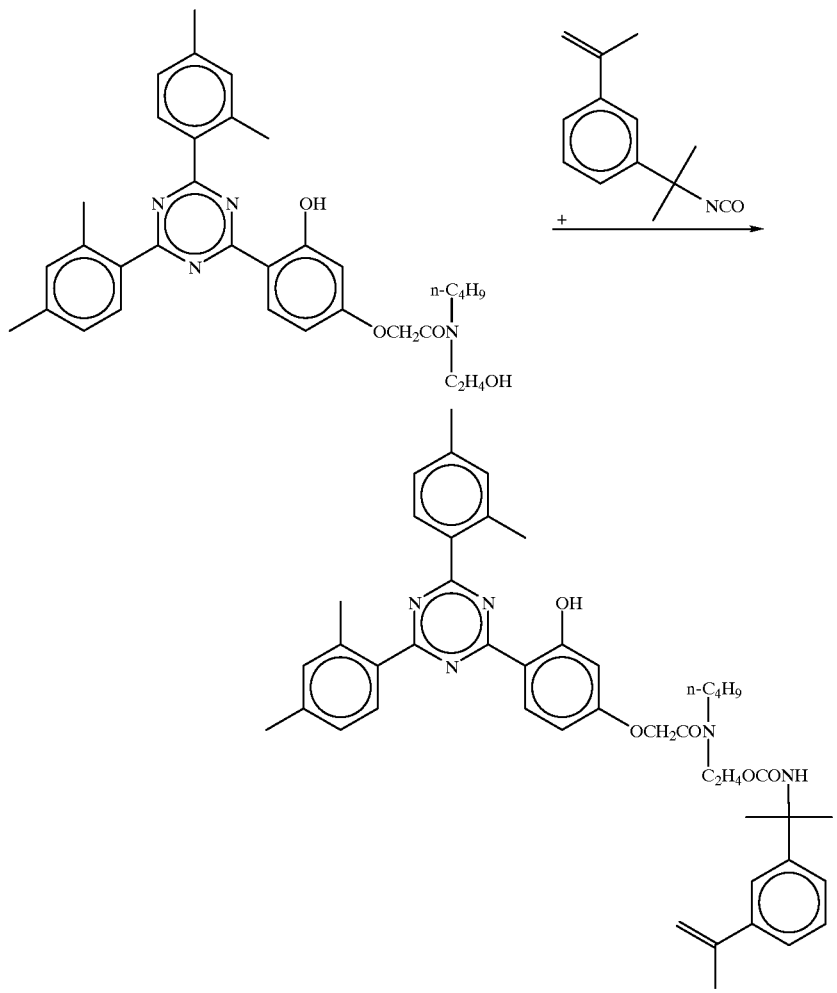

The following were added to a 2 neck round bottom flask equipped with a magnetic stirring bar, a reflux condense, an argon inlet and a glass stopper:

- 5.55 g of Compound E,
- 40 ml of xylene,
- 2.01 g of m-TMI and
- 75 mg of 1,3-diacetoxy-1,1,3,3-tetrabutyldistannoxane ("TK-1") catalyst.

The reaction mixture was heated for 6 h at 120° C.; at this time, tlc analysis indicated the presence of the Compound F product and no starting Compound E material. The reaction mixture was cooled to room temperature and concentrated under reduced pressure to give 7.5 g of crude product. An analytical sample, prepared by purifying the crude product using column chromatography over silica gel, was determined to be Compound F by $^1$H NMR, $^{13}$C NMR and mass spectroscopy.

Preparation of Compound G

2-{4-[4,6-bis(2'4'-dimethylphenyl)-1,3,5-triazin-2-yl]-3-hydroxyphenoxy}-eth-1-yl N-(meta-isopropenyl-α,α-dimethylbenyzl) carbamate (Compound "G") was synthesized using the following reaction scheme:

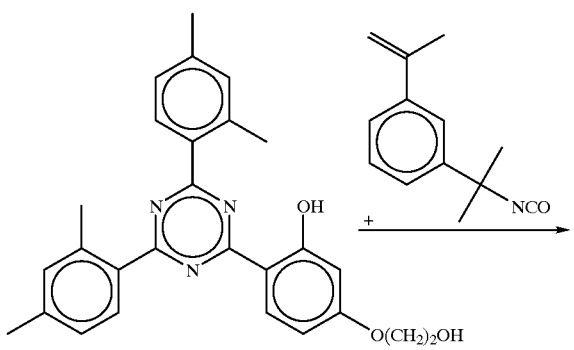

-continued

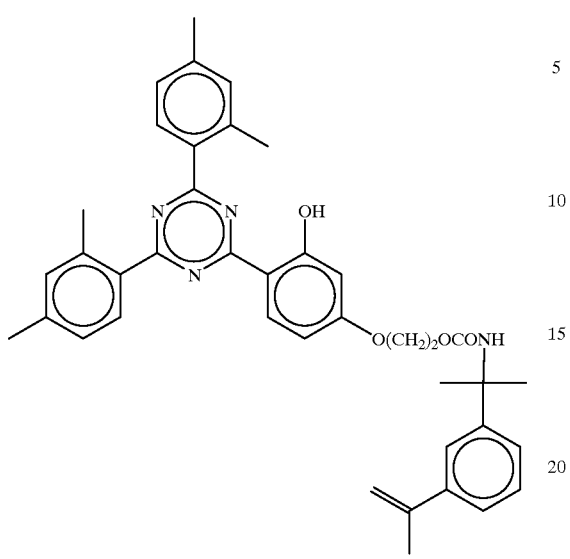

-continued

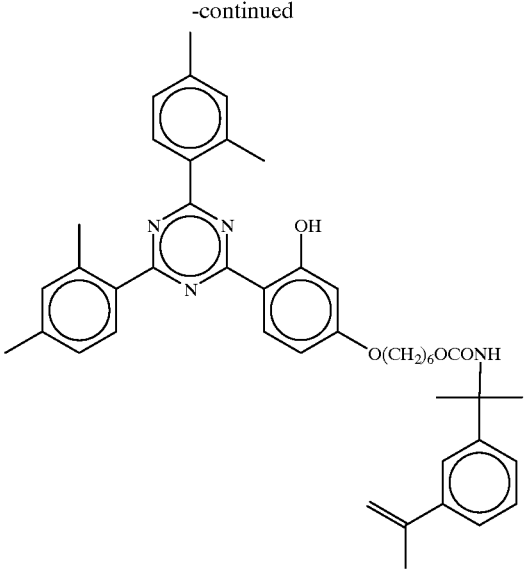

The following were added, from first to last, to a 2 neck round bottom flask equipped with a magnetic stirring bar, a reflux condenser, an argon inlet and a glass stopper:

- 5.55 g of 2,4-bis(2,4-dimethylphenyl)-6-[2-hydroxy-4-(6-hydroxyethyloxy)phenyl]-1,3-5-triazine ("HET"),
- 40 ml of xylene,
- 4.02 g of m-TMI and
- 120 mg of TK-1 catalyst.

The reaction mixture was heated for 6 h at 120° C.; at this time, tlc analysis indicated the presence of the Compound G product and no HET starting material. The reaction mixture was cooled to room temperature and concentrated under reduced pressure to give 12.95 g of crude product. An analytical sample, prepared by purifying the crude product using column chromatography over silica gel, was determined to be Compound G by $^1$H NMR, $^{13}$C NMR and mass spectroscopy.

Preparation of Compound H

6-{4-[4,6-Bis(2'4'-dimethylphenyl)-1,3,5-triazin-2-yl]-3-hydroxyphenoxy}-hex-1-yl N-(meta-isopropenyl-α,α-dimethylbenyzl) carbamate (Compound "H") was synthesized using the following reaction scheme:

The following were added, from first to last, to a 2 neck round bottom flask equipped with a magnetic stirring bar, a reflux condenser, an argon inlet and a glass stopper:

- 4.97 g of 2,4-bis(2,4-dimethylphenyl)-6-[2-hydroxy-4-(6-hydroxyhexyloxy)phenyl]-1,3-5-triazine ("HHT"),
- 40 ml of xylene,
- 2.01 g of m-TMI and
- 75 mg of TK-1 catalyst.

The reaction mixture was heated for 6 h at 120° C.; at this time, tlc analysis indicated the presence of the Compound H product and no starting HHT material. The reaction mixture was cooled to room temperature and concentrated under reduced pressure to give 7 g of crude product. An analytical sample, prepared by purifying the crude product using column chromatography over silica gel, was determined to be Compound H by $^1$H NMR, $^{13}$C NMR and mass spectroscopy.

Preparation of Compound I

6-{4-[4,6-Bis(2'4'-dimethylphenyl)-1,3,5-triazin-2-yl]-3-hydroxyphenoxy}-hex-1-yl carbamate)phenyl]-1,3,5-triazine (Compound "I"), also known as 2,4-bis(2,4-dimethylphenyl)-6-[2-hydroxy-4-(6-carbamoyloxyhexyloxy)phenyl]-1,3-5-triazine) was synthesized using the following reaction scheme:

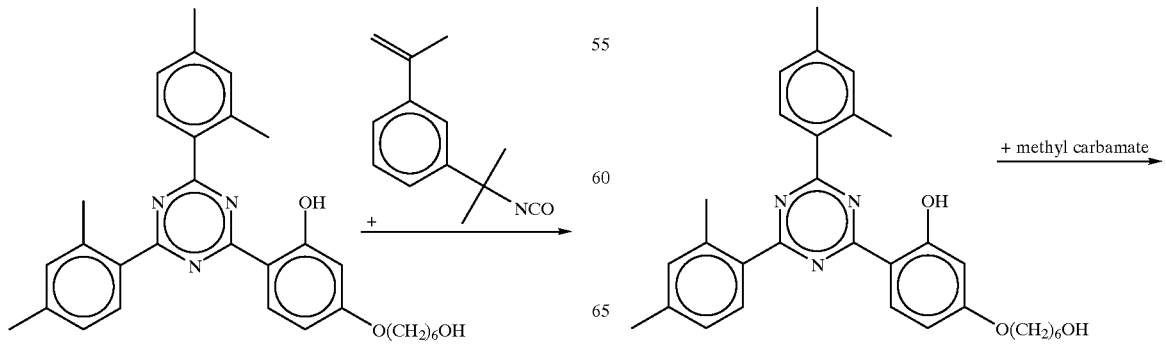

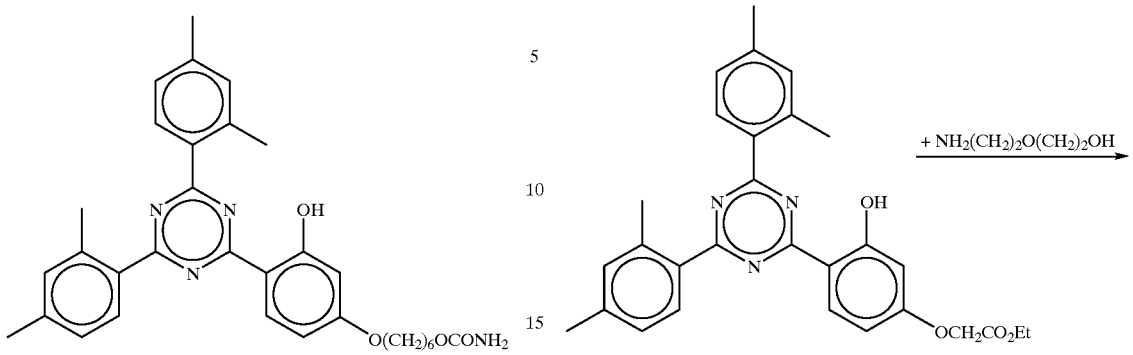

The following were added, from first to last, to a 250 ml round-bottom flask equipped with a magnetic stir bar and a distillation head connected to a distillation condenser:

30.0 g of HHT (0.060 mol),
36.2 g of methyl carbamate ("MEC", 0.48 mol),
100 ml of toluene and
0.26 g of TK-1 (0.43 mmol).

The mixture was heated for 3.5 hours at an oil-bath temperature (ca. 135° C.) such that slow distillation of ca. 50 ml of toluene/methanol occurred. The resulting mixture was allowed to cool and the solid mass dissolved in 800 ml of $CHCl_3$. This solution was extracted eight times, each time with 220 ml of water, then extracted once with 220 ml of brine. The organic layer was dried over magnesium sulfate, filtered and rotary evaporated, giving a yellow solid. The solid was dissolved in boiling acetone, cooled to room temperature and placed in a refrigerator at −15° C. for 1 day. The product, which separated as a solid, was isolated by filtration and vacuum oven dried for 18 hours at 47–53° C. affording 94.4 g (89.4% of theoretical yield) of Compound I as a pale yellow solid with a melting point of 147–150° C.

Preparation of Compound J

4-[4,6-Bis(2,4-dimethylphenyl)-1,3,5-triazin-2-yl]-3-hydroxypenoxyacetic acid, N-(2-(2-hydroxyethoxy)ethyl) amide (Compound "J"), also known as 2-[2-hydroxy-4-(N-(2-(2-hydroxyethoxy)ethyl)-methanamidooxy)phenyl]-4,6-bis(2,4-dimethylphenyl)-1,3,5-triazine was synthesized using the following reaction scheme:

The following were added, from first to last, to a 2 neck round bottom flask equipped with a magnetic stirring bar, a reflux condenser, an argon inlet, and a rubber septum:

50 g of Compound A,
250 mL of xylene,
21 g-2-(2-aminoethoxy)ethanol and
0.9 g of DMAP catalyst.

The reaction mixture was heated to reflux. An additional 10.5 g of 2-(2-aminoethoxy)ethanol and 0.9 g DMAP was added during the course of the reaction. After 34 hours at reflux, the reaction mixture was allowed to cool to room temperature and diluted with hexane. The precipitated material was filtered, washed with hexane and dried under reduced pressure to give 56 g of a substantially pure product determined to be Compound J on the basis of $^1$H NMR and mass spectroscopy.

Preparation of Compound K

4-[4,6-Bis(2,4-dimethylphenyl)-1,3,5-triazin-2-yl]-3-hydroxypenoxyacetic acid, N-(2-acryloyloxy)ethyl)amide (Compound "K"), also known as 2-[2[hydroxy-4-(N-(2-acryloyloxy)ethyl)-methanamidooxy)phenyl]-4,6-bis(2,4-dimethylphenyl)-1,3,5-triazine was synthesized using the following reaction scheme:

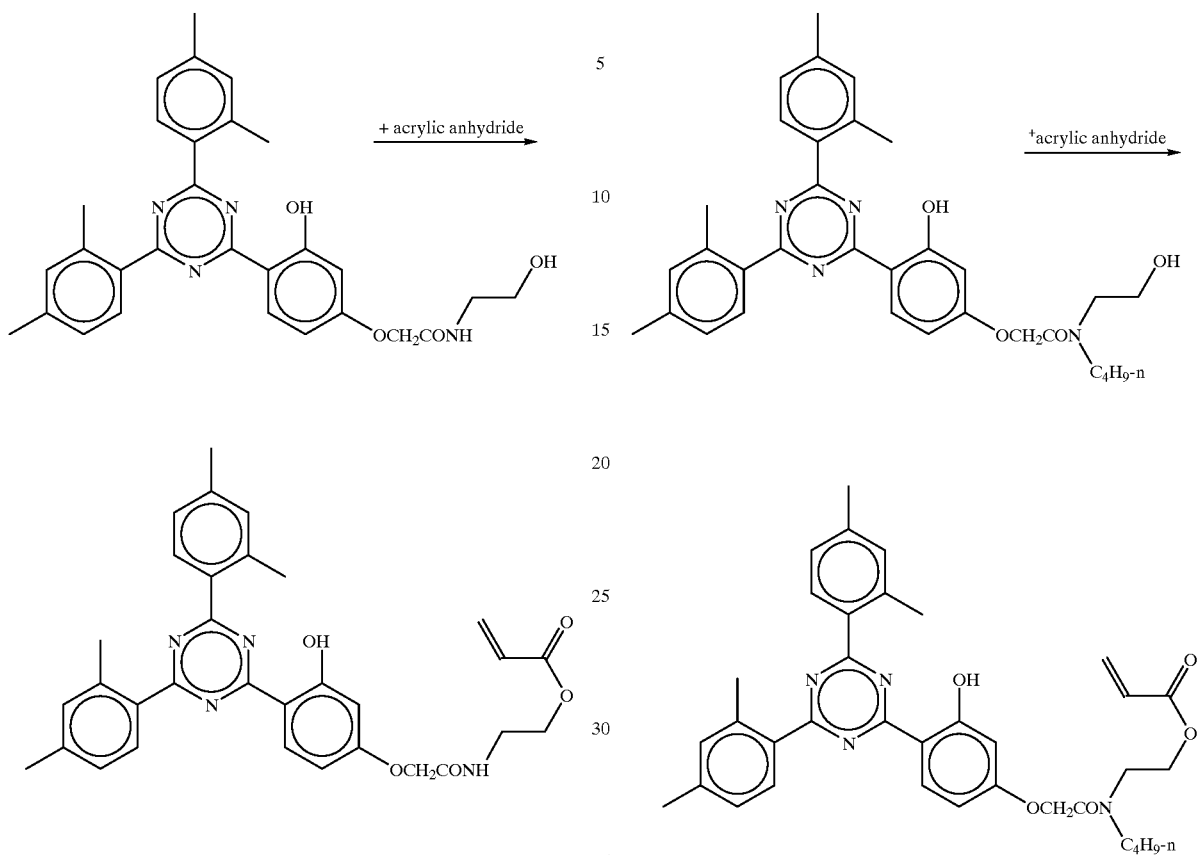

The following were added, from first to last, to a 2 neck round bottom flask equipped with a magnetic stirring bar, a reflux condenser, an argon inlet, and a rubber septum:
- 498 mg of Compound B,
- 5 mL of pyridine, and
- 250 mg of acrylic anhydride The mixture was stirred at room temperature for 24 h, and then poured onto crushed ice. The mixture was stirred for 1 hr, and extracted with methylene chloride. The organic layer was washed with water, dried over anhydrous sodium sulfate, filtered, and concentrated under reduced pressure to give 450 mg of a substantially pure product determined to be Compound K on the basis of $^1$H NMR and mass spectroscopy.

Alternate Procedure for the Preparation of Compound K

Compound K was also prepared by reaction of Compound B and acrylic acid in xylenes at 130° C. for 24 h. The reaction mixture was then concentrated under reduced pressure. TLC analysis showed the presence of Compound B as well as the formation of a new spot that corresponded to Compound K (by direct comparison of TLC retention times to an authentic sample prepared by the above reaction of Compound B with acrylic anhydride).

Preparation of Compound L

4-[4,6-Bis(2,4-dimethylphenyl)-1,3,5-triazin-2-yl]-3-hydroxypenoxyacetic acid, N-(n-butyl)-N-(2-acryloyloxy)ethyl)amide (Compound "L"), also known as 2-[2-hydroxy-4-(N-(n-butyl)-N-(2-acryloyloxy)ethyl)-methanamidooxy)phenyl]-4,6-bis(2,4-dimethylphenyl)-1,3,5-triazine was synthesized using the following reaction scheme:

The same procedure used for the preparation of Compound K using acrylic anhydride was followed. The product was determined to be substantially pure Compound L on the basis of $^1$H-NMR spectroscopy.

Example 1 and Comparative Example 1

Solubility

Compound E (the disubstituted amide) was compared against Compound B (the monosubstituted amide) for solubility in a 1:1:1 mixture of xylenes:methyl amyl ketone (MAK):propylene glycol methyl ether acetate (PM acetate), which is a typical coatings solvent mixture. The results are presented below in Table I:

TABLE 1

Solubility of Amide-Containing Triazines in the Solvent Mixture (1:1:1 Xylenes:MAK:PM Acetate)

| Stabilizer | Concentration wt % | Solubility 23° C. | 50° C. | 5° C. |
|---|---|---|---|---|
| CEX1 (B) | 5 | No | No | No |
| EX1 (E) | 5 | Yes | Yes | Yes |
| EX1 (E) | 10 | Yes | Yes | Yes |

As can be seen from these results, Compound E fully dissolved in the solvent mixture even at 10 wt %, and did not crystallize out of solution at 5° C. Compound B, on the other hand, did not dissolve, even at 5 wt % and at 50° C.

Example 2 and Comparative Example 2
Compatibility

Compound E was again compared against Compound B, this time for compatibility in the following resin formulation which is the polyol component of a typical two-component acrylic urethane clearcoat formulation:

100 parts Acrylic Resin—JONCRYL® CDX-588 (70% Solids) (S. C. Johnson & Son, Inc., Racine, Wis.
5 parts—1 part Dibutyltin Dilaurate (T-12, Air Products, Allentown, Pa.)
Catalyst Solution
45 parts Solvent Mixture (1:1:1 xylenes:MAK:PM Acetate)
1 part Hindered Amine Light Stabilizer (SANDUVOR® S-3055, Clariant Corp., Charlotte, N.C.).

The results are presented below in Table 2.

TABLE 2

Compatibility of Triazines with Acrylic Urethane Component I

| Stabilizer | Conc. (wt %)[a] | Compatibility | | |
|---|---|---|---|---|
| | | 23° C. | 60° C. | 5° C. |
| CEX1 (B) | 1 | No | No | No |
| EX1 (E) | 1 | Yes | Yes | Yes |
| EX1 (E) | 2 | Yes | Yes | Yes |

[a]Based on total resin solids in final formulation (both components)

As can be seen from the results, Compound E was compatible with the resin component as it fully dissolved even at 5° C. Compound B, on the other hand, was not compatible at either 5° C., 23° C. or 60° C.

Addition of DESMODUR® N-3390 (Bayer Corp.) and an additional 17 parts of the solvent mixture (a polyisocyanate crosslinker component of a typical two-component acrylic urethane clearcoat formulation) to the formulations set forth above did not result in the dissolution of Compound B in the fully formulated coating, nor did it adversely affect the compatibility of Compound E with the fully formulated coating.

Example 3
Bonding of Compound E to Acrylic/Melamine Resin Matrix

Compound E was investigated to determine whether it forms a chemical bond with the acrylic/melamine resin matrix during curing. For this purpose, it was added to a clearcoat formulation and coated onto a plastic substrate, as described below. Non-bondable UV absorbers readily migrate from clearcoats into plastic substrates upon curing the coating. An absorber which bonds to the matrix should not migrate into the plastic substrate to any significant extent.

The acrylic/melamine resin formulation utilized was as follows:

40.6 g JONCRYL® 510 acrylic resin (S.C. Johnson, Inc. Racine, Wis.)
17.5 g CYMEL® 303 crosslinker (Cytec Industries, Inc., West Paterson, N.J.)
0.52 g CYCAT® 4040 catalyst (Cytec Industries, Inc., West Paterson, N.J.)
10.0 g n-Butanol
0.50 g DC 57 flow control agent
8.0 g xylene To this formulation was added 3% of Compound E based on total resin solids.

The resulting coating was drawn onto plastic RIM substrates (Dow SPECTRIM® 50) using a #58 cator rod and cured for 30 minutes at 135° C. After cure, the coating and part of the substrate were microtomed into 10 μm thick slices parallel to the coating surface. The microtome was a Reichert-Jung Polycut E instrument. Each microtomed slice was mounted between two microscope slides and its UV absorption spectrum measured using a Perkin-Elmer Lambda 2 spectrophotometer. The absorbance per micrometer sample thickness was determined at the prominent 340 nm absorption band intrinsic to this UVA.

The results of the UV analysis were plotted as a function of depth. The original coating surface in contact with the atmosphere was located at 0 μm. The coating/substrate interface was at about 70 μm below the surface. The total microtomed depth was about 130 μm. The plotted curve showed a steep drop of the absorbance near the coating/substrate interface, indicating that most of the Compound E molecules remained in the coating, and only minor amounts migrated through the interface into the plastic substrate. By measuring the area under the curve, the quantity of Compound E remaining in the coatings and the fraction that migrated into the substrates were estimated. The result is that about 95% of the added Compound E remained in the coating, with only about 5% migrating into the substrate.

For comparison, CYASORB® UV1164L (a non-bondable triazine UV absorber available from Cytec Industries Inc.) was found to migrate into RIM substrates. Under identical experimental conditions (30 minutes cure at 135° C.), 63% of the added non-bondable triazine UVA migrated into the substrate and only 37% was left in the coating.

Example 3A
Bonding of Compound E to a Polycarboxylic Acid

Adipic acid was chosen as a model compound to demonstrate the bonding of Compound E to poly(carboxylic acid) resin.

The following were added to a 3 neck round bottom flask equipped with a magnetic stirring bar, a Dean-Stark trap with a condenser, a thermocouple, and a nitrogen inlet:

1.0 g of Compound E
140 mg of adipic acid
20 mL of xylenes

The mixture was heated at reflux for 1.5 h. At this time HPLC analysis indicated that Compound E had completely reacted to give new compounds containing the tris-aryl-1, 3,5-triazine chromophore, as determined by HPLC analysis.

Comparative Example 3A
Bonding of HHT to a Polycarboxylic Acid: Preparation of Compound M

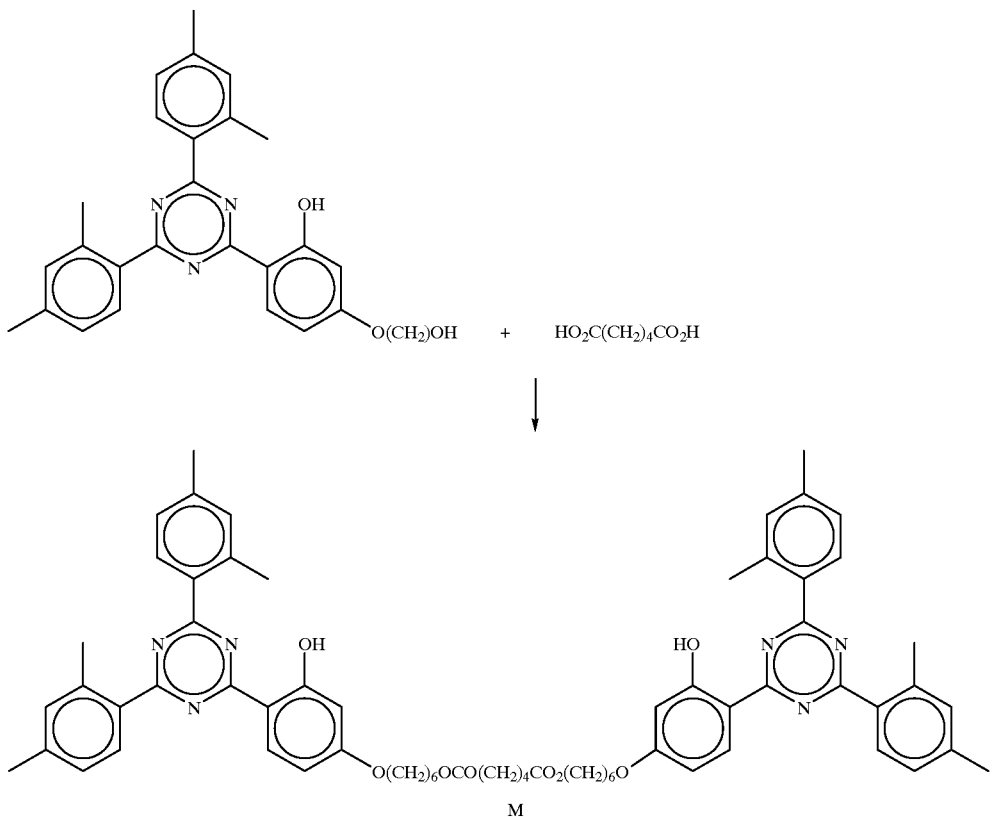

M

The following were added to a 3 neck round bottom flask equipped with a magnetic stirring bar, a Dean-Stark trap with a condenser, a thermocouple, and a nitrogen inlet:

1.0 g of HTT 161 mg of adipic acid 20 mL of xylenes

The mixture was heated at reflux for 2.5 h. At this time HPLC analysis indicated that HTT was unreacted.

Even after 73 hr. at reflux, there was only 14% conversion of HTT (based on HPLC area percent measurements at 290 nm) to a mixture of the diester (Compound M) plus the corresponding monoester.

This experiment, along with Example 3A, demonstrates the unique reactivity of the hydroxyalkyl amido substituted tris-aryl-1,3,5-triazine of the present invention compared to other current art hydroxyl substituted tris-aryl-1,3,5-triazines.

Example 4
Bonding of Compound E to Polyurethane Resin Matrix

Bonding of Compound E in a solvent based polyurethane coating was confirmed by a second experiment. The solvent based polyurethane coating used had the following formula:

| | |
|---|---|
| 103 g | JONCRYL ® CDX-588 acrylic resin (68% solids) (S. C. Johnson & Son, Inc., Racine, WI) |
| 33 g | DESMODUR ® N-3390 crosslinker (90% solids) (Bayer Corp., Pittsburgh, PA) |
| 59 g | 1:1:1 xylene:MAK:PM Acetate solvent mix |
| 5 g | T-12 catalyst. |

Compound E was added to this formulation at the 2% level.

The coating was drawin onto a block copoly(ester-ether) plastic substrate (HYTREL® DYM 100, available from E.I. duPont de Nemours and Company) used for automotive applications, witha #58 cator rod. After cure at 135° C. for 30 minutes, the coating and part of the substrate were microtomed and the microtomed slices extracted using supercritical fluid extraction. The extracts were analyzed for Compound E using HPLC. No Compound E was detected in the slices cut from the coating or from the substrate. This indicates that Compound E was chemically bonded to the resin matrix and, therefore, could not be extracted from the coating, and further that no Compound E migrated into the plastic substrate.

Example 5
Demonstration of Bonding to Compound I to a Resin Matrix

A "two-layer" approach was used to determine whether Compound I bonds to the polyurethane resin matrix of Example 4 during cure. In the two-layer technique, two coating layers of identical composition were coated on a steel substrate, with Compound I added to the top layer only in an amount of 2% based upon the solids content of the coating. The bottom layer was drawn onto the substrate using a #58 cator rod and partially cured at 120° C. for 10 minutes. The top layer was drawn onto the partially cured bottom layer using a #58 cator rod.

The bonding of Compound I was ascertained by using depth profiling similar to that described in Example 3, with the coating sample being microtomed into thin slices parallel to the coating surface. Each slice was subsequently analyzed for its stabilizer content using UV spectroscopy as in Example 3. Two different cure conditions were evaluated, 30 minutes at 80° C. and 30 minutes at 120° C. The UV absorbances of the individual microtomed slices as a function of depth from the surface in contact with the atmosphere for both cure conditions were measured. Compound I was completely absent from the bottom layer of the two-layer coating cured at 80° C. Only 5% of Compound I was present in the bottom layer of the two-layer caoting cured at 120° C.

Example 5A

Bonding of Compound E into a water-based polyurethane coating was confirmed as follows. The water-based polyurethane coating was as follows:

| | |
|---|---|
| 6.8 g | Acrylic polyol (73% in PMAc*) |
| 4.2 g | Cythane ® 3174 (74% in butyl acetate; Cytec Industries, West Paterson, NJ) |
| 0.35 g | Triethylamine |
| 0.41 g | T-12 dibutyltin dilaurate catalyst |
| 12.0 g | Water |
| 3.24 g | Compound E (5% in MEK) |

*PMAc - propylene glycol monomethyl ether acetate

To test the bondability of Compound F in the above formulation, the two-layer method of Example 5 was used. The UV absorbances of the individual microtomed slices as a function of depth from the surface in contact with the atmosphere for both cure conditions were measured. The interface between the two polyurethane layers is at 50 μm. At this interface the UV absorbance of the top layer drops essentially to zero. No UV absorbance is observed in the bottom layer demonstrating that Compound E is effectively bound to the resin of the top coating. The amount of Compound E which migrated during cure from the top paint layer into the lower layer was insignificant.

Example 5B

The bonding of Compound E in the water-borne polyurethane coating of Example 5A was confirmed in a second experiment. The resin was coated onto a Hytrel® DYM 100 substrate. DYM 100 is a polyester/polyether plastic used for interior automotive applications. After cure at 125° C./20' the coating and part of the substrate were microtomed and the microtomed slices extracted using supercritical fluid extraction. The extracts were analyzed for Compound E using HPLC. Compound E was not detected in any of the slices cut from the coating or from the substrate. Two conclusions are drawn from this result. First, Compound E was chemically bonded to the resin matrix, and therefore, could not be extracted from the coating. Second, Compound E did not migrate into the DYM 100 substrate.

Example 6
Accelerated Weathering Testing of Clear Coatings
Formation of Clear Coatings Compounds D and E were formulated in clear coatings which were applied to panels for accelerated weathering testing as follows. Compound D or E (1% or 2% based on total resin solids) and/or SANDUVOR® S-3055 HALS-type stabilizer (1% based on total resin solids) were predissolved in the solvent mixutre (to a 5–10% solids level) and added to the clear acrylic urethane formulation given in Table 3 below. Components I and II were mixed just before use. Cold roll steel panels measuring 4"×12" and precoated with an electro-coat primer ED505A and a white polyester acrylic melamine base-coat 9542AB839, obtained from ACT Laboratories, Inc. (Hillsdale, Mich.) were coated with the clear coating formulations of Table 3. The draw-down technique, using WC-60 WireCators™ (Leneta Co., Hohokus, N.J.), was used to apply the clear coat to the pre-coated panels. The clear coats were allowed to flash for 10 min at ambient temperature and cured for 30 min at 135° C.

TABLE 3

Acrylic Urethane Clear Coat Formulation

| Raw Material | Supplier | Amount |
|---|---|---|
| Component I Composition: | | |
| Acrylic Resin: JONCRYL ® CDX-588 (70% Solids) | S. C. Johnson & Son, Inc., Racine, WI | 100 parts |
| Catalyst Solution | | 5 parts |
| Solvent Mixture | | 45 parts |
| Triazine UV Absorber | | 1 or 2 parts[a] |
| SANDUVOR ® S-33055 (HALS type stabilizer) | Clariant Corp., Charlotte, NC | 1 part[b] |
| Component II Composition: | | |
| Isocyanate: DESMODUR ® N-3390 (90% Solids) | Miles Inc., Pittsburgh, PA | 33 parts |
| Solvent Mixture | | 17 parts |
| Catalyst Solution Composition: (2% Solids in Catalyst Solution) | | |
| Dibutyltin Dilaurate: T-12 | Air Products, Allentown, PA | 1 part |
| Acetic Acid | | 4 parts |
| Propylene Glycol Methyl Ether Acetate (PM Acetate) Solvent Mixture: | | 45 parts |
| Xylenes | | 1 part |
| PM Acetate | | 1 part |
| Methyl Amyl Ketone (MAK) | | 1 part |

[a]Amount for 1% or for 2% based on total resin solids
[b]Optional - when utilized the amount for 1% based on total resin solids Accelerated weathering was carried out on the clear coating formulations using a QUV device equipped with UVB-313 fluorescent bulbs. The coated panels were subjected to accelerated weathering under alternate cycles of (i) UV light at 70° C. for 8 hours and (ii) condensation with no UV light at 50° C. for 4 hours (ASTM G53, GM cycle). Specular properties such as gloss (200, ASTMD523) and distinctness of image ("DOI") (Dorigon Meter D47R-6FT, Hunter Associate Laboratory) and yellowing ("Delta b") were measured as a function of weathering time.

The results for QUV exposure using Compounds D or E as the sole stabilizer are presented below in Table 4. The results for QUV exposure using Compounds D or E in combination with S-3055 HALS are presented below in Table 5.

TABLE 4

QUV Weathering (UVA Alone)

| Hours QUV | % Comp. D | % Comp. E | Gloss | DOI | b |
|---|---|---|---|---|---|
| 0 | — | — | 93.5 | 77.0 | 3.65 |
| | 2 | — | 95.5 | 85.2 | 3.81 |
| | — | 2 | 94.3 | 78.2 | 3.82 |

TABLE 4-continued

QUV Weathering (UVA Alone)

| Hours QUV | % Comp. D | % Comp. E | % Gloss Retention | % DOI Retention | Delta b |
|---|---|---|---|---|---|
| 544 | — | — | 100.5 | 94.8 | 5.93 |
|  | 2 | — | 100.0 | 101.9 | 2.56 |
|  | — | 2 | 100.7 | 101.5 | 2.45 |
| 1047 | — | — | 101.4 | 97.1 | 8.81 |
|  | 2 | — | 100.9 | 102.6 | 3.36 |
|  | — | 2 | 101.5 | 102.3 | 3.38 |
| 1449 | — | — | 101.9 | 101.9 | 10.48 |
|  | 2 | — | 100.6 | 104.0 | 3.91 |
|  | — | 2 | 101.2 | 104.1 | 4.04 |
| 1984 | — | — | 98.4 | 101.4 | 11.01 |
|  | 2 | — | 98.4 | 103.2 | 4.48 |
|  | — | 2 | 98.2 | 102.9 | 4.61 |
| 2486 | — | — | 29.1 | 13.1 | 10.80 |
|  | 2 | — | 94.9 | 103.3 | 5.01 |
|  | — | 2 | 94.3 | 103.1 | 5.28 |
| 2989 | — | — | fail | fail | fail |
|  | 2 | — | 86.5 | 99.6 | 5.37 |
|  | — | 2 | 75.5 | 89.8 | 5.42 |

TABLE 5

QUV Weathering (UVA + HALS)

| Hours QUV | % Comp. D | % Comp. E | % HALS | Gloss | DOI | b |
|---|---|---|---|---|---|---|
| 0 | — | — | 1 | 94.1 | 88.8 | 3.70 |
|  | 2 | — | 1 | 94.6 | 85.1 | 3.86 |
|  | — | 2 | 1 | 94.8 | 90.3 | 3.86 |

| Hours QUV | % Comp. D | % Comp. E | % HALS | % Gloss Retention | % DOI Retention | Delta b |
|---|---|---|---|---|---|---|
| 544 | — | — | 1 | 100.0 | 101.1 | 2.94 |
|  | 2 | — | 1 | 101.1 | 101.1 | 0.93 |
|  | — | 2 | 1 | 100.1 | 100.0 | 0.87 |
| 1047 | — | — | 1 | 101.7 | 100.6 | 3.80 |
|  | 2 | — | 1 | 101.5 | 101.5 | 1.44 |
|  | — | 2 | 1 | 101.6 | 100.3 | 1.43 |
| 1449 | — | — | 1 | 101.1 | 101.2 | 4.47 |
|  | 2 | — | 1 | 101.8 | 102.5 | 1.75 |
|  | — | 2 | 1 | 101.5 | 101.1 | 1.74 |
| 1984 | — | — | 1 | 100.3 | 101.1 | 5.44 |
|  | 2 | — | 1 | 100.8 | 102.5 | 2.15 |
|  | — | 2 | 1 | 100.4 | 100.8 | 2.11 |
| 2486 | — | — | 1 | 97.4 | 99.0 | 6.89 |
|  | 2 | — | 1 | 98.3 | 102.5 | 2.47 |
|  | — | 2 | 1 | 98.2 | 100.9 | 2.51 |
| 2989 | — | — | 1 | 88.4 | 98.5 | 8.13 |
|  | 2 | — | 1 | 89.6 | 114.6 | 2.75 |
|  | — | 2 | 1 | 89.7 | 101.0 | 2.66 |
| 3467 | — | — | 1 | 39.7 | 13.5 | 7.72 |
|  | 2 | — | 1 | 98.9 | 103.3 | 2.99 |
|  | — | 2 | 1 | 96.7 | 100.9 | 2.98 |
| 3967 | — | — | 1 | 24.5 | 15.0 | 8.08 |
|  | 2 | — | 1 | 94.3 | 102.1 | 3.23 |
|  | — | 2 | 1 | 87.7 | 96.5 | 3.33 |
| 4443 | — | — | 1 | fail | fail | fail |
|  | 2 | — | 1 | 91.4 | 98.1 | 3.26 |
|  | — | 2 | 1 | 74.1 | 76.0 | 3.52 |

Example 7
Weathering of Clear Coatings Comprising Compound G

Example 6 was repeated, except that Compound G was used in place of Compounds D and E. The results for QUV exposure using Compound G as the sole stabilizer, and in combination with a HALS, are presented below in Table 6.

TABLE 6

QUV Weathering (UVA alone and UVA + HALS)

| Hours QUV | % Comp. G | % HALS | Gloss | DOI | b |
|---|---|---|---|---|---|
| 0 | — | — | 94.2 | 80.0 | 4.11 |
|  | 2 | — | 95.2 | 86.9 | 4.29 |
|  | 1 | 1 | 94.4 | 85.6 | 4.06 |

| Hours QUV | % Comp. G | % HALS | % Gloss Retention | % DOI Retention | Delta b |
|---|---|---|---|---|---|
| 501 | — | — | 101.6 | 101.5 | 5.18 |
|  | 2 | — | 100.9 | 100.6 | 2.38 |
|  | 1 | 1 | 102.0 | 100.4 | 1.09 |
| 1004 | — | — | 102.5 | 103.6 | 6.81 |
|  | 2 | — | 101.9 | 100.5 | 3.13 |
|  | 1 | 1 | 102.8 | 100.5 | 1.76 |
| 1515 | — | — | 98.0 | 104.0 | 9.13 |
|  | 2 | — | 100.6 | 100.5 | 4.67 |
|  | 1 | 1 | 100.4 | 101.3 | 2.52 |
| 1998 | — | — | 81.8 | 72.1 | 9.82 |
|  | 2 | — | 92.0 | 96.3 | 5.31 |
|  | 1 | 1 | 99.5 | 95.4 | 2.66 |
| 2499 | — | — | 57.0 | 44.0 | 8.05 |
|  | 2 | — | 75.6 | 64.3 | 5.79 |
|  | 1 | 1 | 105.4 | 101.9 | 3.68 |
| 3003 | — | — | fail | fail | fail |
|  | 2 | — | 51.8 | 30.3 | 6.12 |
|  | 1 | 1 | 95.3 | 100.4 | 3.78 |

Example 8
Weathering of Clear Coatings—Compound I

The effectiveness of the light stabilizer systems of the following examples was determined by measuring the gloss and % gloss retention (ASTM D523), and DOI and % DO1 retention (Dorigon Meter D47R-6FT, Hunter Associate Laboratory), of a coating after exposure in a QUV accelerated weathering unit equipped with UVA-340 fluorescent bulbs.

Standard 4"×12" steel test panels available from ACT Laboratories, coated with a primer (ED11) and a white base coat (DuPont 872AB839 white), were coated by drawing down with a #52 wire cator a clear coating as described below. The coated panel was cured for 30 mm. at 135° C.

The clear coating comprised the following basic components:

| | |
|---|---|
| 27.10 parts | JONCRYL ® 510 thermosetting acrylic resin (80% solids) (S. C. Johnson & Sons), |
| 11.67 parts | CYMEL ® 303 amino resin crosslinking agent (Cytec Industries), |
| 0.33 parts | CYCAT ® 4040 toluene sulfonic acid catalyst (40% solids in isopropanol) (Cytec Industries), |
| 0.33 parts | DC-57 silicone leveling agent (10% solids) (Dow Corning), |
| 5.33 parts | xylene, and |
| 6.67 parts | n-butanol. |

Compound I was added to this clear coating in the amounts set forth in the tables below (in wt % based upon solids).

The coated panels were then subject to accelerated weathering under alternate cycles of (i) UV light at 70° C. for 8 hours and (ii) condensation with no UV light at 50° C. for 4 hours (ASTM G53, GM Cycle).

The results are presented in Table 7 below. As can be seen from these results, the panels without Compound I began degrading at an early stage in the exposure cycle, and failed in about half the time of the panels containing Compound I.

TABLE 7

QUV Weathering (UVA Alone)

| Hours QUV | % Comp. I | Gloss | % Ret. | DOI | % Ret. |
|---|---|---|---|---|---|
| 1513 | 2 | 98.1 | 99.0 | 93.8 | 98.3 |
|  | 1 | 98.2 | 98.5 | 94.2 | 98.3 |
|  | — | 97.0 | 99.8 | 91.4 | 95.6 |
| 2498 | 2 | 97.7 | 98.6 | 93.4 | 97.9 |
|  | 1 | 97.8 | 98.1 | 93.7 | 97.8 |
|  | — | 93.2 | 95.9 | 80.7 | 84.4 |
| 2999 | 2 | 99.3 | 100.2 | 92.9 | 97.4 |
|  | 1 | 99.7 | 100.0 | 93.5 | 97.6 |
|  | — | 90.0 | 92.6 | 56.1 | 58.7 |
| 3501 | 2 | 98.0 | 98.9 | 92.5 | 97.0 |
|  | 1 | 99.8 | 100.1 | 93.4 | 97.5 |
|  | — | 63.0 | 64.8 | 34.1 | 35.7 |
| 4005 | 2 | 96.0 | 96.9 | 92.2 | 96.6 |
|  | 1 | 97.3 | 97.6 | 93.2 | 97.3 |
|  | — | 51.5 | 53.0 | 26.5 | 27.7 |
| 4508 | 2 | 96.4 | 97.3 | 91.2 | 95.6 |
|  | 1 | 97.1 | 97.4 | 92.9 | 97.0 |
|  | — | fail | fail | fail | fail |
| 5516 | 2 | 91.6 | 92.4 | 89.0 | 93.3 |
|  | 1 | 85.7 | 86.0 | 79.4 | 82.9 |
|  | — | fail | fail | fail | fail |
| 5996 | 2 | 84.5 | 85.3 | 84.7 | 88.8 |
|  | 1 | 76.6 | 76.8 | 71.5 | 74.6 |
|  | — | fail | fail | fail | fail |
| 6496 | 2 | 72.1 | 72.8 | 69.9 | 73.3 |
|  | 1 | 59.9 | 60.1 | 60.4 | 63.0 |
|  | — | fail | fail | fail | fail |

Example 9

Weathering of Clear Coatings—Compound I—HALS

Example 8 was repeated, except Compound I was used in combination with a HALS (SANDOVUR® S-3058, Clariant Corp.). The results are presented in Table 8 below.

TABLE 8

QUV Weathering (UVA + HALS)

| Hours QUV | % Comp. I | % HALS | Gloss | % Ret. | DOI - | % Ret. |
|---|---|---|---|---|---|---|
| 1513 | 2 | 1 | 99.2 | 99.4 | 96.5 | 98.9 |
|  | 1 | 0.5 | 97.8 | 98.0 | 94.8 | 98.9 |
|  | — | 1 | 96.9 | 99.3 | 94.9 | 97.9 |
|  | — | 0.5 | 97.8 | 100.4 | 93.7 | 97.6 |
| 2498 | 2 | 1 | 98.3 | 98.5 | 96.2 | 98.6 |
|  | 1 | 0.5 | 99.1 | 99.3 | 94.5 | 98.5 |
|  | — | 1 | 97.9 | 100.3 | 94.5 | 97.5 |
|  | — | 0.5 | 98.4 | 101.0 | 93.4 | 97.3 |
| 2999 | 2 | 1 | 100.7 | 100.9 | 95.9 | 98.3 |
|  | 1 | 0.5 | 101.1 | 101.3 | 93.7 | 97.7 |
|  | — | 1 | 99.5 | 101.9 | 94.3 | 97.3 |
|  | — | 0.5 | 99.7 | 102.4 | 93.9 | 97.8 |
| 3501 | 2 | 1 | 100.1 | 100.3 | 95.6 | 98.0 |
|  | 1 | 0.5 | 97.8 | 98.9 | 94.0 | 98.0 |
|  | — | 1 | 99.1 | 101.5 | 94.0 | 97.0 |
|  | — | 0.5 | 99.1 | 101.7 | 93.0 | 96.9 |
| 4005 | 2 | 1 | 98.5 | 98.7 | 95.5 | 97.8 |
|  | 1 | 0.5 | 98.2 | 98.4 | 94.0 | 98.0 |
|  | — | 1 | 97.7 | 100.1 | 92.5 | 95.5 |
|  | — | 0.5 | 98.0 | 100.6 | 92.9 | 96.8 |
| 4508 | 2 | 1 | 99.3 | 99.5 | 95.2 | 97.5 |
|  | 1 | 0.5 | 98.8 | 99.0 | 94.1 | 98.1 |
|  | — | 1 | 99.3 | 101.7 | 93.7 | 96.7 |
|  | — | 0.5 | 98.7 | 101.3 | 91.5 | 95.3 |
| 5516 | 2 | 1 | 98.4 | 98.6 | 94.6 | 96.9 |
|  | 1 | 0.5 | 96.4 | 96.6 | 93.4 | 97.4 |
|  | — | 1 | 97.6 | 100.0 | 92.6 | 95.6 |
|  | — | 0.5 | 92.9 | 95.4 | 74.4 | 77.5 |
| 5996 | 2 | 1 | 97.8 | 98.0 | 94.1 | 96.4 |
|  | 1 | 0.5 | 96.0 | 96.2 | 93.4 | 97.4 |
|  | — | 1 | 96.8 | 99.2 | 92.0 | 94.9 |
|  | — | 0.5 | 87.8 | 90.1 | 65.4 | 68.1 |
| 6496 | 2 | 1 | 97.0 | 97.2 | 93.6 | 95.9 |
|  | 1 | 0.5 | 95.7 | 975.9 | 93.0 | 97.0 |
|  | — | 1 | 97.5 | 99.9 | 90.6 | 93.5 |
|  | — | 0.5 | 79.8 | 81.9 | 55.8 | 58.1 |
| 7000 | 2 | 1 | 95.7 | 95.9 | 93.2 | 95.5 |
|  | 1 | 0.5 | 94.3 | 94.5 | 93.0 | 97.0 |
|  | — | 1 | 93.4 | 95.7 | 83.8 | 86.5 |
|  | — | 0.5 | 73.1 | 75.1 | 51.2 | 53.3 |
| 7502 | 2 | 1 | 93.8 | 94.0 | 93.0 | 95.3 |
|  | 1 | 0.5 | 92.9 | 93.1 | 92.8 | 96.8 |
|  | — | 1 | 91.0 | 93.2 | 73.9 | 76.3 |
|  | — | 0.5 | 62.6 | 64.3 | 46.8 | 48.8 |
| 8041 | 2 | 1 | 90.7 | 90.9 | 92.2 | 94.5 |
|  | 1 | 0.5 | 88.3 | 88.5 | 92.0 | 95.9 |
|  | — | 1 | 69.0 | 70.7 | 50.7 | 52.3 |
|  | — | 0.5 | fail | fail | fail | fail |
| 8540 | 2 | 1 | 90.3 | 90.5 | 91.8 | 94.1 |
|  | 1 | 0.5 | 86.4 | 86.6 | 91.5 | 95.4 |
|  | — | 1 | 64.1 | 65.7 | 45.6 | 47.1 |
|  | — | 0.5 | fail | fail | fail | fail |

Example 10

Weathering of Clear Coatings—Synergy of Compounds E and F with HALS

TABLE 8

QUV Weathering (UVA + HALS)

| Hours Exposure | % Comp. E | % Comp. F | % HALS | Gloss | DOI | b |
|---|---|---|---|---|---|---|
| 0 | — | — | — | 88.6 | 60.4 | 3.66 |
|  | 2 | — | — | 89.2 | 60.3 | 3.79 |
|  | — | 2 | — | 66.3 | 32.9 | 3.90 |
|  | — | — | 2 | 88.5 | 56.7 | 3.74 |
|  | 1 | — | 1 | 91.4 | 65.6 | 3.74 |
|  | — | 1 | 1 | 88.5 | 63.0 | 3.77 |
|  |  |  |  | % Gloss Retention | % DOI Retention | Delta b |
| 1997 | — | — | — | 106.9 | 125.5 | 7.64 |
|  | 2 | — | — | 102.8 | 112.1 | 3.46 |
|  | — | 2 | — | 110.0 | 115.5 | 3.27 |
|  | — | — | 2 | 105.0 | 116.0 | 3.35 |
|  | 1 | — | 1 | 104.0 | 108.2 | 2.38 |
|  | — | 1 | 1 | 102.8 | 103.7 | 2.31 |
| 2507 | — | — | — | 43.9 | 29.6 | 8.59 |
|  | 2 | — | — | 95.1 | 101.2 | 3.88 |
|  | — | 2 | — | 100.5 | 87.5 | 3.71 |
|  | — | — | 2 | 101.7 | 119.6 | 4.20 |
|  | 1 | — | 1 | 100.4 | 118.3 | 2.79 |
|  | — | 1 | 1 | 98.8 | 99.4 | 2.78 |
| 3012 | — | — | — | fail | fail | fail |
|  | 2 | — | — | 70.0 | 56.7 | 4.99 |
|  | — | 2 | — | 90.3 | 58.1 | 4.52 |
|  | — | — | 2 | 104.7 | 116.9 | 5.55 |
|  | 1 | — | 1 | 98.9 | 101.2 | 3,33 |
|  | — | 1 | 1 | 96.8 | 99.0 | 3.39 |
| 3513 | — | — | — | fail | fail | fail |
|  | 2 | — | — | 16.3 | 0.0 | 5.30 |
|  | — | 2 | — | 38.5 | 19.8 | 5.02 |
|  | — | — | 2 | 102.1 | 127.5 | 6.42 |
|  | 1 | — | 1 | 96.7 | 110.9 | 4.07 |
|  | — | 1 | 1 | 97.1 | 103.0 | 4.06 |

TABLE 8-continued

QUV Weathering (UVA + HALS)

| Hours Exposure | % Comp. E | % Comp. F | % HALS | | | |
|---|---|---|---|---|---|---|
| 4017 | — | — | — | fail | fail | fail |
|  | 2 | — | — | 26.5 | 14.4 | 5.99 |
|  | — | 2 | — | 40.9 | 35.0 | 5.28 |
|  | — | — | 2 | 28.5 | 35.9 | 5.51 |
|  | 1 | — | 1 | 85.9 | 93.8 | 3.93 |
|  | — | 1 | 1 | 83.8 | 87.0 | 4.06 |
| 4515 | — | — | — | fail | fail | fail |
|  | 2 | — | — | fail | fail | fail |
|  | — | 2 | — | fail | fail | fail |
|  | — | — | 2 | fail | fail | fail |
|  | 1 | — | 1 | 72.5 | 76.6 | 4.23 |
|  | — | 1 | 1 | 59.7 | 64.9 | 4.18 |

The clear coating composition of Example 6 was used to evaluate the performance of Compounds E and F, alone at 2%, and in combination with a HALS, SANDUVOR® 3055 (1% of Compound E plus 1% of S-3055; and 1% of Compound G plus 1% of S-3055). These coating compositions were weathered by QUV according to the method of Example 6. The results are presented in Table 8.

The data show that not only do Compounds E and F extend the lifetime of the coating compositions in terms of percent gloss retention, percent DOI retention, and yellowing (delta b) compared to the unstabilized composition, but that the combinations of HALS plus Compounds E and F used at the same total concentrations as the individual stabilizers when used alone (1% of each for 2% total concentration) exhibit a synergistic effect on these properties.

As can be seen from the results, the panels with Compound I maintained high gloss and distinctness of image significantly longer than the panels without such compound.

Although the present invention is described with reference to certain preferred embodiments, it is apparent that modifications and variations thereof may be made by those skilled in the art without departing from the scope of this invention as defined by the appended claims.

What is claimed is:

1. A compound of the formulas (I), (IA), (II) or (III):

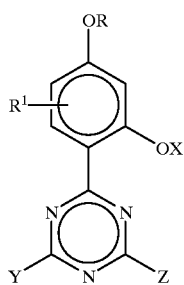
(I)

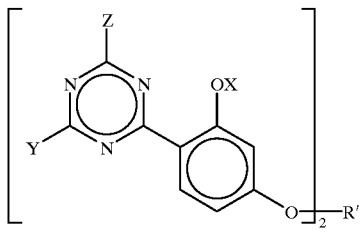
(IA)

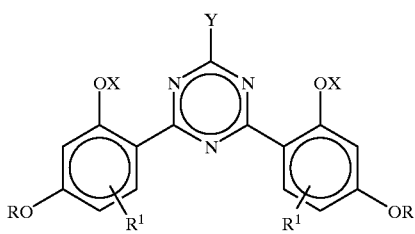
(II)

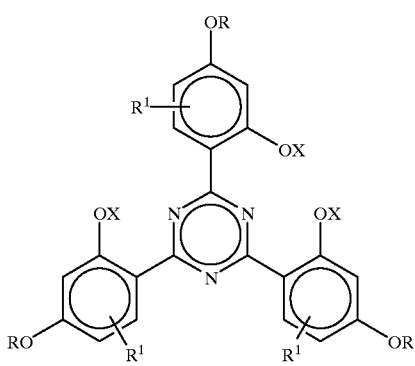
(III)

wherein
each X is independently selected from hydrogen and a blocking group; each of Y and Z is independently selected from an aryl ring of the general formula (IV)

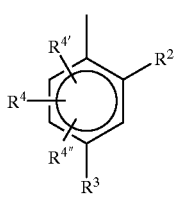
(IV)

each R is independently selected from a hydrogen, a hydrocarbyl group and a functional hydrocarbyl group;
R' is selected from a divalent hydrocarbyl group and a functional divalent hydrocarbyl group;
each $R^1$, $R^2$, $R^4$, $R^{4'}$ and $R^{4''}$ is independently selected from hydrogen, hydrocarbyl, functional hydrocarbyl, —O(hydrocarbyl), —O(functional hydrocarbyl), —SR, halogen, —SO$_2$R, —SO$_3$R, —COOR, —COR, —OCOR, —NRR and cyano; and
each $R^3$ is independently selected from —R, —OR, —SR, halogen, —SO$_2$R, —SO$_3$R, —COOR, —COR, —NRR and cyano;
wherein at least one R group of a 4-position —OR group is selected from a group of the formulas (V) ("amido group") and (VI) ("carbamate group")

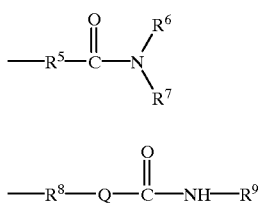

wherein
  Q is selected from NR$^{10}$ and O;
  R$^5$ is selected from a direct bond and a hydrocarbylene group; R$^8$ is a hydrocarbylene group;
  each R$^6$ and R$^7$ is independently selected from a hydrocarbyl group and a functional hydrocarbyl group, wherein at least one of R$^6$ and R$^7$ is a functional hydrocarbyl group; or
  R$^6$ and R$^7$ taken together form a group selected from a functional hydrocarbylene group, an unsaturated hydrocarbylene group and an activated unsaturated hydrocarbylene group;
  each R$^9$ is selected from hydrogen, a hydrocarbyl group and a functional hydrocarbyl group; and
  R$^{10}$ is selected from hydrogen and a hydrocarbyl group.

2. The compound of claim 1, wherein at least one R group of a 4-position —OR group is a group of the formula V, and (i) each of R$^6$ and R$^7$ is independently selected from a hydrocarbyl group of 1 to 50 carbon atoms and a functional hydrocarbyl group of 1 to 50 carbon atoms, with at least one of R$^6$ and R$^7$ being such a functional hydrocarbyl group; or (ii) R$^6$ and R$^7$ taken together form a group selected from a functional hydrocarbylene group 3 to 24 carbon atoms, an unsaturated hydrocarbylene group having 3 to 24 carbon atoms and an activated unsaturated hydrocarbylene group having 3 to 24 carbon atoms.

3. The compound of claim 2, wherein at least one of R$^6$ and R$^7$ is a functional hydrocarbyl group possessing pendant and/or terminal reactive and/or latent reactive functionality and/or leaving groups.

4. The compound of claim 3, wherein R$^5$ is —(CHR$^{14}$)$_n$; and R$^6$ and R$^7$ are each independently selected from the group consisting of hydrogen, linear or branched alkyl of 1 to 24 carbon atoms, —(CH$_2$)$_n$OH, —(CH$_2$)CH(OH)CH$_2$OR$^{15}$, —(CH$_2$)CH(OH)CH$_2$R$^{15}$ and

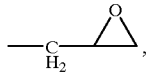

wherein R$^{14}$ and R$^{15}$ are each independently selected from hydrogen or linear or branched alkyl of 1 to 24 carbon atoms.

5. The compound of claim 4, wherein at least one of R$^6$ and R$^7$ is a functional hydrocarbyl group possessing a pendant and/or terminal group selected from the group consisting of hydroxyl, —COOR$^{11}$, —CR$^{12}$=CH$_2$, —CO—CR$^{12}$=CH$_2$, —OCO—CR$^{12}$—CH$_2$, —OCO—NH—R$^9$, Cl,

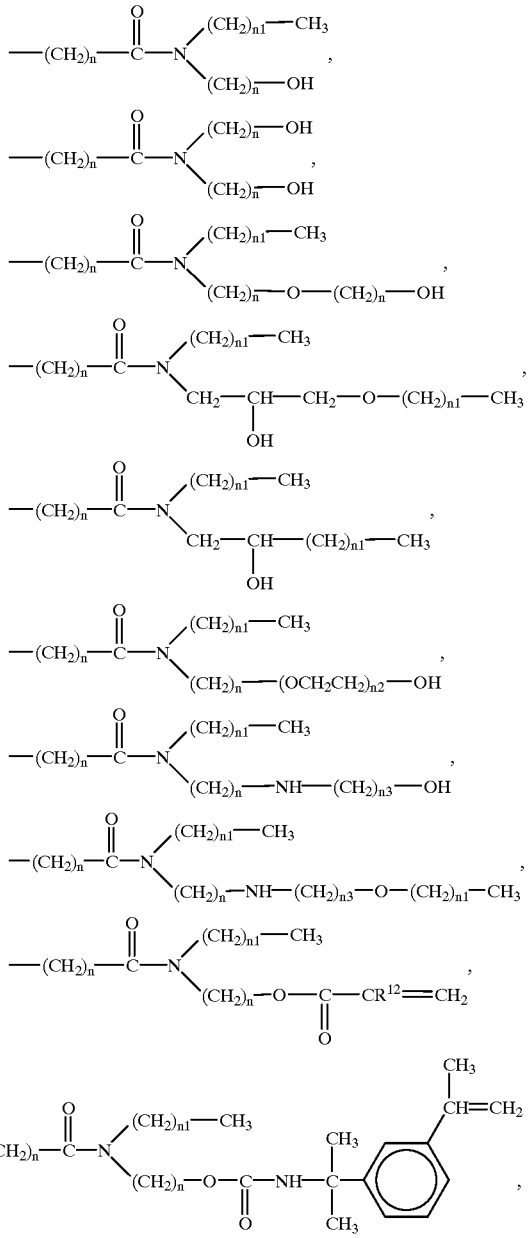

an isocyanate group, a blocked isocyanate group and —NHR$^{11}$,
  wherein
    R$^{11}$ is selected from hydrogen and a hydrocarbyl; and
    R$^{12}$ is selected from hydrogen and an alkyl of 1 to 4 carbon atoms.

6. The compound of claim 5, wherein at least one R group of a 4-position —OR group is a group selected from

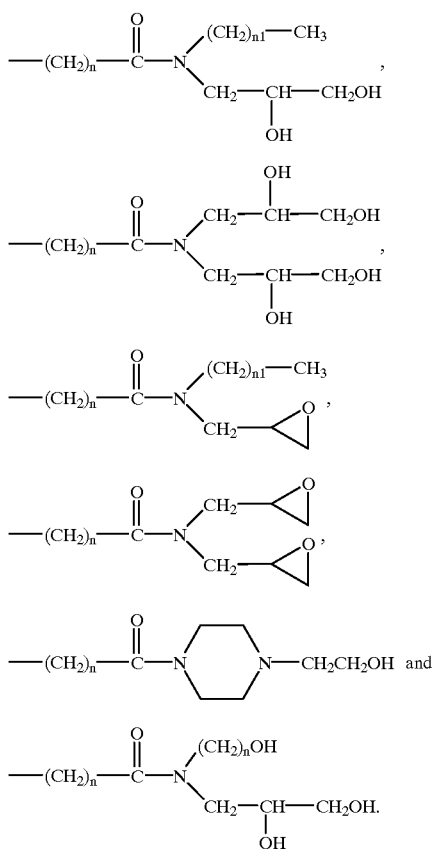

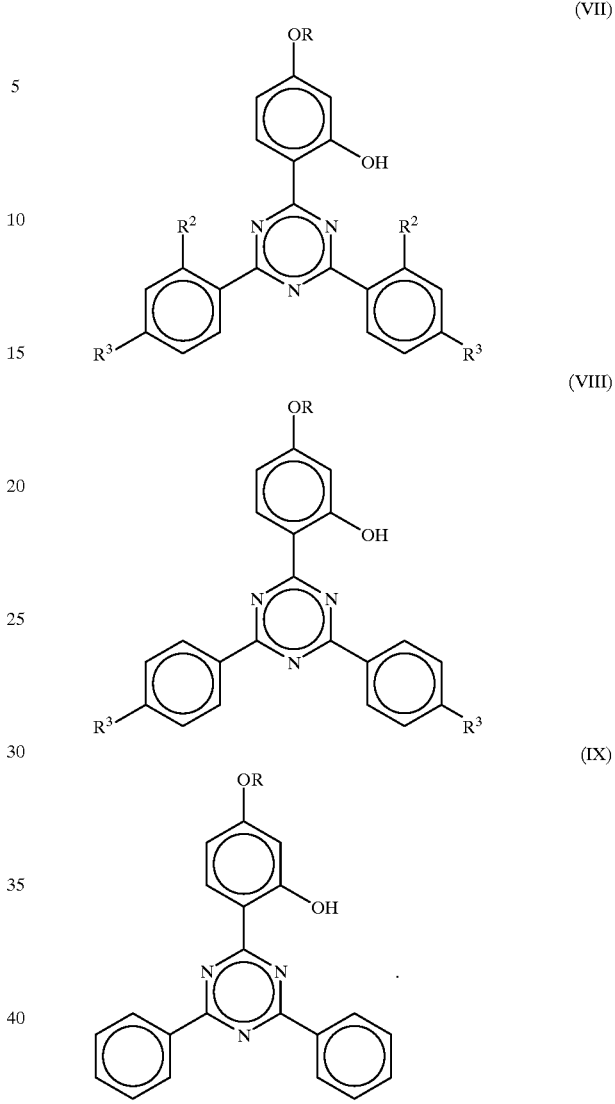

7. The compound of claim 1, wherein at least one R of a 4-position —OR group is a group of the formula VI, and $R^9$ is selected from hydrogen, a hydrocarbyl group of 1 to 50 carbon atoms and a functional hydrocarbyl group of 1 to 50 carbon atoms.

8. The compound of claim 7, wherein at least one R of a 4-position —OR group is a group selected from

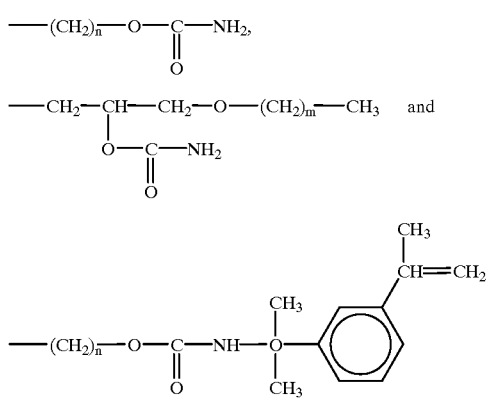

wherein n is 1–24 and n1 is 0–23.

9. A compound according to claim 1, having the formula (VII), (VIII) or (IX):

10. The compound of claim 9, wherein at least one R group of a 4-position —OR group is a group of the formula V, and (i) each of $R^6$ and $R^7$ is independently selected from a hydrocarbyl group of 1 to 50 carbon atoms and a functional hydrocarbyl group of 1 to 50 carbon atoms, with at least one of $R^6$ and $R^7$ being such a functional hydrocarbyl group; or (ii) $R^6$ and $R^7$ taken together form a group selected from a functional hydrocarbylene group 3 to 24 carbon atoms, an unsaturated hydrocarbylene group having 3 to 24 carbon atoms and an activated unsaturated hydrocarbylene group having 3 to 24 carbon atoms.

11. The compound of claim 10, wherein at least one of $R^6$ and $R^7$ is a functional hydrocarbyl group possessing pendant and/or terminal reactive and/or latent reactive functionality and/or leaving groups.

12. The compound of claim 10, wherein $R^5$ is —$(CHR^{14})n$—; and $R^6$ and $R^7$ are each independently selected from the group consisting of hydrogen, linear or branched alkyl of 1 to 24 carbon atoms, —$(CH_2)_nOH$, —$(CH_2)CH(OH)CH_2OR^{15}$, —$(CH_2)CH(OH)CH_2R^{15}$ and 13. The compound of claim 13, wherein at least one of $R^6$ and $R^7$ is a functional hydrocarbyl group possessing a pendant and/or terminal group selected from the group consisting of hydroxyl, —COOR", —CR$^{12}$=CH$_2$, —CO—CR$^{12}$=CH$_2$, —OCO—CR$^{12}$=CH$_2$, —OCO—NH—R$^9$, Cl,

[structures: epoxide (—CH$_2$-epoxide), glycidyl (—CH(OH)CH$_2$-epoxide ... actually —CH(H)-epoxide-CH$_2$), maleimide, tetrahydrophthalimide]

an isocyanate group, a blocked isocyanate group and —NHR$^{11}$,
wherein
  $R^{11}$ is selected from hydrogen and a hydrocarbyl; and
  $R^{12}$ is selected from hydrogen and an alkyl of 1 to 4 carbon atoms.

14. The compound of claim 13, wherein at least one R group of a 4-position —OR group is a group selected from

[series of structures of the form —(CH$_2$)$_n$—C(=O)—N(R)(R') with various substituents including:
—(CH$_2$)$_n$—C(=O)—N((CH$_2$)$_{n1}$—CH$_3$)((CH$_2$)$_n$—OH),
—(CH$_2$)$_n$—C(=O)—N((CH$_2$)$_n$—OH)((CH$_2$)$_n$—OH),
—(CH$_2$)$_n$—C(=O)—N((CH$_2$)$_{n1}$—CH$_3$)((CH$_2$)$_n$—O—(CH$_2$)$_n$—OH),
—(CH$_2$)$_n$—C(=O)—N((CH$_2$)$_{n1}$—CH$_3$)(CH$_2$—CH(OH)—CH$_2$—O—(CH$_2$)$_{n1}$—CH$_3$),
—(CH$_2$)$_n$—C(=O)—N((CH$_2$)$_{n1}$—CH$_3$)(CH$_2$—CH(OH)—(CH$_2$)$_{n1}$—CH$_3$),
—(CH$_2$)$_n$—C(=O)—N((CH$_2$)$_{n1}$—CH$_3$)((CH$_2$)$_n$—(OCH$_2$CH$_2$)$_{n2}$—OH),
—(CH$_2$)$_n$—C(=O)—N((CH$_2$)$_{n1}$—CH$_3$)((CH$_2$)$_n$—NH—(CH$_2$)$_{n3}$—OH),
—(CH$_2$)$_n$—C(=O)—N((CH$_2$)$_{n1}$—CH$_3$)((CH$_2$)$_n$—NH—(CH$_2$)$_{n3}$—O—(CH$_2$)$_{n1}$—CH$_3$),
—(CH$_2$)$_n$—C(=O)—N((CH$_2$)$_{n1}$—CH$_3$)((CH$_2$)$_n$—O—C(=O)—CR$^{12}$=CH$_2$),
—(CH$_2$)$_n$—C(=O)—N((CH$_2$)$_{n1}$—CH$_3$)((CH$_2$)$_n$—O—C(=O)—NH—C(CH$_3$)$_2$—(m-isopropenylphenyl)),
—(CH$_2$)$_n$—C(=O)—N((CH$_2$)$_{n1}$—CH$_3$)(CH$_2$—CH(OH)—CH$_2$OH),
—(CH$_2$)$_n$—C(=O)—N(CH$_2$—CH(OH)—CH$_2$OH)(CH$_2$—CH(OH)—CH$_2$OH),
—(CH$_2$)$_n$—C(=O)—N((CH$_2$)$_{n1}$—CH$_3$)(CH$_2$-epoxide),
—(CH$_2$)$_n$—C(=O)—N(CH$_2$-epoxide)(CH$_2$-epoxide),
—(CH$_2$)$_n$—C(=O)—N(piperazine)—CH$_2$CH$_2$OH and
—(CH$_2$)$_n$—C(=O)—N((CH$_2$)$_n$OH)(CH$_2$—CH(OH)—CH$_2$OH),]

wherein n is 1–24, n1 is 0–23, n2 is 1–24, n3 is 1–24, and $R^{12}$ is selected from hydrogen and an alkyl group of 1 to 4 carbon atoms.

15. The compound of claim 9, wherein at least one R of a 4-position —OR group is a group of the formula VI, and $R^9$ is selected from hydrogen, a hydrocarbyl group of 1 to 50 carbon atoms and a functional hydrocarbyl group of 1 to 50 carbon atoms.

16. The compound of claim 15, wherein at least one R of a 4-position —OR group is a group selected from —(CH$_2$)$_n$—O—C(=O)—NH$_2$, —CH$_2$—CH(O—C(=O)—NH$_2$)—CH$_2$—O—(CH$_2$)$_m$—CH$_3$ and -continued

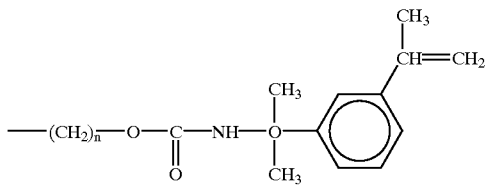

wherein n is 1–24 and n1 is 0–23.

17. A compound according to claim 1, having the formula (X), (XI) or (XII):

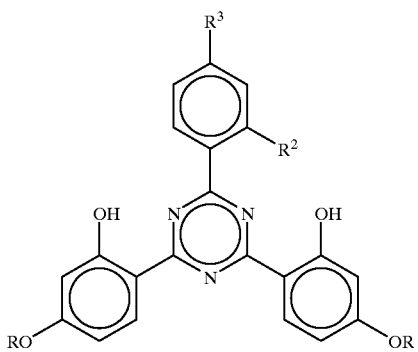  (X)

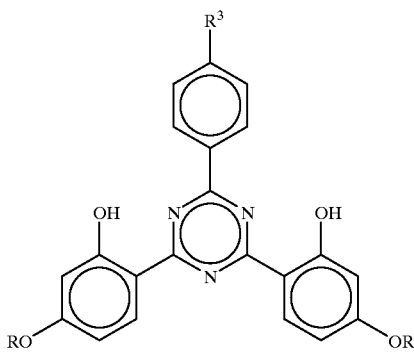  (XI)

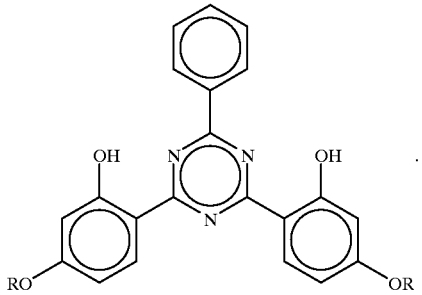  (XII)

18. The compound of claim 17, wherein at least one R group of a 4-position —OR group is a group of the formula V, and (i) each of $R^6$ and $R^7$ is independently selected from a hydrocarbyl group of 1 to 50 carbon atoms and a functional hydrocarbyl group of 1 to 50 carbon atoms, with at least one of $R^6$ and $R^7$ being such a functional hydrocarbyl group; or (ii) $R^6$ and $R^7$ taken together form a group selected from a functional hydrocarbylene group 3 to 24 carbon atoms, an unsaturated hydrocarbylene group having 3 to 24 carbon atoms and an activated unsaturated hydrocarbylene group having 3 to 24 carbon atoms.

19. The compound of claim 18, wherein at least one of $R^6$ and $R^7$ is a hydrocarbyl group containing a functional group selected from the group comprising pendant, terminal reactive, latent reactive functionality, or leaving groups.

20. The compound of claim 19, wherein $R^5$ is —(CHR$^{14}$)n—;

$R^6$ and $R^7$ are each independently selected from the group consisting of hydrogen, linear or branched alkyl of 1 to 24 carbon atoms, —(CH$_2$)$_n$OH, —(CH$_2$)CH(OH)CH$_2$OR$^{15}$, —(CH$_2$)CH(OH)CH$_2$R$^{15}$ and

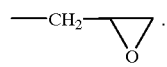

21. The compound of claim 19, wherein at least one of $R^6$ and $R^7$ is a functional hydrocarbyl group possessing a pendant and/or terminal group selected from the group consisting of hydroxyl, —COOR$^{11}$, —CR$^{12}$=CH$_2$, —CO—CR$^{12}$=CH$_2$, —OCO—CR$^{12}$=CH$_2$, —OCO—NH—R$^9$, Cl,

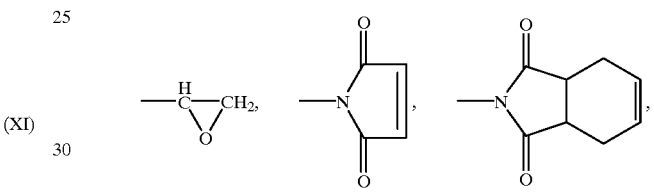

an isocyanate group, a blocked isocyanate group and —NHR$^{11}$, wherein $R^{11}$ is selected from hydrogen and a hydrocarbyl; and $R^{12}$ is selected from hydrogen and an alkyl of 1 to 4 carbon atoms.

22. The compound of claim 21, wherein at least one R group of a 4-position —OR group is a group selected from

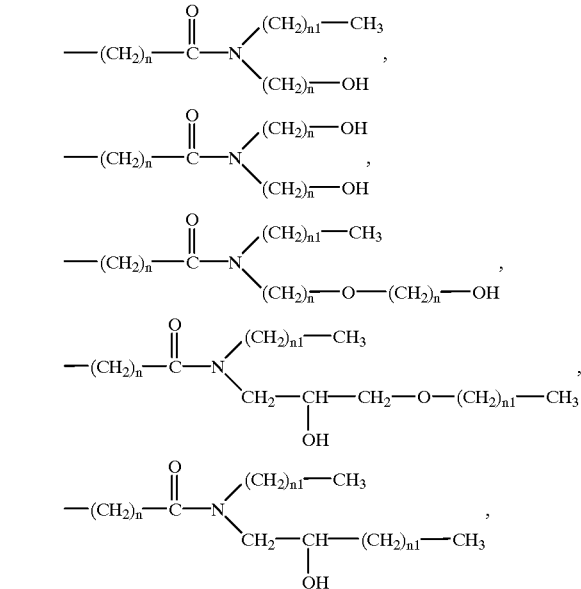

-continued

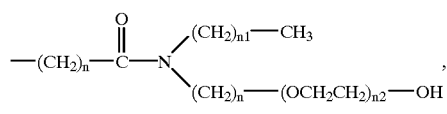

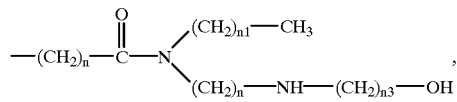

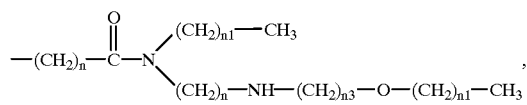

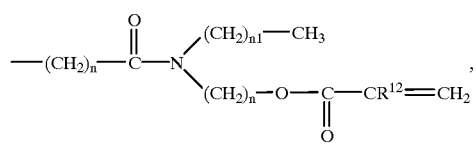

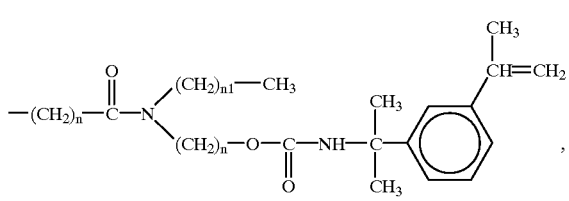

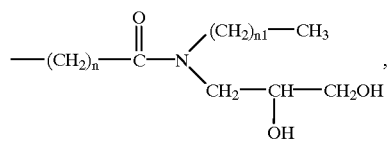

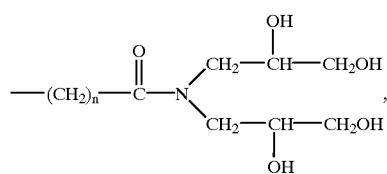

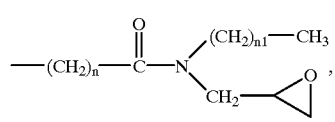

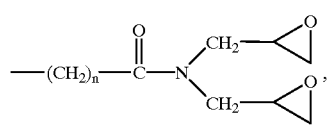

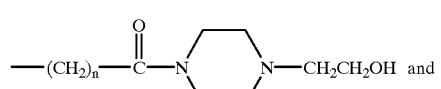

-continued

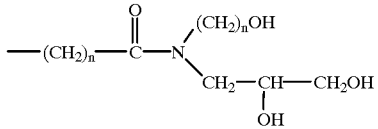

wherein n is 1–24, n1 is 0–23, n2 is 1–24, n3 is 1–24, and $R^{12}$ is selected from hydrogen and an alkyl group of 1 to 4 carbon atoms.

23. The compound of claim 17, wherein at least one R of a 4-position —OR group is a group of the formula VI, and $R^9$ is selected from hydrogen, a hydrocarbyl group of 1 to 50 carbon atoms and a functional hydrocarbyl group of 1 to 50 carbon atoms.

24. The compound of claim 23, wherein at least one R of a 4-position —OR group is a group selected from

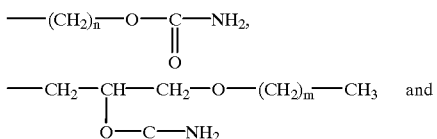

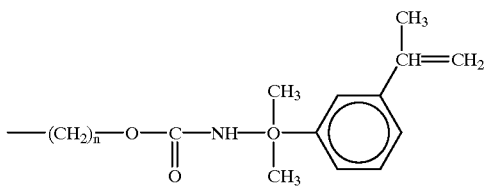

wherein n is 1–24 and n1 is 0–23.

25. A compound according to claim 1, having the formula (XIII):

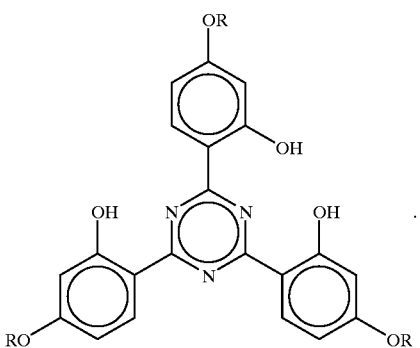

26. A compound according to claim 1, having the formula (XIV):

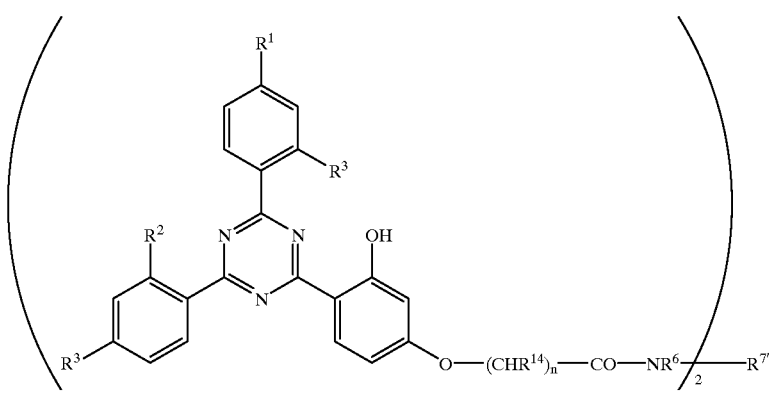

wherein $R^{14}$ is selected from hydrogen or linear or branched alkyl of 1 to 24 carbon atoms, $R^{7'}$ is selected from the group consisting of alkylene of 2 to 24 carbon atoms, alkenylene of 2 to 12 carbon atoms, xylylene and alkylene of 3 to 24 atoms which is interrupted by one or more oxygen atoms or substituted by —OH; or a diradical of formula (XV)

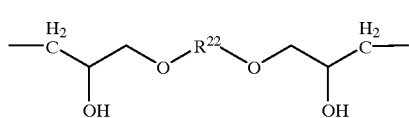

wherein $R^{22}$ is selected from alkylene of 2 to 10 carbon atoms and alkylene of 4 to 50 carbon atoms which is interrupted by one or more oxygen atoms or substituted by —OH;

or is a polyoxyalkylene bridge of the formula

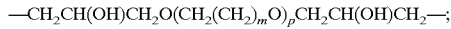

or is a polyoxyalkylene bridge of the formula

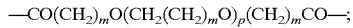

or is a polyoxyalkylene bridge of the formula

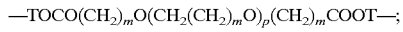

or is a polyoxyalkylene bridge of the formula

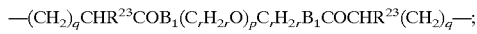

or is a polyoxyalkylene bridge of the formula

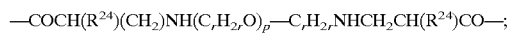

or is a polyoxyalkylene bridge of the formula

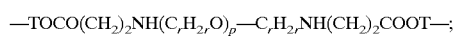

or is a polyoxyalkylene bridge of the formula

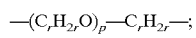

or is a polyoxyalkylene bridge of the formula

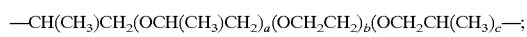

in which a+c=2.5 and b=8.5 to 40.5, or a+c=2 to 33 and b=0, wherein $R^{18}$ is hydrogen or alkyl of 1 to 18 carbon atoms;

$R^{23}$ is hydrogen or alkyl of 1 to 16 carbon atoms;

$R^{24}$ is hydrogen, alkyl of 1 to 4 carbon atoms or CN;

m is a number from 1 to 4;

p is a number from 2 to 60;

q is zero or a number from 1 to 16;

r is 2 to 6;

$B_1$ is a bridging group selected from —O—, —NH— or $NR^{18}$—; and

T is unsubstituted or substituted alkylene of 2 to 20 carbon atoms.

\* \* \* \* \*